US012064117B2

(12) United States Patent
Bakos et al.

(10) Patent No.: US 12,064,117 B2
(45) Date of Patent: Aug. 20, 2024

(54) DUAL STAGE CLOSURE SYSTEM FOR CIRCULAR SURGICAL STAPLER

(71) Applicant: Cilag GmbH International, Zug (CH)

(72) Inventors: Gregory J. Bakos, Mason, OH (US); Michael J. Stokes, Cincinnati, OH (US); Michael A. Jacobs, Villa Hills, KY (US); Disha V. Labhasetwar, Cincinnati, OH (US); Gregory G. Scott, Cincinnati, OH (US); Anthony Nguyen, West Chester, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/530,567

(22) Filed: Nov. 19, 2021

(65) Prior Publication Data

US 2022/0151621 A1 May 19, 2022

Related U.S. Application Data

(62) Division of application No. 16/159,851, filed on Oct. 15, 2018, now Pat. No. 11,207,071.

(51) Int. Cl.
*A61B 17/115* (2006.01)
*A61B 17/00* (2006.01)
*A61B 90/00* (2016.01)

(52) U.S. Cl.
CPC .......... *A61B 17/1155* (2013.01); *A61B 90/08* (2016.02); *A61B 2017/00367* (2013.01);
(Continued)

(58) Field of Classification Search
CPC ........................... A61B 17/115; A61B 17/1155
See application file for complete search history.

(56) References Cited

U.S. PATENT DOCUMENTS

| 4,047,654 A | 9/1977 | Alvarado |
| 4,351,466 A * | 9/1982 | Noiles .................. A61B 17/115 227/19 |

(Continued)

FOREIGN PATENT DOCUMENTS

| EP | 2992835 A2 | 3/2016 |
| EP | 3011915 A2 | 4/2016 |

(Continued)

OTHER PUBLICATIONS

European Search Report and Written Opinion dated Mar. 3, 2020, for Application No. 19203065.8, 11 pages.

(Continued)

*Primary Examiner* — Joshua G Kotis
(74) *Attorney, Agent, or Firm* — Frost Brown Todd LLP

(57) ABSTRACT

An apparatus includes a handle assembly having a body, a shaft assembly having an outer tube member, an end effector, an anvil, a first trocar closure system, and a second trocar closure system. The end effector has having a staple deck fixed relative to the body, a staple driver operable to actuate relative to the staple deck between an unfired position and a fired position, and the trocar configured to selectively couple with the anvil and actuate relative to the staple dreck. The first trocar closure assembly can actuate in a first motion to drive the trocar between a distal position and a first closed position. The second trocar closure assembly can actuate in a second motion between the first closed position and a second closed position. The staple drive is inoperable at least until the first trocar closure assembly actuates the trocar to the first closed position.

18 Claims, 46 Drawing Sheets

(52) U.S. Cl.
CPC .............. *A61B 2017/00473* (2013.01); *A61B 2017/00477* (2013.01); *A61B 2090/0811* (2016.02)

(56) References Cited

U.S. PATENT DOCUMENTS

| | | | |
|---|---|---|---|
| 4,488,523 | A | 12/1984 | Shichman |
| 4,573,468 | A | 3/1986 | Conta et al. |
| 4,907,591 | A | 3/1990 | Vasconcellos et al. |
| 5,205,459 | A | 4/1993 | Brinkerhoff et al. |
| 5,222,963 | A | 6/1993 | Brinkerhoff et al. |
| 5,271,543 | A | 12/1993 | Grant et al. |
| 5,271,544 | A | 12/1993 | Fox et al. |
| 5,275,322 | A | 1/1994 | Brinkerhoff et al. |
| 5,285,945 | A | 2/1994 | Brinkerhoff et al. |
| 5,292,053 | A | 4/1994 | Bilotti et al. |
| 5,333,773 | A | 8/1994 | Main et al. |
| 5,350,104 | A | 9/1994 | Main et al. |
| 5,376,098 | A | 12/1994 | Fontayne et al. |
| 5,443,198 | A | 8/1995 | Viola et al. |
| 5,533,661 | A | 7/1996 | Main et al. |
| 6,050,472 | A | 4/2000 | Shibata |
| 6,269,997 | B1 | 8/2001 | Balázs et al. |
| 7,794,475 | B2 | 9/2010 | Hess et al. |
| 8,459,524 | B2 | 6/2013 | Pribanic et al. |
| 8,910,847 | B2 | 12/2014 | Nalagatla et al. |
| 9,289,207 | B2 | 3/2016 | Shelton, IV |
| 9,463,022 | B2 | 10/2016 | Swayze et al. |
| 9,498,222 | B2 | 11/2016 | Scheib et al. |
| 9,532,783 | B2 | 1/2017 | Swayze et al. |
| 9,572,573 | B2 | 2/2017 | Scheib et al. |
| 9,597,081 | B2 | 3/2017 | Swayze et al. |
| 9,603,599 | B2 * | 3/2017 | Miller ................ A61B 17/1155 |
| 9,724,100 | B2 | 8/2017 | Scheib et al. |
| 9,936,949 | B2 | 4/2018 | Measamer et al. |
| 10,405,855 | B2 | 9/2019 | Stager et al. |
| 10,695,056 | B2 | 6/2020 | Zhang et al. |
| 11,051,819 | B2 | 7/2021 | Bakos et al. |
| 11,134,952 | B2 | 10/2021 | Bakos et al. |
| 11,207,071 | B2 | 12/2021 | Bakos et al. |
| 2005/0015103 | A1 | 1/2005 | Popov |
| 2009/0230170 | A1 | 9/2009 | Milliman |
| 2014/0158747 | A1 | 6/2014 | Measamer et al. |
| 2016/0106406 | A1 | 4/2016 | Cabrera et al. |
| 2016/0374665 | A1 * | 12/2016 | DiNardo .......... A61B 17/07207 227/175.2 |
| 2016/0374673 | A1 | 12/2016 | Stager et al. |
| 2016/0374684 | A1 | 12/2016 | DiNardo et al. |
| 2017/0196566 | A1 * | 7/2017 | Sgroi .................... A61B 17/34 |
| 2017/0281189 | A1 * | 10/2017 | Nalagatla ........... A61B 17/3211 |
| 2018/0280026 | A1 | 10/2018 | Zhang et al. |
| 2018/0353185 | A1 | 12/2018 | Nicholas |

FOREIGN PATENT DOCUMENTS

| | | |
|---|---|---|
| EP | 2100561 B1 | 8/2018 |
| JP | 2016-509890 A | 4/2016 |
| WO | WO 2016/137810 A1 | 9/2016 |
| WO | WO 2018/161314 | 9/2018 |

OTHER PUBLICATIONS

Indian Office Action dated Nov. 25, 2022, for Application No. 202117015951, 5 pages.

International Search Report and Written Opinion dated Nov. 12, 2019, for International Application No. PCT/IB2019/058690, 14 pages.

Brazilian Examination Report dated Jun. 5, 2023 for Application No. BR 112021007079-6, 4 pgs.

Japanese Office Action, Notification of Reasons for Refusal, dated Jul. 4, 2023 for Application No. JP 2021-544963, 6 pgs.

Chinese Office Action, Notification of the First Office Action, and First Search, dated Sep. 29, 2023 for Application No. CN 2019800678078, 13 pgs.

* cited by examiner

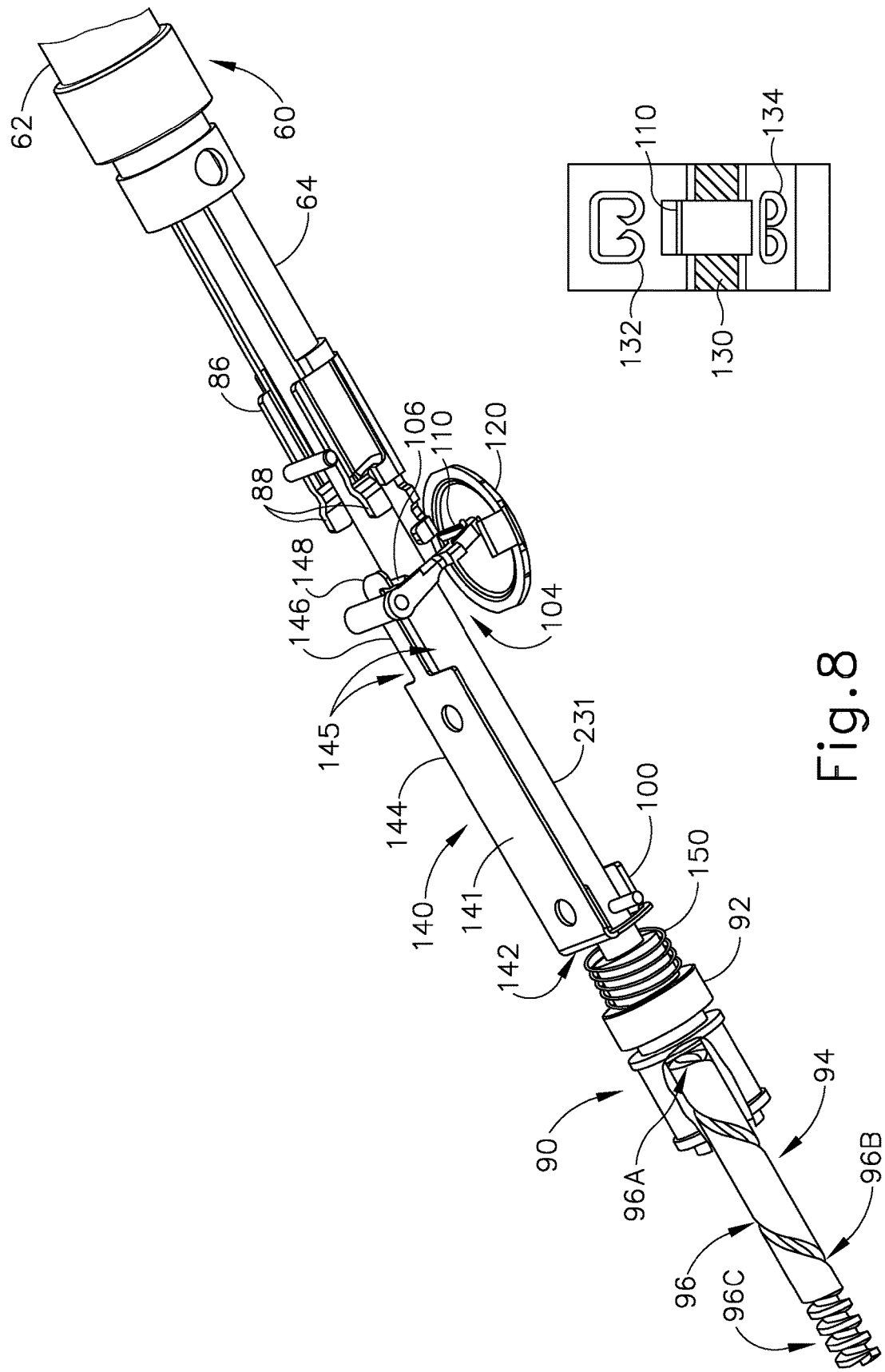

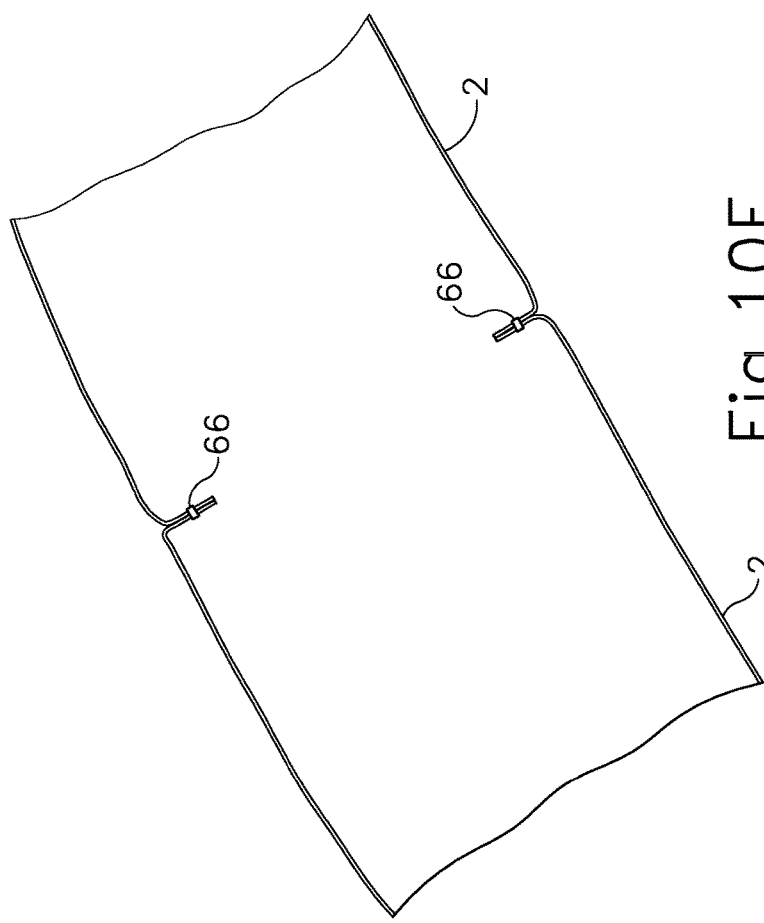
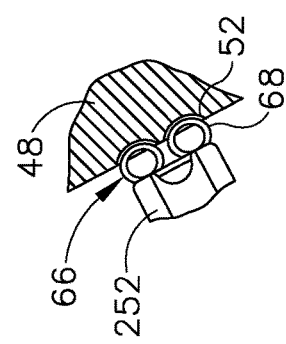

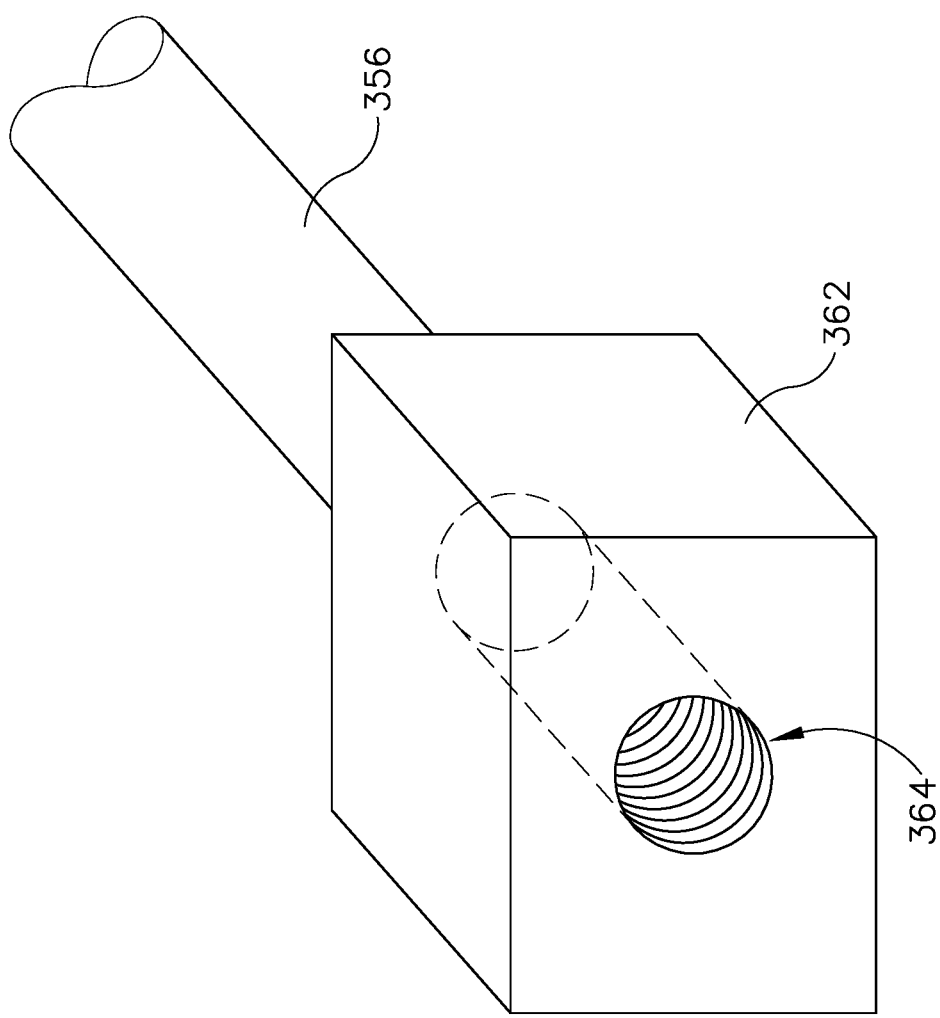

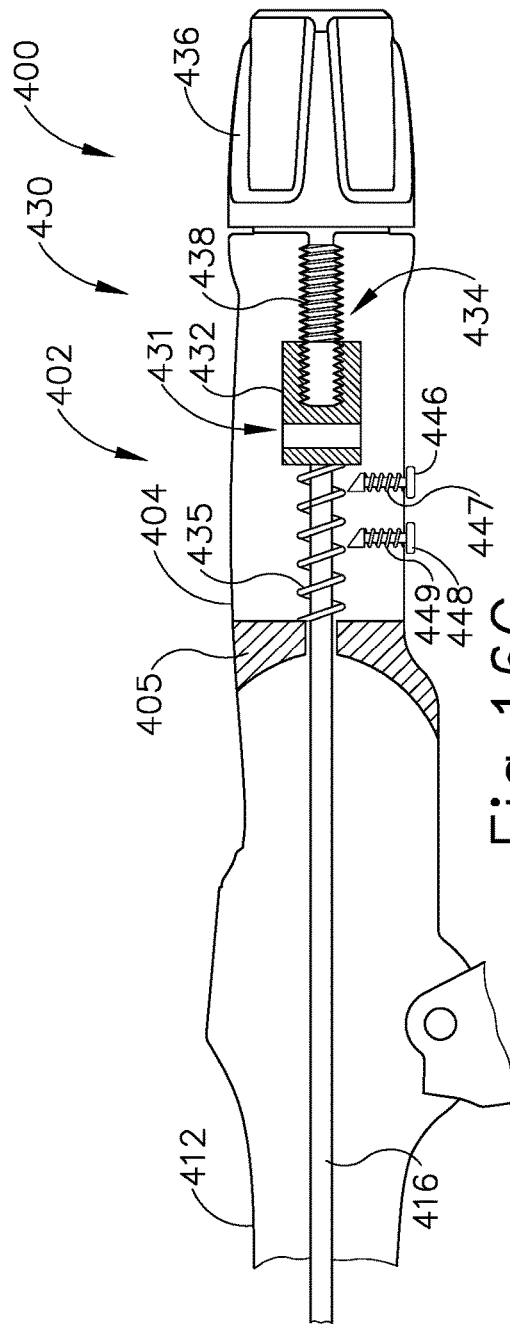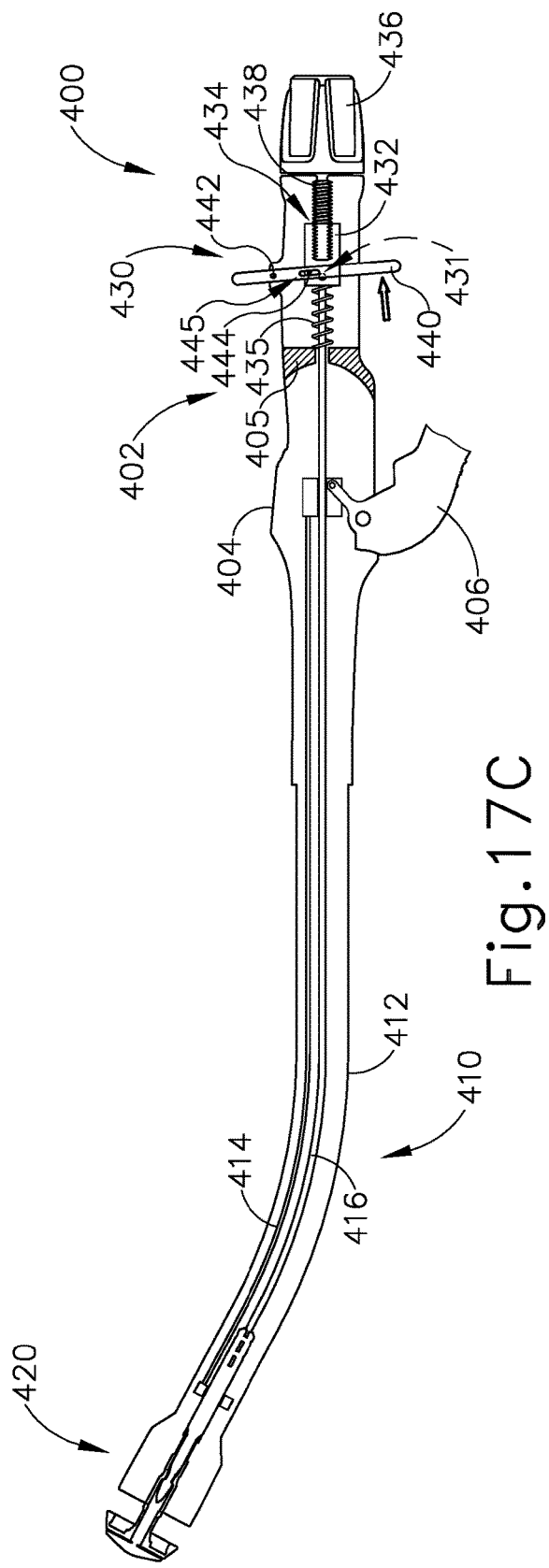

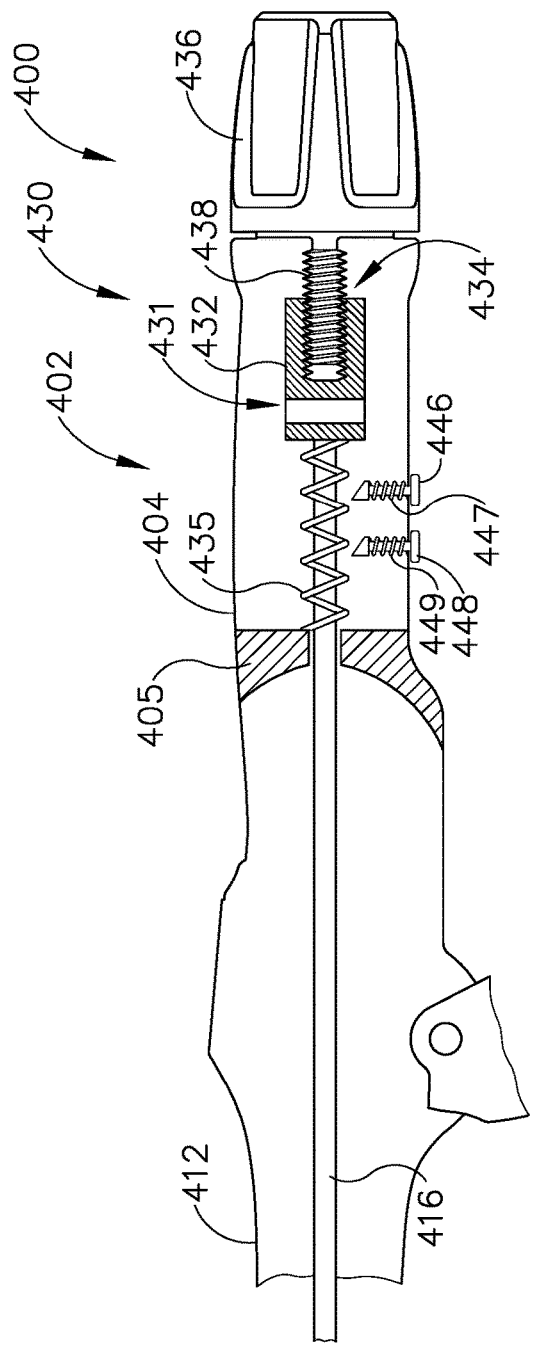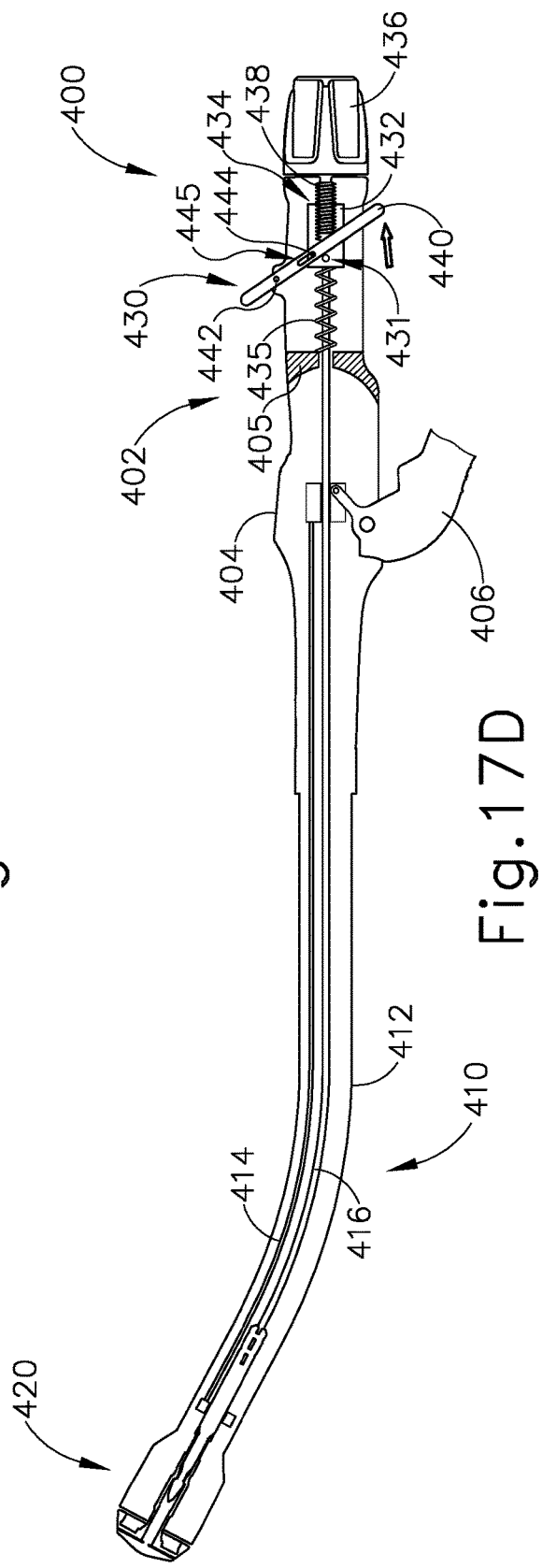
Fig.16D
Fig.17D

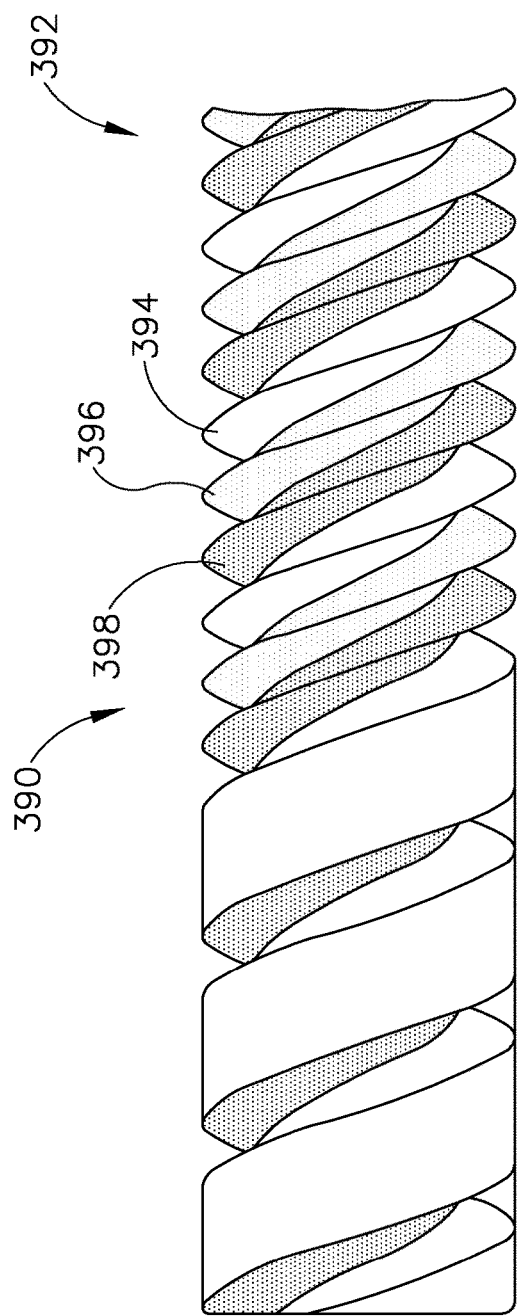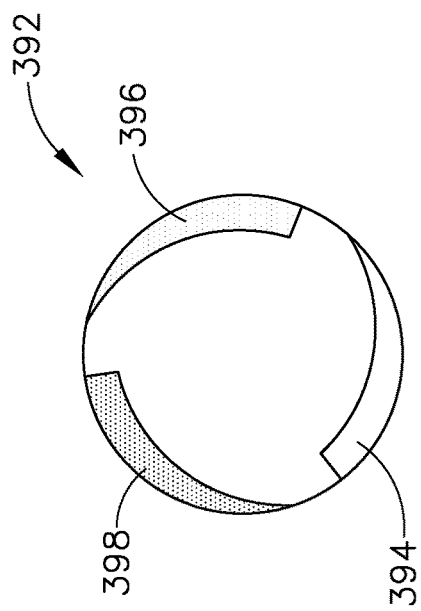

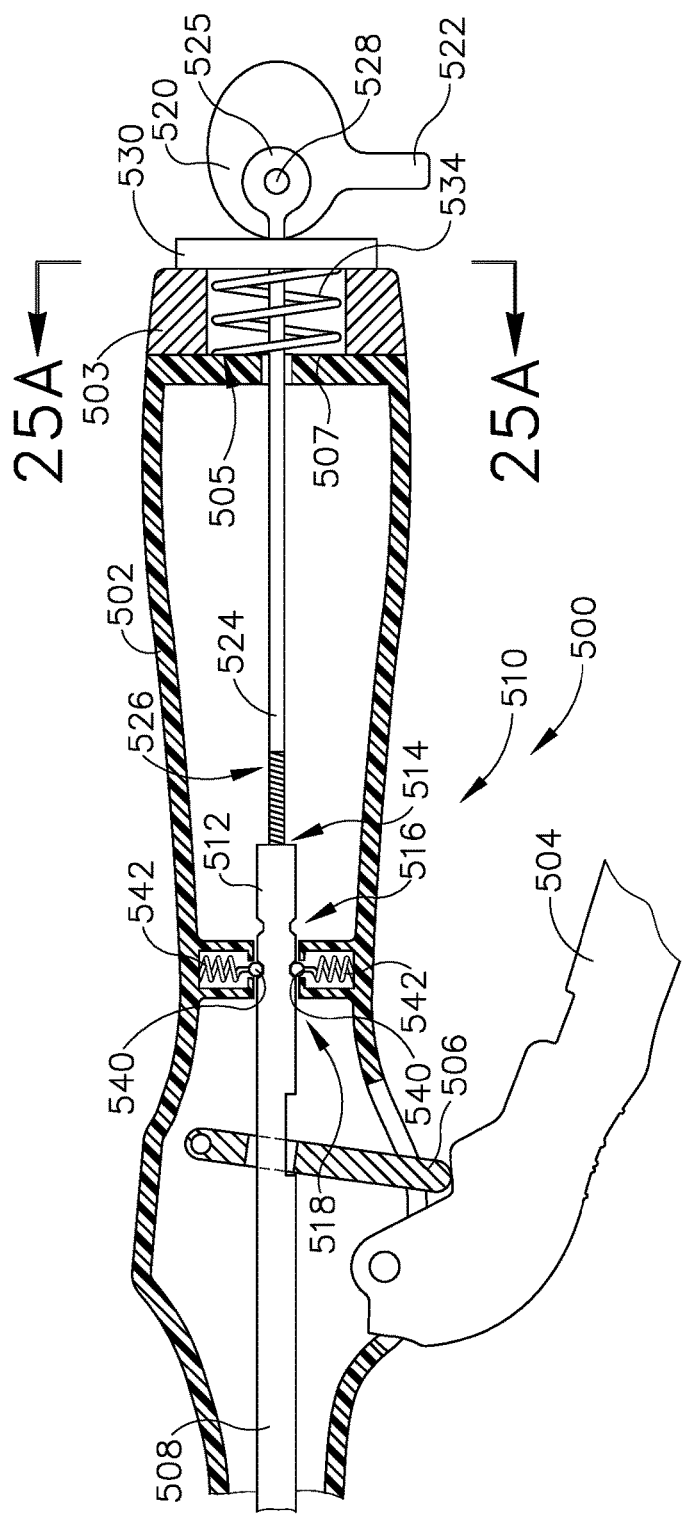
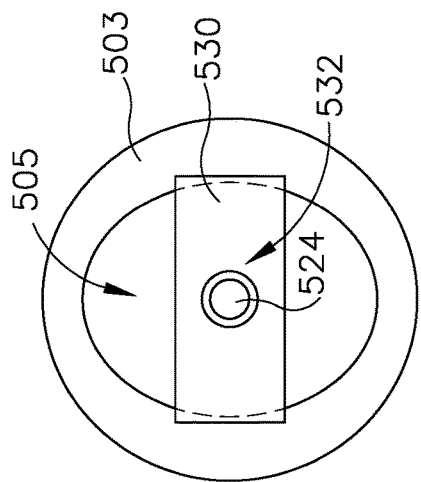
Fig.25A
Fig.24A

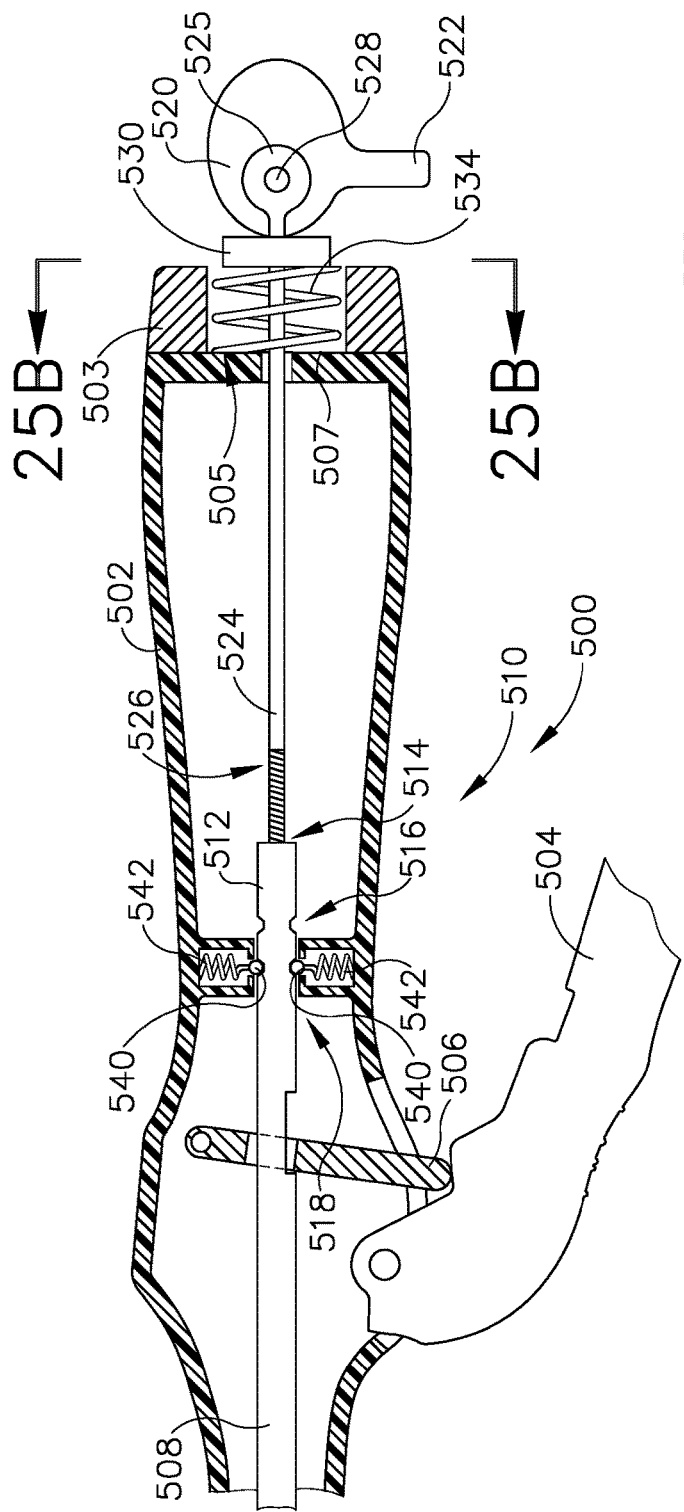
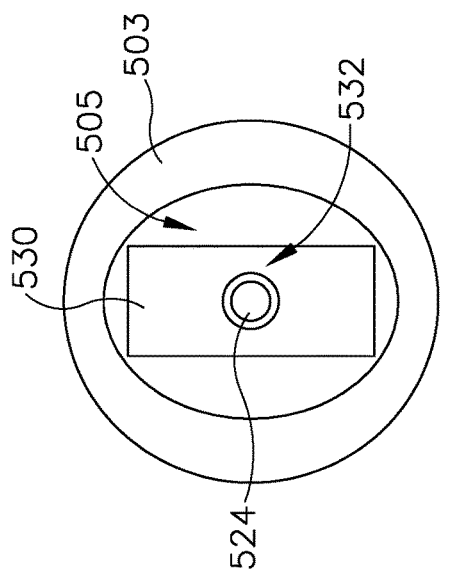
Fig.24B
Fig.25B

DUAL STAGE CLOSURE SYSTEM FOR CIRCULAR SURGICAL STAPLER

This application is a division of U.S. patent application Ser. No. 16/159,851, filed Oct. 15, 2018 and issued as U.S. Pat. No. 11,207,071 on Dec. 28, 2021.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts an enlarged partial perspective view of an exemplary indicator assembly of the surgical instrument of FIG. 1, showing an indicator window and indicator lever;

FIG. 9 depicts a diagrammatic view of the indicator window of FIG. 10, showing an exemplary indicator bar and exemplary corresponding staple representations;

FIG. 10E depicts an enlarged longitudinal cross-section view of the first tubular portion and the second tubular portion after the stapling head assembly of FIG. 5 and the anvil of FIG. 2 have been removed, leaving a completed end-to-end anastomosis;

FIG. 11 depicts an enlarged partial cross-sectional view of an exemplary staple formed against the anvil of FIG. 2;

FIG. 15 depicts a perspective view of a trocar and a proximal frame of the trocar actuation assembly of FIG. 14A;

FIG. 16C depicts a cross-sectional top view of a portion of the circular stapling surgical instrument of FIG. 16A, where the trocar actuation assembly is in a third configuration associated with the trocar and an anvil in a first closed position;

FIG. 16D depicts a cross-sectional top view of a portion of the circular stapling surgical instrument of FIG. 16A, where the trocar actuation assembly is in a fourth configuration associated with the trocar and an anvil in a second closed position;

FIG. 17C depicts a cross-sectional side view of a portion of the circular stapling surgical instrument of FIG. 16A, where the trocar actuation assembly is in the third configuration associated with the trocar and an anvil in the first closed position;

FIG. 17D depicts a cross-sectional side view of a portion of the circular stapling surgical instrument of FIG. 16A, where the trocar actuation assembly is in the fourth configuration associated with the trocar and the anvil in the second closed position;

FIG. 21 depicts an elevational side view of an alternative threaded rod that may be readily incorporated into the trocar actuation assemblies of FIGS. 13A, 14A, 16A, and 18A;

FIG. 22 depicts an elevational front view of the threaded rod of FIG. 21;

FIG. 24A depicts a cross-sectional side view of an alternative actuator handle assembly where the trocar actuation assembly is in the first configuration associated with the trocar in the pre-deployed position, where an oblong washer is in an obstructed position;

FIG. 24B depicts a cross-sectional side view of the actuator handle assembly of FIG. 24A, where the trocar actuation assembly is in the first configuration associated with the trocar in the pre-deployed position, where the oblong washer is in an unobstructed position;

FIG. 25A depicts a cross-sectional view of the actuator handle assembly of FIG. 24A, taken along line 25A-25A of FIG. 24A, where the oblong washer is in the obstructed position;

FIG. 25B depicts a cross-sectional view of the actuator handle assembly of FIG. 24A, taken along line 25B-25B of FIG. 24B, where the oblong washer is in the unobstructed position;

Figure 1:
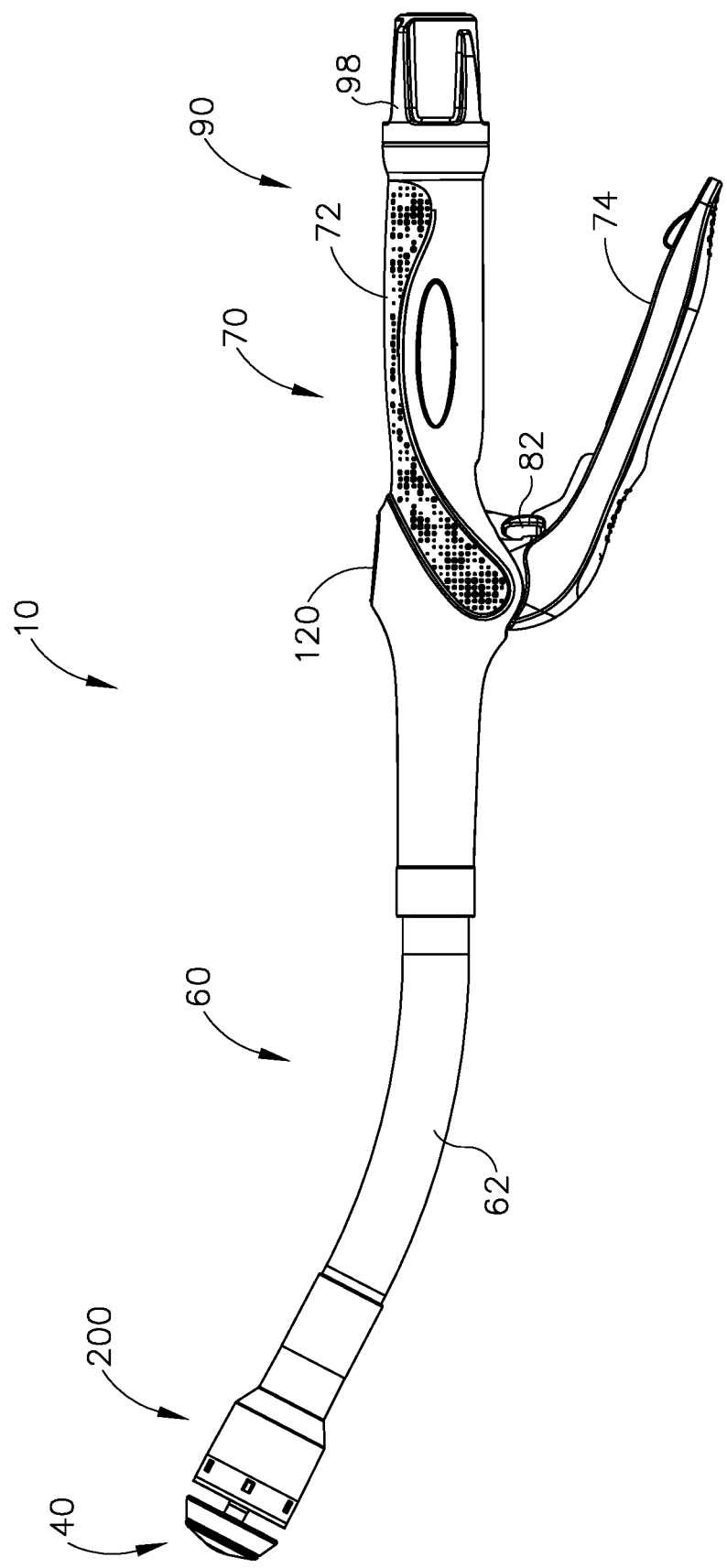
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-12B depict an exemplary circular surgical stapling instrument (10) having a stapling head assembly (200), a shaft assembly (60), and an actuator handle assembly (70), each of which will be described in more detail below. Shaft assembly (60) extends distally from actuator handle assembly (70), while stapling head assembly (200) is coupled to a distal end of shaft assembly (60). In brief, actuator handle assembly (70) is operable to actuate a staple driver member (250) of stapling head assembly (200) to drive a plurality of staples (66) out of stapling head assembly (200). Staples (66) are bent to form completed staples by an anvil (40) that is selectively attached at the distal end of instrument (10). Accordingly, tissue (2), as shown in FIGS. 10A-10E, may be stapled utilizing instrument (10).

In the present example, instrument (10) comprises a closure system and a firing system. As will be described in greater detail below, the closure system and anvil (40) are operable to clamp tissue between anvil (40) and stapling head assembly (200). As will also be described in greater detail below, the firing system and anvil (40) are operable to cut and staple tissue clamped between anvil (40) and stapling head assembly (200).

The closure system comprises an elongated coupling member in the form of a trocar (230), a trocar actuator (231), a connecting band portion (235), and an adjustment knob (98). Trocar actuator (231) is coupled to trocar (230) via connecting band portion (235). Anvil (40) may be selectively coupled to a distal end of trocar (230). Adjustment knob (98) is operable to longitudinally translate trocar (230) relative to stapling head assembly (200), thereby translating anvil (40) when anvil (40) is suitably coupled to trocar (230), and further clamping tissue between anvil (40) and stapling head assembly (200) as will be described in greater detail below.

The firing system comprises a trigger (74), a trigger actuation assembly (84), a driver actuator (64), and a staple driver member (250). Staple driver member (250) includes a knife member (240) configured to sever tissue when staple driver member (250) is actuated longitudinally. In addition, staples (66) are positioned distal to a plurality of staple drivers of staple driver member (250) such that staple driver member (250) also drives staples (66) distally when staple driver member (250) is actuated longitudinally. Thus, when trigger (74) is actuated and trigger actuation assembly (84) actuates staple driver member (250) via driver actuator (64), knife member (240) and staple drivers (252) substantially simultaneously sever tissue (2) and drive staples (66) distally relative to stapling head assembly (200) into tissue. The components and functionalities of the closure system and firing system will now be described in greater detail.

A. Exemplary Anvil

In the following discussion of anvil (40), the terms "distal" and "proximal" (and variations thereof) will be used with reference to the orientation of anvil (40) when anvil (40) is suitably coupled with trocar (230). Thus, proximal features of anvil (40) will be closer to the operator of instrument (10); while distal features of anvil (40) will be further from the operator of instrument (10).

Figure 3:
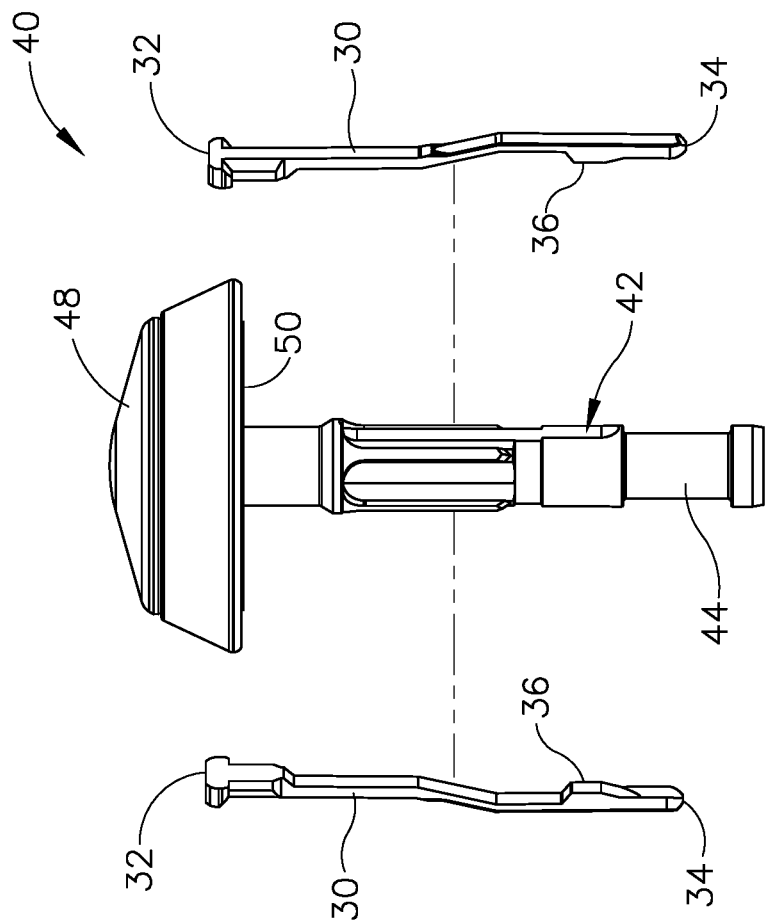
FIG. 3 depicts an exploded side elevational view of the anvil of FIG. 2.
Figure 2:
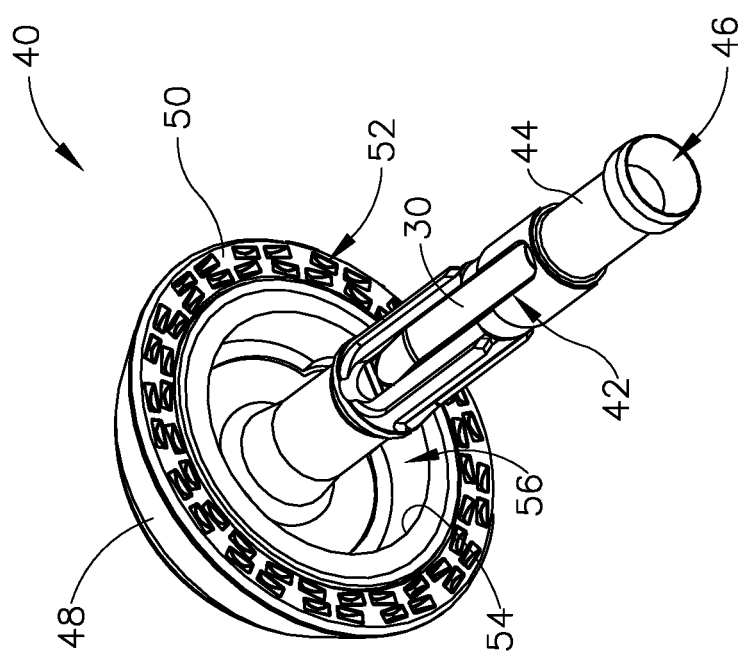
FIG. 2 depicts a perspective view of an exemplary anvil of the surgical instrument of FIG. 1.

As best seen in FIGS. 2-3, anvil (40) of the present example comprises a head (48) and a proximal shaft (44). As mentioned above and as will be described in greater detail below, anvil (40) of the present example may selectively couple to trocar (230) such that when coupled, movement of trocar (230) relative to stapling head assembly (200) also moves anvil (40) relative to stapling head assembly (200).

Head (48) includes a proximal surface (50) that defines a plurality of staple forming pockets (52). Staple forming pockets (52) are arranged in two concentric annular arrays. In some other versions, staple forming pockets (52) are arranged in three or more concentric annular arrays. Staple forming pockets (52) are configured to deform staples as the staples are driven into staple forming pockets (52). Accordingly, when anvil (40) is in the closed position and staples (66) are driven out of stapling head assembly (200) into staple forming pockets (52), each staple forming pocket (52) may deform a generally "U" shaped staple (66) into a "B" shape as is known in the art. As best seen in FIG. 2, proximal surface (50) terminates at an inner edge (54), which defines an outer boundary of an annular recess (56) surrounding proximal shaft (44).

Proximal shaft (44) defines a bore (46) and includes a pair of pivoting latch members (30) positioned in bore (46). As best seen in FIG. 3, each latch member (30) includes a "T" shaped distal end (32), a rounded proximal end (34), and a latch shelf (36) located distal to proximal end (34). "T" shaped distal ends (32) secure latch members (30) within bore (46). Latch members (30) are positioned within bore (46) such that proximal ends (34) are positioned at the proximal ends of lateral openings (42), which are formed through the sidewall of proximal shaft (44). Lateral openings (42) thus provide clearance for proximal ends (34) and latch shelves (36) to deflect radially outwardly from the longitudinal axis defined by proximal shaft (44). However, latch members (30) are configured to resiliently bias proximal ends (34) and latch shelves (36) radially inwardly toward the longitudinal axis defined by proximal shaft (44). Latch members (30) thus act as retaining clip to allow anvil (40) to be selectively secured to trocar (230) of stapling head assembly (200). It should be understood, however, that latch members (30) are merely optional. Anvil (40) may be removably secured to a trocar (230) using any other suitable components, features, or techniques.

In addition to or in lieu of the foregoing, anvil (40) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pub. No. 2016/0374684, issued as U.S. Pat. No. 10,226,253 on Mar. 12, 2019, the disclosures of which are incorporated by reference herein. Still other suitable configurations will be apparent to one of ordinary skill in the art in view of the teachings herein.

B. Exemplary Stapling Head Assembly

Figure 4:
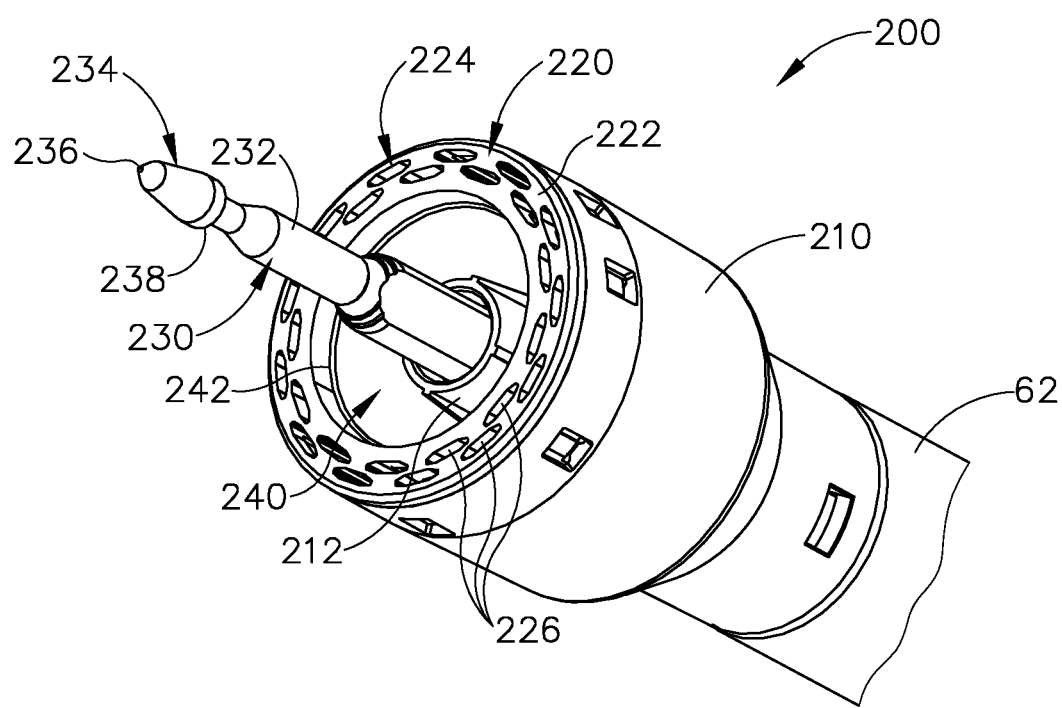
FIG. 4 depicts a perspective view of a stapling head assembly of the surgical instrument of FIG. 1.
Figure 5:
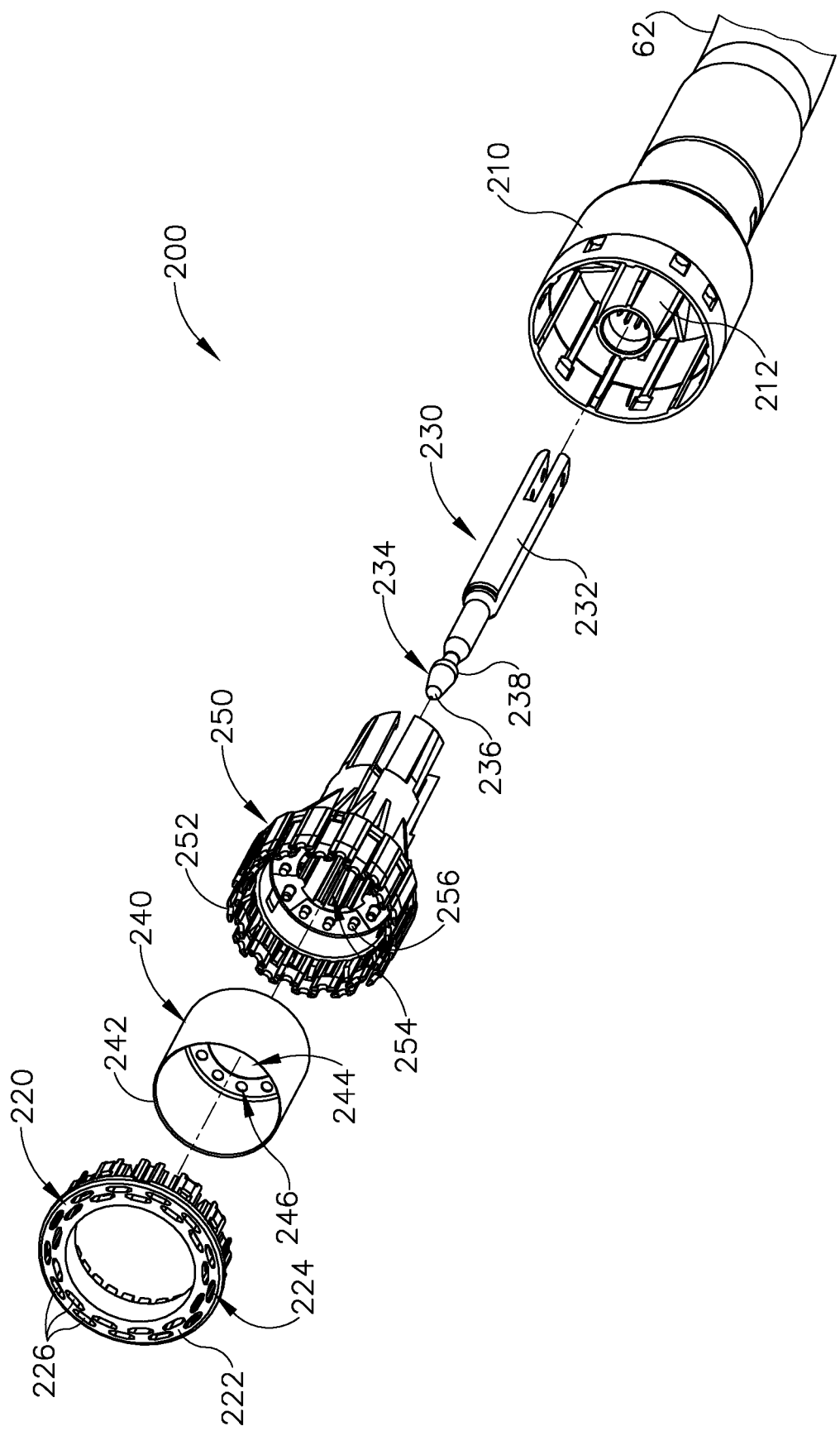
FIG. 5 depicts an exploded perspective view of the stapling head assembly of FIG. 5.

As best seen in FIGS. 4-5, stapling head assembly (200) of the present example is coupled to a distal end of shaft assembly (60) and comprises a tubular casing (210) housing a slidable staple driver member (250). A cylindraceous inner core member (212) extends distally within tubular casing (210). Tubular casing (210) is fixedly secured to an outer tubular member (62) of shaft assembly (60), such that tubular casing (210) serves as a mechanical ground for stapling head assembly (200).

Trocar (230) is positioned coaxially within inner core member (212) of tubular casing (210). As mentioned above and as will be described in greater detail below, trocar (230) is operable to translate distally and proximally relative to tubular casing (210) in response to rotation of adjustment knob (98) relative to body (72) of handle assembly (70). Trocar (230) comprises a shaft (232) and a head (234). Head (234) includes a pointed tip (236) and an inwardly extending proximal surface (238). Shaft (232) thus provides a reduced outer diameter just proximal to head (234), with surface (238) providing a transition between that reduced outer diameter of shaft (232) and the outer diameter of head (234). While tip (236) is pointed in the present example, tip (236) is not sharp. Tip (236) will thus not easily cause trauma to tissue due to inadvertent contact with tissue. Head (234) and the distal portion of shaft (232) are configured for insertion in bore (46) of anvil (40). Proximal surface (238) and latch shelves (36) have complementary positions and configurations such that latch shelves (36) engage proximal surface (238) when proximal shaft (44) of anvil (40) is fully seated on trocar (230). Anvil (40) may thus secure to trocar (230) through a snap fitting between latch members (30) and head (234). In addition, or in the alternative, trocar (230) may include a magnetic portion (not shown) which may attract anvil (40) towards trocar (230). Still further configurations and arrangements for anvil (40) and trocar (230) will be apparent to one of ordinary skill in the art in view of the teachings herein.

Figure 10A:
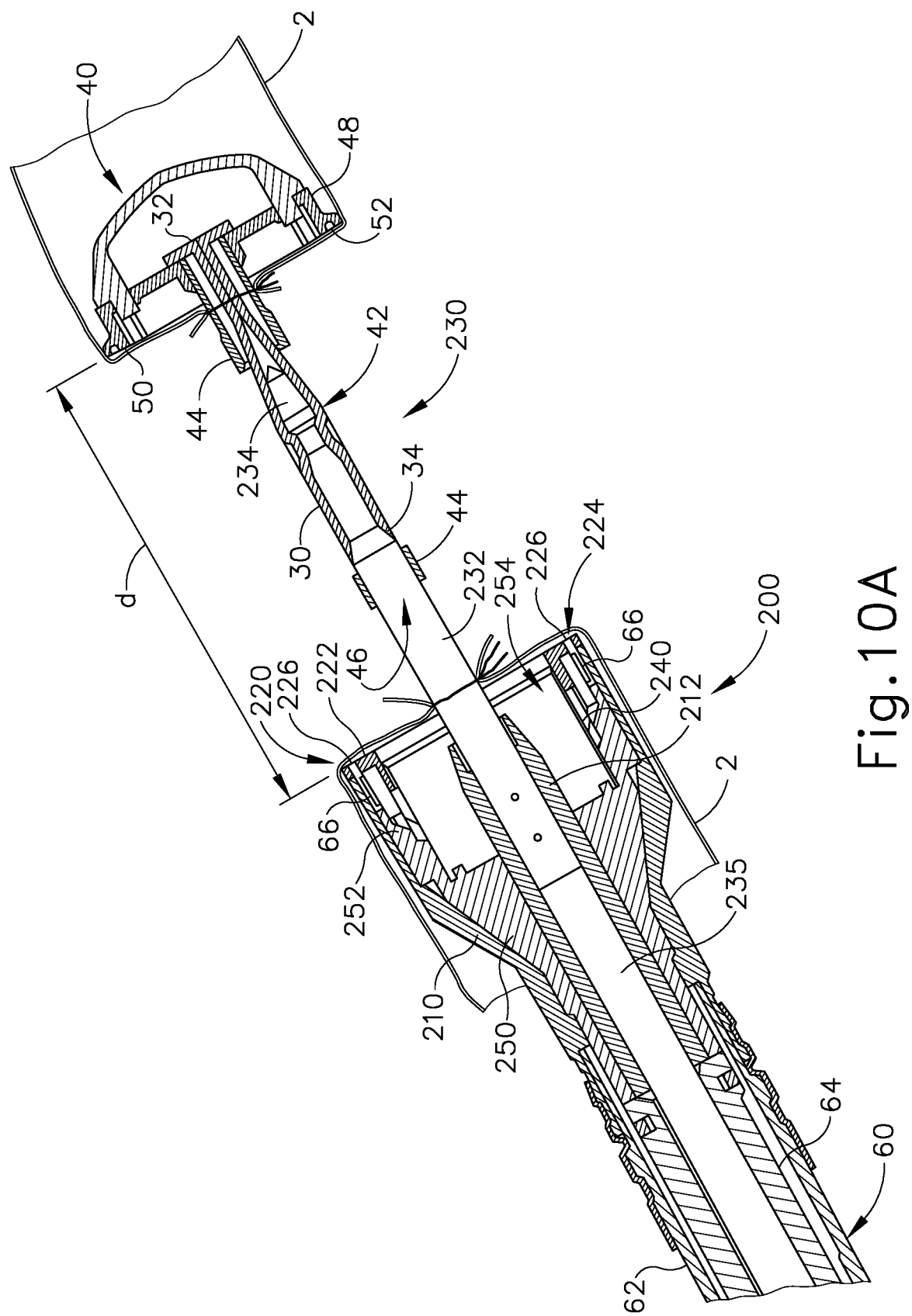
FIG. 10A depicts an enlarged longitudinal cross-section view of the stapling head assembly of FIG. 5, showing the anvil of FIG. 2 in a first open position, where the anvil is within a first tubular portion of tissue and the stapling head assembly is within a second tubular portion of tissue.
Figure 10B:
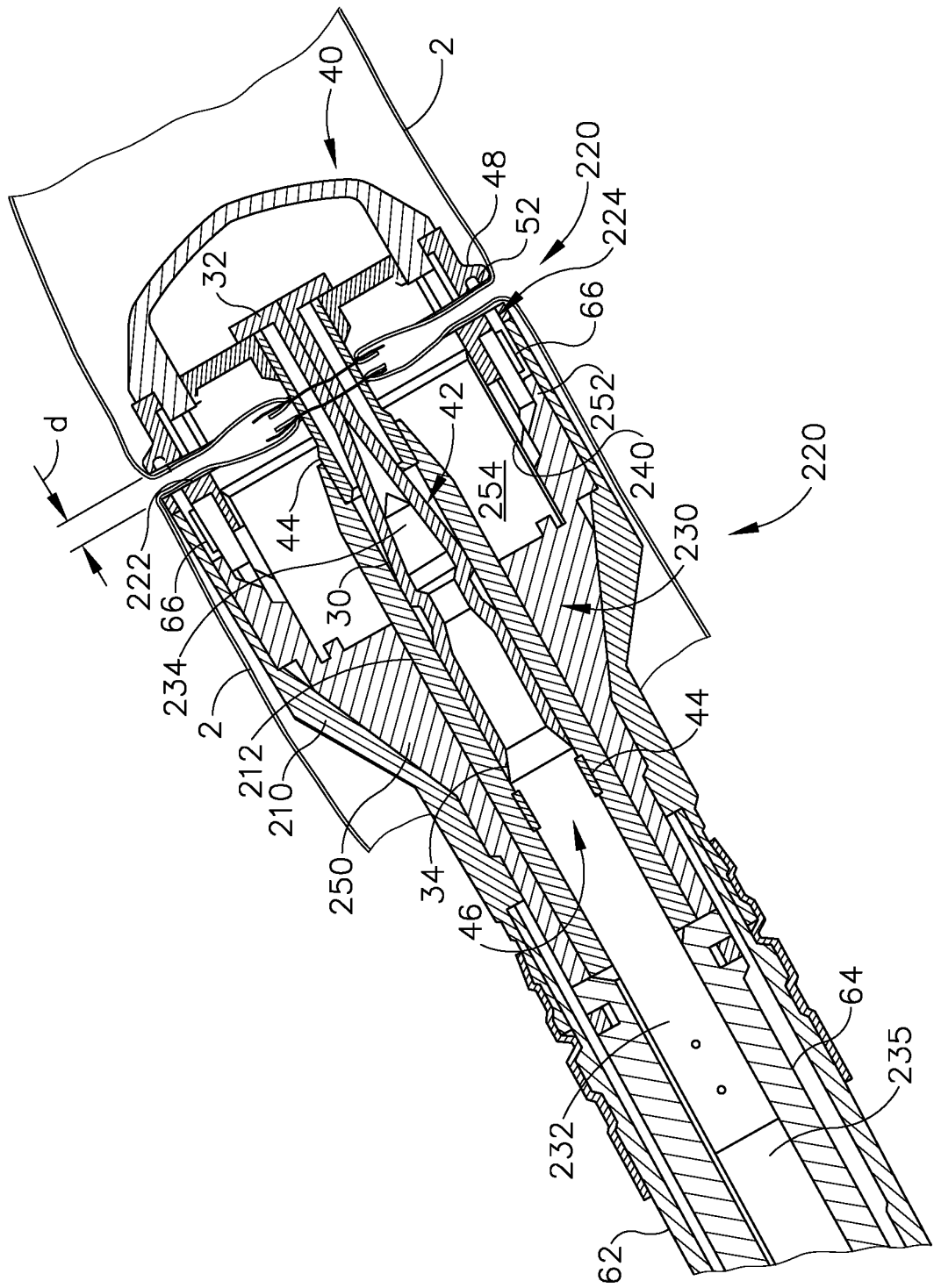
FIG. 10B depicts an enlarged longitudinal cross-sectional view of the stapling head assembly of FIG. 5, showing the anvil of FIG. 2 in a closed position, where the anvil is within the first tubular portion of tissue and the stapling head assembly is within the second tubular portion of tissue.

Staple driver member (250) is operable to actuate longitudinally within tubular casing (210) in response to rotation of trigger (74) of actuator handle assembly (70) as will be described in greater detail below. Staple driver member (250) includes two distally presented concentric annular arrays of staple drivers (252). Staple drivers (252) are arranged to correspond with the arrangement of staple forming pockets (52) described above. As best seen in FIGS. 10A-10B, each staple driver (252) is located underneath a corresponding staple (66). The arrangement of staple drivers (252) may be modified just like the arrangement of staple forming pockets (52) as described above. Staple driver member (250) also defines a bore (254) that is configured to coaxially receive core member (212) of tubular casing (210). An annular array of studs (256) project distally from a distally presented surface surrounding bore (254).

A cylindraceous knife member (240) is coaxially positioned within staple driver member (250). Knife member (240) includes a distally presented, sharp circular cutting edge (242). Knife member (240) is sized such that knife member (240) defines an outer diameter that is smaller than the diameter defined by the inner annular array of staple drivers (252). Knife member (240) also defines an opening that is configured to coaxially receive core member (212) of tubular casing (210). An annular array of openings (246) formed in knife member (240) is configured to complement the annular array of studs (256) of staple driver member (250), such that knife member (240) is fixedly secured to staple driver member (250) via studs (256) and openings (346). Therefore, when stapling driver member (250) is actuated relative to tubular casing (210), so is knife member (240). Other suitable structural relationships between knife member (240) and stapler driver member (250) will be apparent to those of ordinary skill in the art in view of the teachings herein.

A deck member (220) is fixedly secured to tubular casing (210). Deck member (220) includes a distally presented deck surface (222) defining two concentric annular arrays of staple openings (224), where each staple opening (224) has its own staple pocket (226) housing a staple (66). Staple openings (224) and staple pockets (226) are arranged to correspond with the arrangement of staple drivers (252) and staple forming pockets (52) described above. Accordingly, when staple driver member (250) is actuated distally relative to tubular casing (210) in response to rotation of trigger (74), each staple driver (252) drives a corresponding staple (66) out of its staple pocket (226) and through a corresponding staple opening (224) of deck member (220). When anvil (40) is in the closed position, staples (66) are driven into a corresponding staple forming pockets (52) to bend legs (68) of the staples (66), thereby stapling the material located between anvil (40) and stapling head assembly (200).

The arrangement of staple openings (224) may be modified just like the arrangement of staple forming pockets (52) as described above. It should also be understood that various structures and techniques may be used to contain staples (66) within stapling head assembly (200) before stapling head assembly (200) is actuated. Such structures and techniques that are used to contain staples within stapling head assembly (200) may prevent the staples from inadvertently falling out through staple openings (224) before stapling head assembly (200) is actuated. Various suitable forms that such structures and techniques may take will be apparent to those of ordinary skill in the art in view of the teachings herein.

As best seen in FIG. 5, deck member (220) defines an inner diameter that is just slightly larger than the outer diameter defined by knife member (240). Deck member (220) is thus configured to allow knife member (240) to translate distally to a point where cutting edge (242) is distal to deck surface (222).

In addition to or in lieu of the foregoing, stapling head assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pub. No. 2016/0374684, issued as U.S. Pat. No. 10,226,253 on Mar. 12, 2019, the disclosures of which are incorporated by reference herein. Still other suitable configurations will be apparent to one of ordinary skill in the art in view of the teachings herein.

C. Exemplary Shaft Assembly

Stapling head assembly (200) and trocar (230) are positioned at a distal end of shaft assembly (60), as shown in FIGS. 10A-10D. Shaft assembly (60) of the present example comprises an outer tubular member (62), a driver actuator (64), and connecting band portion (235). Outer tubular member (62) is coupled to tubular casing (210) of stapling head assembly (200) and to a body (72) of actuator handle assembly (70), thereby providing a mechanical ground for the actuating components therein. As seen in FIGS. 7A-7B, the proximal end of driver actuator (64) is coupled to a trigger actuation assembly (84) of actuator handle assembly (70), as described below. The distal end of driver actuator (64) is coupled to staple driver member (250) such that the rotation of trigger (74) longitudinally actuates staple driver member (250). As shown in FIGS. 10A-10D, driver actuator (64) comprises a tubular member having an open longitudinal axis such that trocar actuator (231) and connecting band portion (235), which are coupled to trocar (230), may actuate longitudinally within and relative to driver actuator (64). Other components may be disposed within driver actuator (64) as will be apparent to one of ordinary skill in the art in view of the teachings herein.

In the present example, shaft assembly (60) extends distally from actuator handle assembly (70) with a preformed bend. In some versions, the preformed bend is configured to facilitate positioning of stapling head assembly (200) within a patient's colon. Various suitable bend angles or radii that may be used will be apparent to those of ordinary skill in the art in view of the teachings herein. As mentioned above, actuator (231) is coupled with trocar (230) via flexible band portion (235). Flexible band portion (235) extends from a distal end of actuator (231), located proximal to the preformed bend, to couple with trocar (230), located distal to the preformed bend. Flexible band portion (235) may be dimensioned to flex during translation along the longitudinal profile of the preformed bend of shaft assembly (60). In such cases, trocar actuator (231) may be slidably housed within actuator handle assembly (70), while trocar (230) is slidably housed within tubular casing (210). Flexible band portion (235) may be connected to both trocar (230) and actuator (231) via pins or any other suitable means as would be apparent to one having ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pat. No. 9,936,949, the disclosures of which are incorporated by reference herein; and/or in accordance with other configurations as will be apparent to one of ordinary skill in the art in view of the teachings herein.

D. Exemplary Actuator Handle Assembly

Figure 12A:
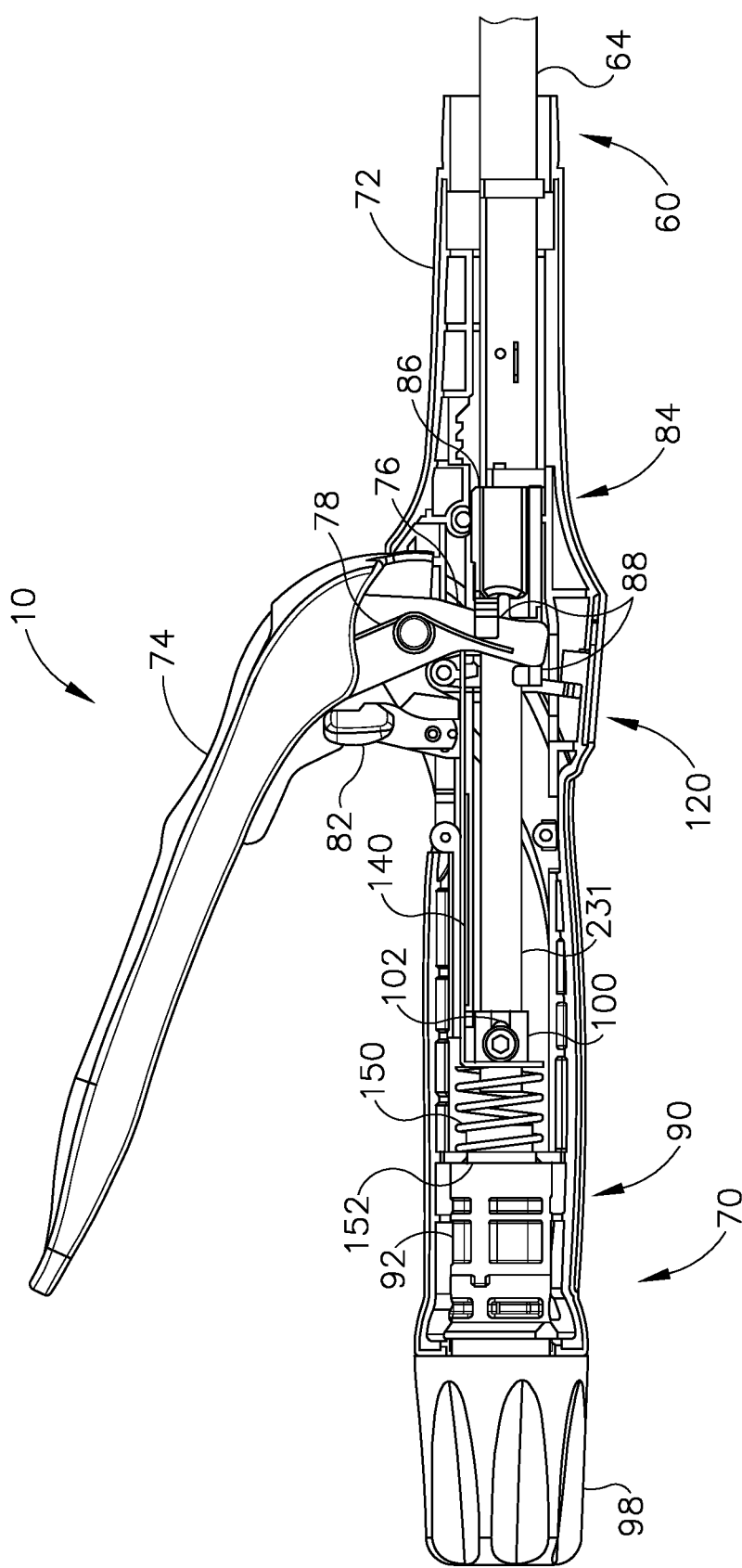
FIG. 12A depicts an enlarged side elevation view of an exemplary actuator handle assembly of the surgical instrument of FIG. 1 with a portion of the body removed, showing a trigger in an unfired position and a lockout feature in a locked position.

Referring now to FIGS. 6-8 and 12A-12B, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 12A) to a fired position (shown in FIG. 12B) actuates driver actuator (64) described above. A spring (78) is coupled to body (72) and trigger (74) to bias trigger (74) towards the unfired position. Lockout feature (82) is a pivotable member that is coupled to body (72). In a first, locked position, as shown in FIG. 12A, lockout feature (82) is pivoted upwards and away from body (72) such that lockout feature (82) engages trigger (74) and mechanically resists actuation of trigger (74) by a user. In a second, unlocked position, such as that shown in FIGS. 1 and 12B, lockout feature (82) is pivoted downward such that trigger (74) may be actuated by the user. Accordingly, with lockout feature (82) in the second position, trigger (74) can engage trigger actuation assembly (84) to fire instrument (10).

Figure 12B:
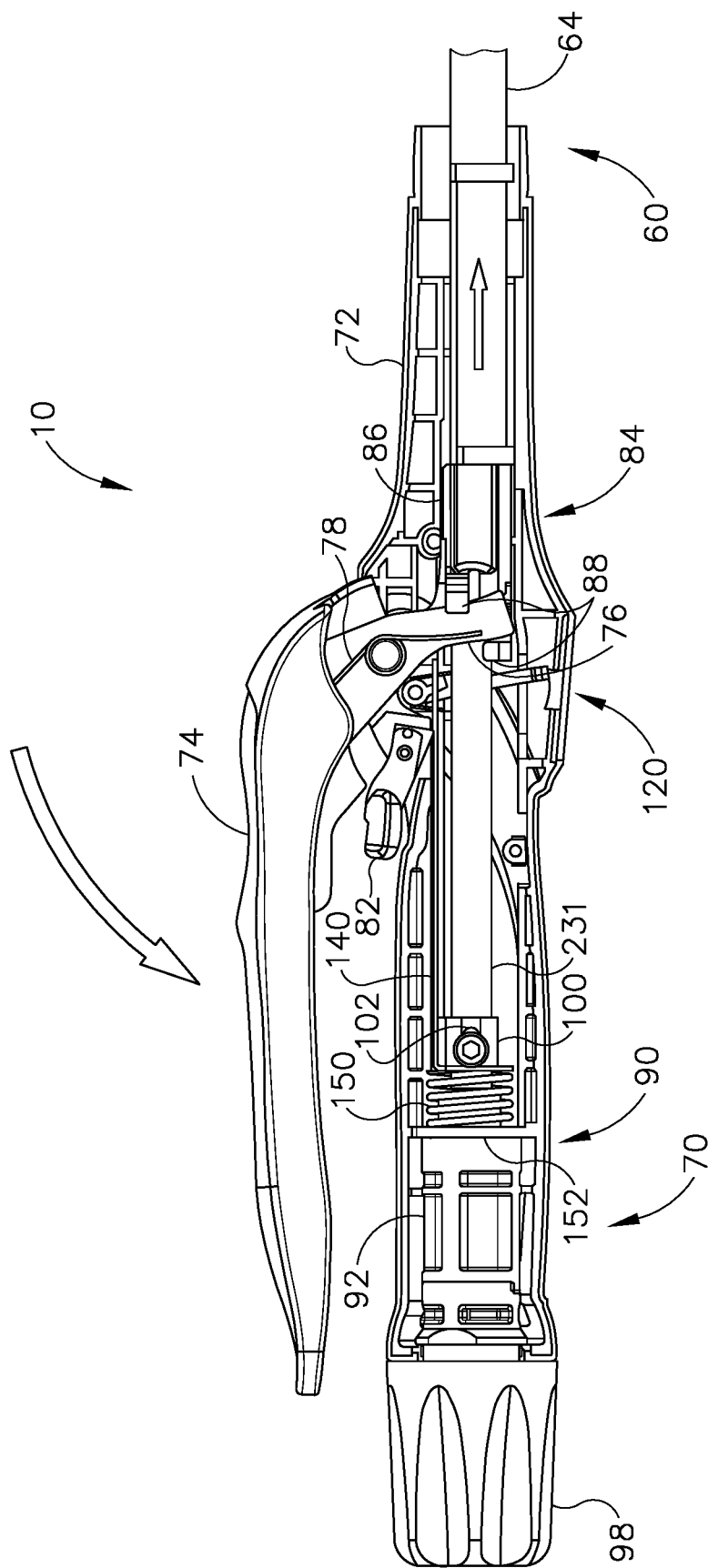
FIG. 12B depicts an enlarged side elevation view of the actuator handle assembly of FIG. 12A, showing the trigger in a fired position and the lockout feature in an unlocked position.

As shown in FIGS. 12A-12B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pat. No. 9,936,949 the disclosures of which are incorporated by reference herein; and/or in accordance with other configurations as will be apparent to one of ordinary skill in the art in view of the teachings herein.

Figure 6:
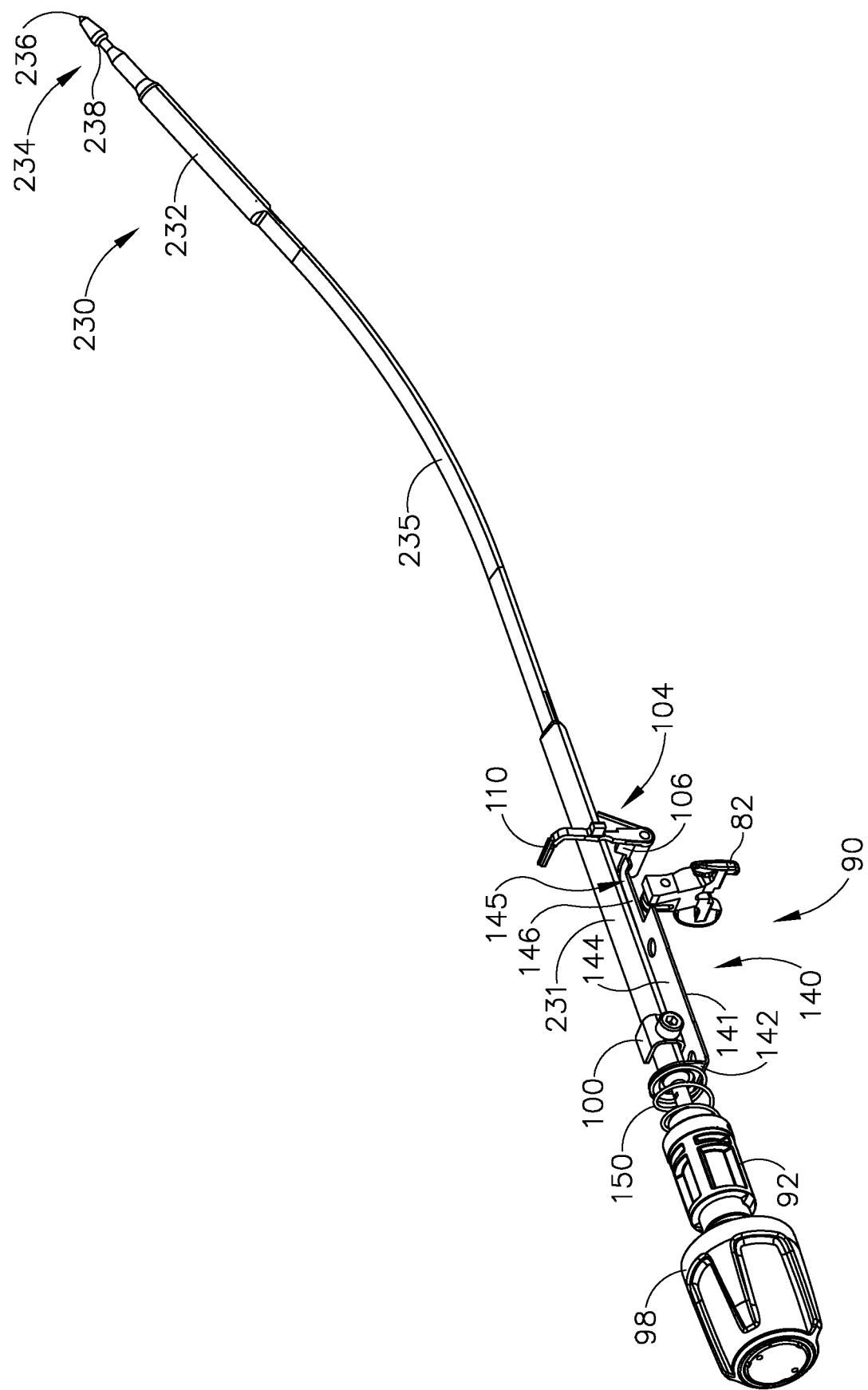
FIG. 6 depicts a perspective view of an exemplary closure system of the surgical instrument of FIG. 1.
Figure 7:
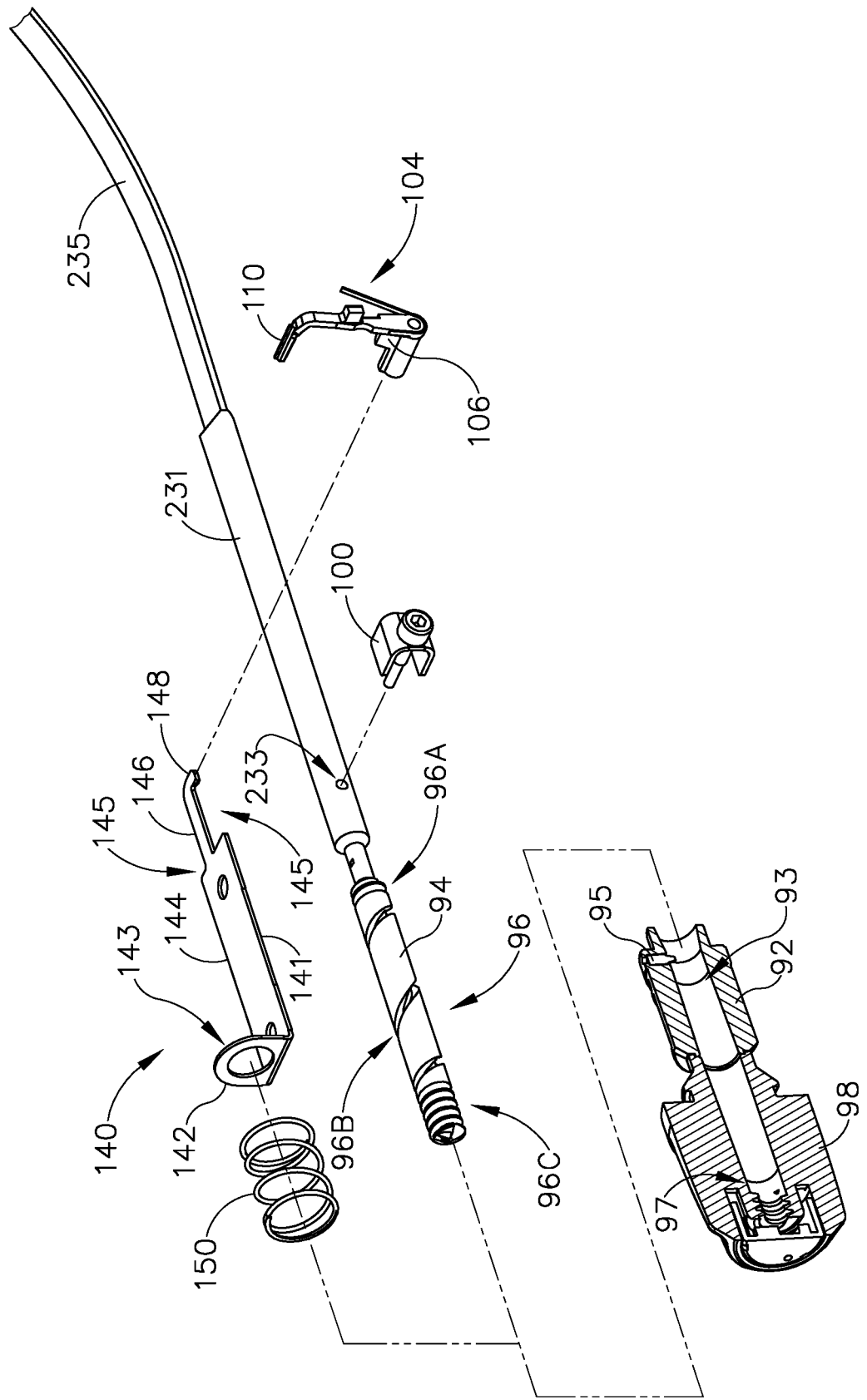
FIG. 7 depicts an exploded perspective view of the closure system of FIG. 1.

Body (72) also houses trocar actuation assembly (90) configured to actuate trocar (230) longitudinally in response to rotation of adjustment knob (98). As best shown in FIGS. 6-8, trocar actuation assembly (90) of the present example comprises adjustment knob (98), a grooved shank (94), and a sleeve (92). Grooved shank (94) is slidably housed within a channel (93) defined by both adjustment knob (98) and sleeve (92). Grooved shank (94) of the present example is located at a proximal end of trocar actuator (231). In other versions, grooved shank (94) and trocar actuator (231) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (95). Adjustment knob (98) also defines internal threading (97) as will be described in greater detail below. Grooved shank (94) of the present example comprises a continuous groove (96) formed in the outer surface of grooved shank (94). Accordingly, when adjustment knob (98) is rotated, internal tab (95) of sleeve (92) rides within groove (96) and grooved shank (94) is longitudinally actuated relative to sleeve (92). Since grooved shank (94) is located at the proximal end of trocar actuator (231), rotating adjustment knob (98) in a first direction advances trocar actuator (231) distally relative to actuator handle assembly (70). When trocar (230) is coupled with anvil (40), anvil (40) also advances distally relative to stapling head assembly (200) thereby increasing the distance between proximal surface (50) of the anvil (40) and distally presented deck surface (222) of deck member (220), otherwise known as a gap distance d. By rotating adjustment knob (98) in the opposite direction, trocar actuator (231) is actuated proximally relative to actuator handle assembly (70) to reduce the gap distance d between anvil (40) and stapling head assembly (200) when trocar (230) is coupled with anvil (40). Thus, trocar actuation assembly (90) is operable to actuate trocar (230) in response to rotating adjustment knob (98). Other suitable configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIGS. 7-8, distal portion (96A) comprises a fine pitch or a high number of grooves over a short axial length of grooved shank (94). Middle portion (96B) comprises a section with comparably coarser pitch or fewer grooves per axial length such that relatively few rotations are required for internal tab (95) of sleeve (92) to traverse along axial distance. When anvil (40) is in an initial, distal position in relation to stapling head assembly (200) (as shown in FIG. 10A) the internal tab (95) of sleeve (92) is positioned in middle portion (96B). Accordingly, the gap distance d may be quickly reduced through relatively few rotations of adjustment knob (98) while the internal tab (95) of sleeve (92) traverses middle portion (96B). Proximal portion (96C) of the present example is substantially like distal portion (96A) and comprises a fine pitch or a high number of grooves over a short axial distance of grooved shank (94) such that many rotations are required to traverse the short axial distance. Proximal portion (96C) of the present example is engaged by the internal threading (97) defined by knob (98) when anvil (40) is substantially near to stapling head assembly (200) (as shown in FIG. 10B), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages internal threading (97) of knob (98), each rotation of adjustment knob (98) may reduce the gap distance d by a relatively small amount to provide for fine tuning. Internal tab (95) of sleeve (92) may be disengaged from groove (96) when proximal portion (96C) is engaged with internal threading (97) of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 9,936,949 the disclosures of which are incorporated by reference herein; and/or in accordance with other configurations as will be apparent to one of ordinary skill in the art in view of the teachings herein.

As noted above, gap distance d corresponds to the distance between anvil (40) and stapling head assembly (200). When instrument (10) is inserted into a patient, this gap distance d may not be easily viewable. Accordingly, a moveable indicator bar (110), shown in FIGS. 8-9, is provided to be visible through an indicator window (120) positioned opposite to trigger (74). As will be described in greater detail below, indicator bar (110) is operable to move in response to rotation of adjustment knob (98) such that the position of indicator bar (110) is representative of the gap distance d. As shown in FIG. 9, indicator window (120) further comprises a scale (130) which indicates that the anvil gap is within a desired operating range (e.g., a green colored region or "green zone") and a corresponding staple compression representation at each end of scale (130). By way of example only, as shown in FIG. 9, a first staple image (132) depicts a large staple height while a second staple image (134) depicts a small staple height. Accordingly, a user can view the position of the coupled anvil (40) relative to the stapling head assembly (200) via indicator bar (110) and scale (130). The user may then adjust the positioning of anvil (40) via adjustment knob (98) accordingly.

In the example shown in FIGS. 6-8, a U-shaped clip (100) is attached to an intermediate portion of trocar actuator (231) via a through hole (233) located distally of grooved shank (94). In the present example, an extension of trocar actuator (231) engages a slot in the housing of handle assembly (70) to prevent trocar actuator (231) from rotating about its axis when adjustment knob (98) is rotated. It may be necessary to calibrate the proper placement of trocar actuator (231) within instrument (10) such that indicator bar (110) may show a proper gap distance d during exemplary use. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (231) for purposes of calibrating indicator bar (110) relative to scale (130). In some versions, the attachment member (e.g., screw, bolt, pin, etc.) engages with a portion of body (72) to substantially prevent trocar actuator (231) from rotating about its axis when adjustment knob (98) is rotated.

As shown in FIGS. 6-8, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (143) to slidably mount onto trocar actuator (231) and/or grooved shank (94). A coil spring (150) is interposed between flange (142) and a boss (152) of body (72) to bias flange (142) against U-shaped clip (100). Accordingly, when U-shaped clip (100) actuates distally with trocar actuator (231) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (231) and/or grooved shank (94) translate proximally, thereby compressing coil spring (150). In some versions, indicator bracket (140) may be fixedly attached to trocar actuator (231) and/or grooved shank (94).

In the present example, a portion of lockout feature (82) abuts a surface (141) of indicator bracket (140) when indicator bracket (140) is in a longitudinal position that does not correspond to when gap distance d is within a desired operating range (e.g., a green colored region or "green zone"). When gap distance d is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 7, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 9) to show the relative gap distance d between proximal surface (50) of anvil (40) and distally presented deck surface (222) of deck member (220).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847; and/or U.S. Pat. No. 9,936,949 the disclosures of which are incorporated by reference herein; and/or in accordance with other configurations as will be apparent to one of ordinary skill in the art in view of the teachings herein.

E. Exemplary Use of Circular Stapling Surgical Instrument

FIGS. 12A-12B and FIGS. 10A-10E show an exemplary use of circular stapling surgical instrument (10) in accordance with the description above. As mentioned above, anvil (40) may selectively couple with trocar (230) such that movement of trocar (230) relative to tubular casing (210) and deck member (220) leads to movement of anvil (40) relative to tubular casing (210) and deck member (220). With anvil (40) as a separate component, it should be understood that anvil (40) may initially be inserted and secured to a portion of tissue (2) prior to being coupled with trocar (230). By way of example only, anvil (40) may be inserted into and secured to a first tubular portion of tissue (2) while stapling head assembly (200) is inserted into and secured to a second tubular portion of tissue (2). For instance, the first tubular portion of tissue (2) may be sutured to or about a portion of anvil (40), and the second tubular portion of tissue (2) may be sutured to or about trocar (230).

As shown in FIG. 10A, anvil (40) may then be coupled to trocar (230) in accordance with the description above, such as a snap fitting between latch members (30) of anvil (40) and head (234) of trocar (230). In FIG. 10A, trocar (230) is shown in a distal most actuated position. Trocar (230) may be actuated to the distal most actuated position by rotation of knob (98) in accordance with the description above. Such an extended position for trocar (230) may provide a larger area to which tissue (2) may be coupled prior to attachment of anvil (40). The extended position of trocar (230) may also provide for easier attachment of anvil (40) to trocar (230). At the position shown in FIG. 10A, trigger (74) is locked in the position shown in FIG. 7A by lockout feature (82), as lockout feature (82) may not pivot to unlock trigger (74) due to interference caused by surface (141) of indicator bracket (140) in accordance with the description above.

As mentioned above, when anvil (40) is coupled to trocar (230), rotation of adjustment knob (98) may translate both trocar (230) and anvil (40), thereby enlarging or reducing gap distance d. For instance, as shown sequentially in FIGS. 10A-10B, anvil (40) is shown actuating proximally relative to actuator handle assembly (70) from an initial, open position (FIG. 10A) to a closed position (FIG. 10B) where gap distance d is brought within a suitable predetermined range. It should be understood that in the position shown in FIG. 10A, grooved shank (94) is in a distal position where the middle portion (96B) of groove (96) engages internal tab (95) of sleeve (92).

When gap distance d is brought within a suitable predetermined range, indicator bar (110) may move within indicator window (120) to show the relative gap distance d is within a desired operating range (e.g. a green colored region or "green zone") in accordance with the description above. Likewise, it should be understood that in the position shown in FIG. 10B, grooved shank (94) is in a proximal position where the proximal portion (96C) of groove (96) engages internal threading (97) of knob (98). Therefore, each rotation of adjustment knob (98) may reduce the gap distance d by a relatively small amount to provide for fine tuning.

Figure 10C:
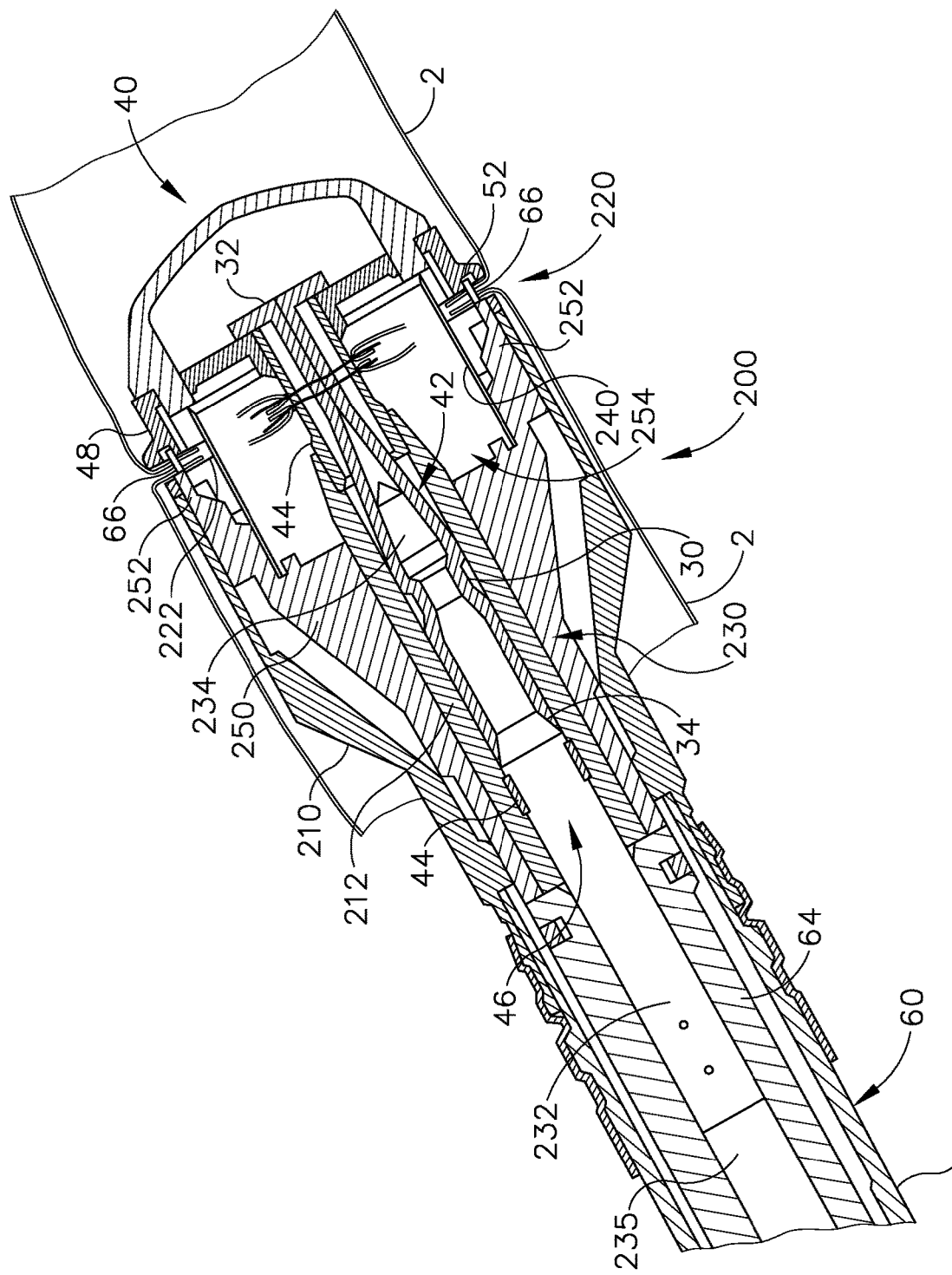
FIG. 10C depicts an enlarged longitudinal cross-sectional view of the stapling head assembly of FIG. 5, showing the anvil of FIG. 2 in the closed position, were an exemplary staple driver and blade are in a fired position such that the first tubular portion of tissue and the second tubular portion of tissue are stapled together with excess tissue severed.

As shown between FIGS. 12A-12B, when gap distance d is brought within a suitable predetermined range, lockout feature (82) may be pivoted relative to body (72) to an unlocked position such that trigger (74) may pivot relative to body (72) to engage trigger actuation assembly (84) in accordance with the description above. As shown in FIG. 12B, with lockout feature (82) pivoted into the unlocked position, trigger (74) is pivoted toward body (72) such that trigger arms (76) drive against tabs (88) to distally actuate slidable trigger carriage (86) and driver actuator (64). As shown in FIG. 10C, distal actuation of driver actuator (64) drives slidable staple driver member (250), staples drivers (252), and cylindraceous knife member (240) distally. Distal advancement of staple drivers (252) drive staples (66) against corresponding staple forming pockets (52) thereby stapling tissue (2) between anvil (40) and stapling head assembly (200) to form a continuous tubular portion of tissue (2). Additionally, distal advancement of cylindraceous knife member (240) severs excess tissue located radially interior to newly formed staples (66). Stapling head assembly (200) is operable to staple and sever tissue (2) by a user pivoting a trigger (74) of actuator handle assembly (70), as will be described in greater detail below.

Figure 10D:
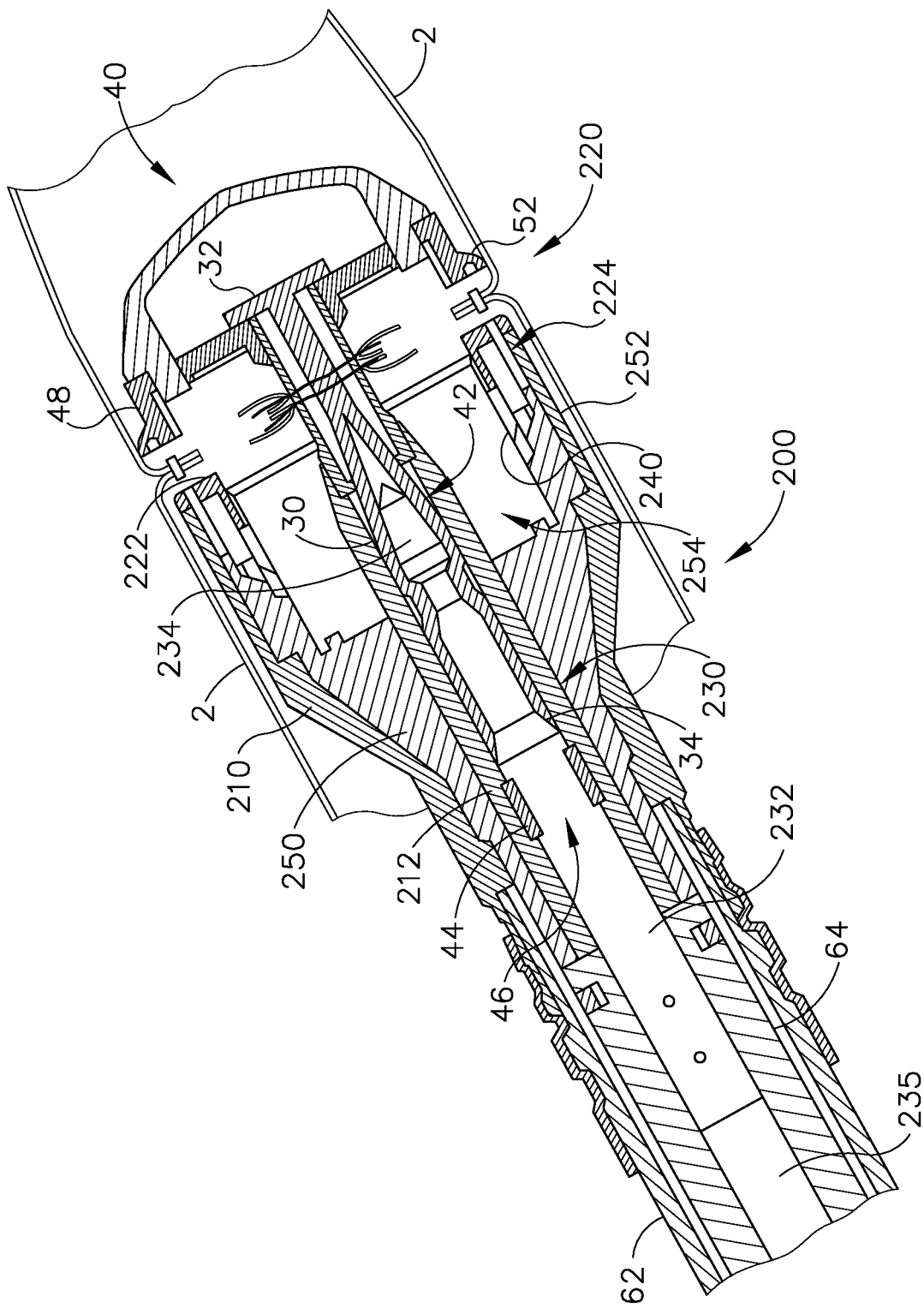
FIG. 10D depicts an enlarged longitudinal cross-sectional view of the stapling head assembly of FIG. 5, showing the anvil of FIG. 2 in a second open position, where the first tubular portion of tissue and the second tubular portion of tissue are attached.

As best shown in FIG. 10D, once trigger (74) has been actuated to staple and sever tissue (2), a user may then turn rotatable knob (98) to distally advance anvil (40), thereby releasing portions of tissue (2) grasped between proximal surface (50) of anvil (40) and distally presented deck surface (222) of deck member (220). As best shown in FIG. 10E, with previously grasped tissue (2) released, a user may then remove instrument (10), thereby leaving a continuous tubular portion of tissue (2) behind.

II. Exemplary Dual Stage Closure Systems for Circular Stapling Surgical Instrument As mentioned above, adjustment knob (98) and sleeve (92) are configured to rotate relative to body (72) in order to translate grooved shank (94), thereby moving trocar actuator (231), connecting band portion (235), trocar (230). As also mentioned above, grooved shank (94) defines a continuous groove (96) having a plurality of portions (96A, 96B, 96C) with varying pitches or number of grooves per axial distance. In particular, middle portion (96B) includes a coarse pitch or fewer grooves per axial length and is configured to mesh with internal tab (95) of sleeve (92); while distal portion (96A) and proximal portion (96C) include a fine pitch or high number of grooves over a short axial distance and are configured to mesh with internal tab (95) and internal threading (97), respectively. Therefore, when trocar (230) is coupled with anvil (40) in accordance with the description above, gap distance d may be quickly reduced through relatively few rotations of adjustment knob (98) while the internal tab (95) of sleeve (92) traverses middle portion (96B) of continuous groove (96). Once internal tab (95) no longer engages middle portion (96B) of continuous groove (96), proximal portion (96C) of groove (96) engages internal threading (97) of knob (98) such that rotation of adjustment knob (98) in the same direction may reduce the gap distance d by a relatively small amount to provide for fine tuning. In other words, gap distance d may be reduced at a relatively fast rate through a first range of rotary motion of knob (98); then at a relatively slow rate through a second range of rotary motion of knob (98).

Quick reduction of gap distance d may be desirable when trocar (230) initially couples with anvil (40) in an open position in order to quickly actuate anvil (40) toward a position within the desired operating range (e.g., a green colored region or "green zone"). Fine tuning of gap distance d may be desirable when anvil (40) has entered, or is about to enter, the desired operating range (e.g., a green colored region or "green zone"). In other words, as shown in FIG. 9, a smaller deviation of gap distance d may be desirable when gap distance d is visualized via the position of indicator bar (110) on scale (130) between the large staple height compression (i.e. a "high B" staple formation) depicted by first staple image (132) and the small staple height compression (i.e. a "low B" staple formation) represent by second staple image (134); while a larger deviation of gap distance d may be desirable to quickly actuate anvil (40) between the open position and a position near to where gap distance d is visualized via the position of indicator bar (110) on scale (130) at the large staple height compression depicted by first staple image (132).

Those of ordinary skill in the art will recognize that an appropriate gap distance d may be particularly critical to the success of an anastomosis. It may therefore be critical for the operator to be assured that the gap distance d is consistently and precisely achieved in accordance with the operator's expectations based on the angular position of adjustment knob (98); and based on the accuracy of indicator bar (110) displaying gap distance d. In some instances, gap distance d may be within the desired operating range, but near the large staple height compression such that further distal movement of trocar (230) may actuate anvil (40) to a position where gap distance d is out of the desired operating range. Additionally, grooved shank (94) may be close to a position where proximal portion of groove (96C) disengages internal threading (97) such that internal tab (95) engages middle portion of groove (96B). If this occurs, the operator may rotate adjustment knob (98) expecting to finely tune gap distance d with small movement within the desired operating range, but instead may quickly actuate gap distance d through larger movement out of the desired operating range.

In other words, the operator may expect angular displacement of adjustment knob (98) to result in trocar (230) to move a first distance, but instead that same angular displacement of adjustment knob (98) moves trocar (230) an unexpected greater distance. Unexpected greater movement may cause gap distance d to move out of, or even further out of, the desired operating range, which may adversely affect the success of an anastomosis.

Therefore, instead of having rotation of adjustment knob (98) result in both larger movement and smaller movement of trocar (230), it may be desirable to provide a trocar actuation assembly with a dual stage closure system having distinguishable driving motions for larger movement of trocar (230) and a smaller, more finely tuned, movement of trocar (230). The following are various examples of trocar actuation assemblies that provide for both smaller, more finely tuned movement of trocar (230), as well as larger, more coarse movement of trocar (230).

Figure 13A:
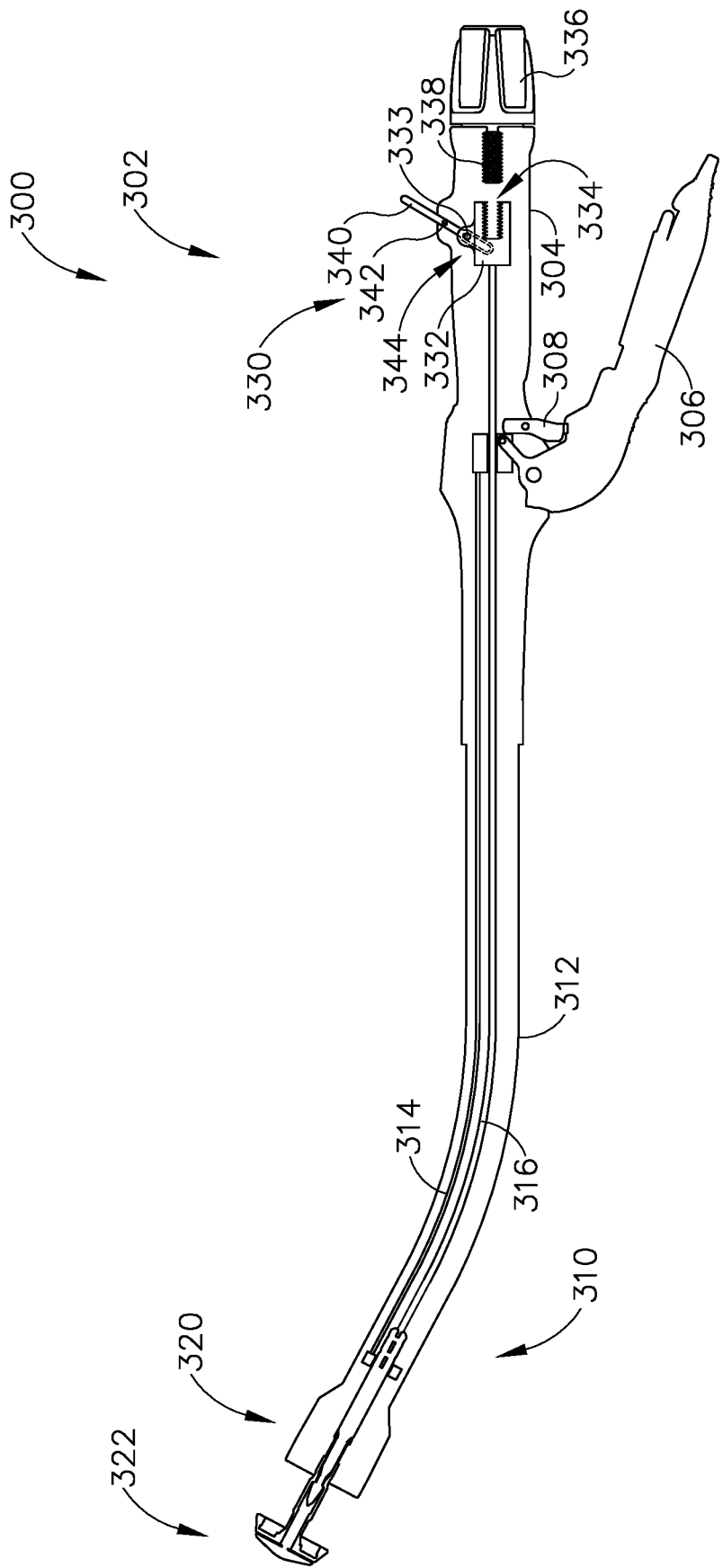
FIG. 13A depicts a cross-sectional side view of an alternative circular stapling surgical instrument, wherein a trocar actuation assembly is in a first configuration associated with an anvil in an open position.
Figure 13B:
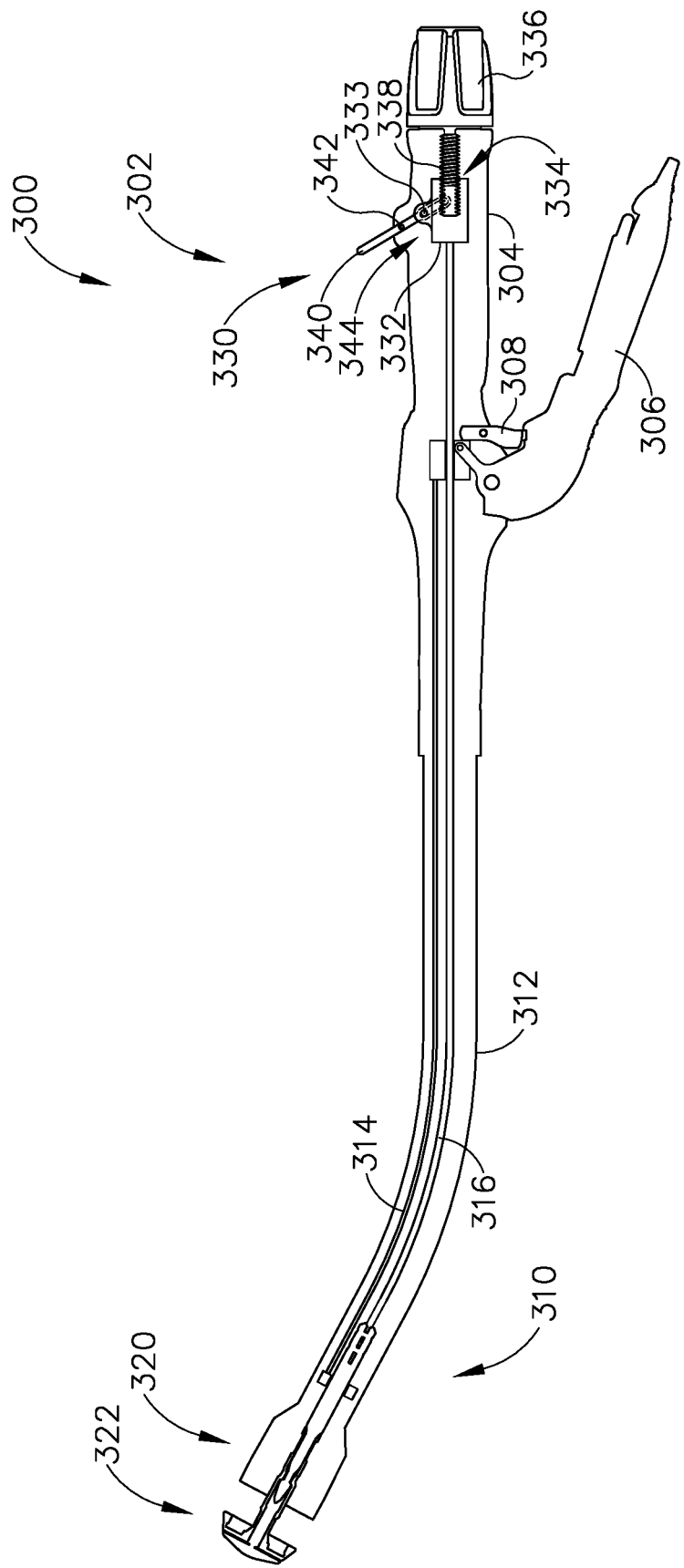
FIG. 13B depicts a cross-sectional side view of the circular stapling surgical instrument of FIG. 13A, where the trocar actuation assembly is in a second configuration associated with the anvil in a first closed position.
Figure 13C:
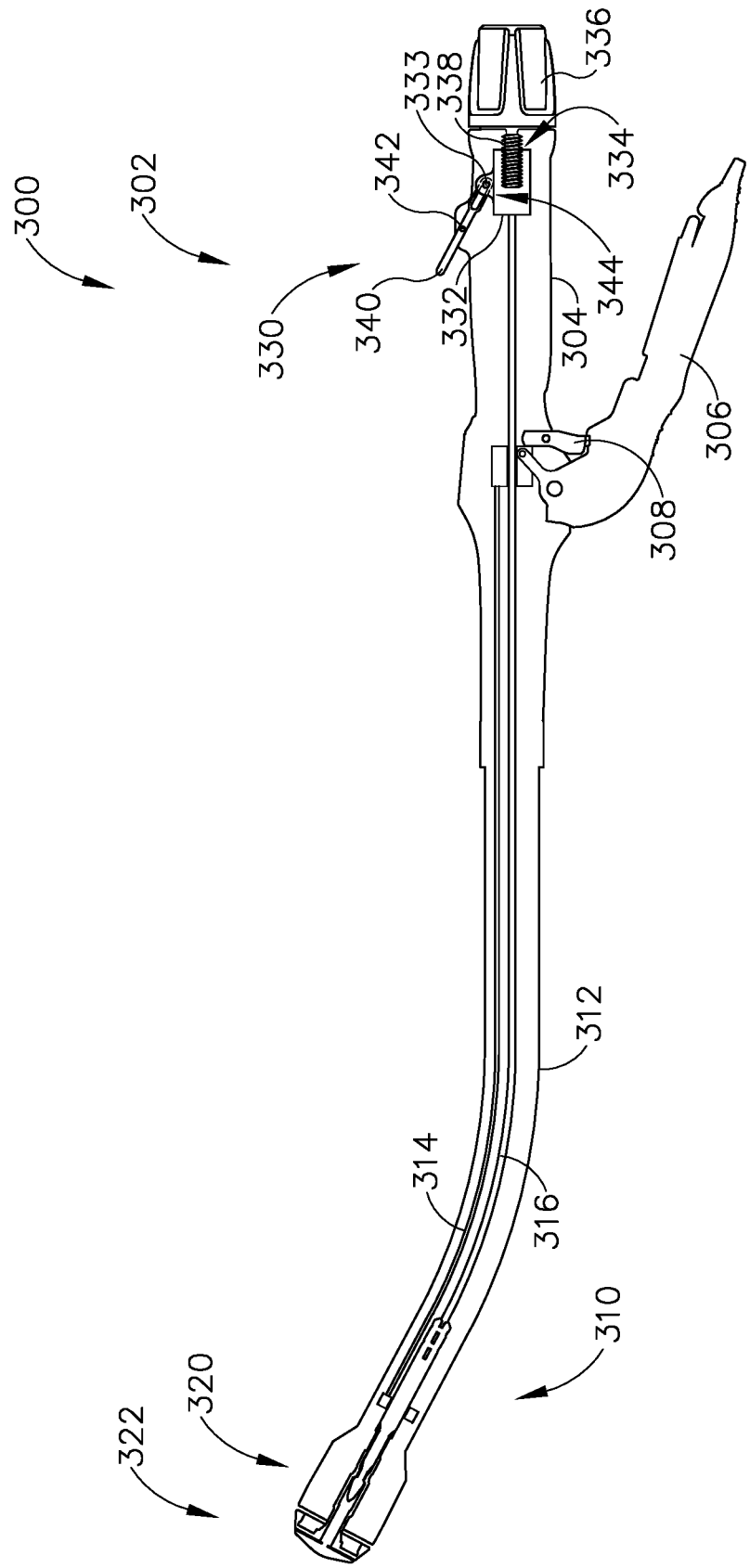
FIG. 13C depicts a cross-sectional side view of the circular stapling surgical instrument of FIG. 13A, where the trocar actuation assembly is in a third configuration associated with the anvil in a second closed position.

A. Exemplary Dual Stage Trocar Actuation Assemblies Multiple Input Actuation Mechanisms FIGS. 13A-13C show an alternative exemplary circular surgical stapling instrument (300). While not explicitly described below, instrument (300) may have various features and functionality described above for instrument (10). Therefore, instrument (300) is substantially similar to instrument (10) described above, with differences elaborated below. Instrument (300) includes an actuator handle assembly (302), a shaft assembly (310), a staple head assembly (320), and an anvil (322); which are substantially similar to actuator handle assembly (70), shaft assembly (60), staple head assembly (200), and anvil (40) described above, respectively, with differences elaborated below.

Actuator handle assembly (302) includes a body (304), a trigger (306), and a lockout feature (308), which are substantially similar to body (72), trigger (74), and lockout feature (82) described above, respectively, with differences elaborated below. Additionally, actuator handle assembly (302) includes a dual stage trocar actuation assembly (330). As will be described in greater detail below, trocar actuator assembly (330) is configured to actuate a trocar (316), while coupled with anvil (322), from an open position toward a first closed position utilizing a pivot handle (340). Additionally, trocar actuator assembly (330) is configured to actuate trocar (316), while coupled with anvil (322), between the first closed position and a second closed position utilizing an adjustment knob (336).

Shaft assembly (310) includes an outer tubular member (312), a driver actuator (314), and a trocar (316), which are substantially similar to outer tubular member (62), driver actuator (64), and trocar (230) described above, respectively. While not explicitly shown, trocar (316) may include features similar to trocar actuator (231) and connecting band portion (235) described above. Driver actuator (314) extends between staple head assembly (320) and trigger (306) such that trigger (306) may pivot toward body (304) in order to fire staple head assembly (320) to simultaneously staple and sever tissue suitably captured between anvil (322) and staple head assembly (320) in accordance with the teachings herein.

Trocar actuation assembly (330) includes a proximal frame (332), adjustment knob (336), a threaded rod (338), and pivot handle (340). As mentioned above, and as will be described in greater detail below, pivot handle (340) is configured to actuate trocar (316) between an open position and a first closed position, while adjustment knob (336) and threaded rod (338) are configured to actuate trocar (316) from the first closed position further toward the second closed position.

It should be understood that in the open position, a distal end of trocar (316) may extend distally past staple head assembly (320) such that trocar (316) may suitably couple with anvil (322) in accordance with the teachings herein. The first closed position may correspond to a gap distance d between anvil (322) and staple head assembly (320) such that if driver actuator (314) is fired is accordance with the teachings herein, staples (66) will form a suitable large staple height compression. Alternatively, the first closed position may correspond to a gap distance d between anvil (322) and staple head assembly (320) such that anvil (322) is slightly distal compared to the position required for staples (66) to form a suitable large staple height compression. In such instances, the operator may be required to proximally actuate trocar (316) and anvil (322) from the first closed position utilizing adjustment knob (336) and threaded rod (338) to achieve a suitable gap distance d corresponding with a large staple height compression. The second closed position may correspond to a gap distance d between anvil (322) and staple head assembly (320) such that if driver actuator (314) is fired in accordance with the teachings herein, staples (66) will form a suitable small staple height compression.

Proximal frame (332) is attached to a proximal end of trocar (316) such that movement of proximal frame (332) results in movement of trocar (316). Proximal frame (332) is slidably disposed within body (304) such that proximal frame (332) may translate relative to body (304). However, proximal frame (332) is rotationally fixed within body (304) such that proximal frame (332) may not rotate about its own longitudinal axis. Proximal frame (332) may be rotationally fixed and slidably coupled with body (304) via a pin and slot relationship, or any other suitable coupling that would be apparent to one of ordinary skill in the art in view of the teachings herein. Proximal frame (332) includes a transverse projection (333) slidably housed within a slot (344) defined by pivot handle (340). Additionally, proximal frame (332) defines a threaded channel (334) dimensioned to selectively receive and mesh with threaded rod (338).

Pivot handle (340) is pivotably coupled with body (304) via pivot pin (342). Pivot handle (340) is configured to actuate trocar (316), and anvil (322) when suitably coupled to trocar (316), between the open position and the first closed position. A first portion of pivot handle (340) extends away from body (304), while a second portion of pivot handle (340) extends within body (304). The first portion of pivot handle (340) is dimensioned to be grasped by the operator. The second portion of pivot handle (340) extending within handle defines slot (344) that slidably houses transverse projection (333) of proximal frame (332).

When the operator wishes to actuate trocar (316) from the open position (as shown in FIG. 13A) toward the first closed position (as shown in FIG. 13B), the operator may grasp the first portion of pivot handle (340) and push the first portion of pivot handle (340) distally. As the first portion of pivot handle (340) pivots distally, the second portion of pivot handle (340) pivots proximally. Because transverse projection (333) is slidably housed within slot (344) of pivot handle (340), the second portion of pivot handle (340) drives proximal frame (332), and therefore trocar (316), proximally toward the first closed position. The length of slot (344) is dimensioned such that as pivot handle (340) travels in an arched motion, proximal frame (332) is permitted to travel in a substantially linear motion through the entire range or motion of trocar (316) (i.e. from the open position all the way to the second closed position). If the operator desires to actuate trocar (316) from the first closed position back into the open position, the operator may simply pivot the first portion of handle (340) proximally in order to drive proximal frame (332) and trocar (316) distally in accordance with the description herein.

Adjustment knob (336) is rotationally disposed on the proximal end of body (304). Therefore, adjustment knob (336) may rotate relative to body (304), similar to the relationship between adjustment knob (98) and body (72) described above. Threaded rod (338) extends distally from adjustment knob (336) into the interior of body (304). Threaded rod (338) is attached to adjustment knob (336) such that rotation of adjustment knob (336) causes rotation of threaded rod (338).

As mentioned above, threaded rod (338) is dimensioned to suitably mesh with threaded channel (334) of proximal frame (332). As shown in FIG. 13B, when proximal frame (332) is actuated by pivot handle (340) to the position where trocar (316) is in the first closed position, a distal end of threaded rod (338) is directly adjacent to, and aligned with, a proximal end of threaded channel (334). At this moment, threaded rod (338) would prevent further proximal translation of proximal frame (332) via further pivoting of handle (340). Instead, as shown between FIGS. 13B and 13C, if the operator desires to actuate proximal frame (332) further proximally such that trocar (316) actuates between the first closed position and the second closed position, the operator may rotate adjustment knob (336) in a first angular direction until a distal end of threaded rod (338) catches into engagement with thread channel (334) such that threaded rod (338) and threaded channel (334) begin to mesh.

Because proximal frame (332) is slidably housed and rotationally constrained within body (304), when threaded rod (338) meshes with threaded channel (334), rotation of threaded rod (338) drives translation of proximal frame (332), and therefore drives translation of trocar (316). Therefore, as shown in FIG. 13C, the operator may rotate adjustment knob (336) in the first angular direction to urge proximal frame (332) and trocar (316) proximally toward the second closed position. Conversely, the operator may rotate adjustment knob (336) in the second angular direction to urge proximal frame (332) and trocar (316) distally toward the first closed position. If the operator accidentally rotates adjustment knob (336) in the second angular direction such that proximal frame (332) and trocar (316) reach the first closed position, threaded rod (338) and threaded channel (334) will no longer mesh. Therefore, further rotation of adjustment knob (336) in the second angular direction while trocar (316) is in the first closed position will no longer actuate proximal frame (332) or trocar (316) in the distal direction.

It should be understood that in instances where the first closed position corresponds to a gap distance d between anvil (322) and staple head assembly (320) such that anvil (322) is slightly distal compared to the position required for staples (66) to form a suitable large staple height compression, threaded rod (338) and threaded channel (334) mesh when anvil (322) and staple head (320) assembly define a suitable gap distance d for a large staple height compression.

In the current example, threaded rod (338) and threaded channel (334) are used to convert rotational movement of adjustment knob (336) into translational movement of proximal frame (332). However, this is merely optional, as any suitable mechanism to convert rotational movement into translational movement, or vice versa, may be used as would be apparent to one having ordinary skill in the art in view of the teachings herein. For example, a threadless rod and rolling ring bearing assembly may be used.

Figure 14A:
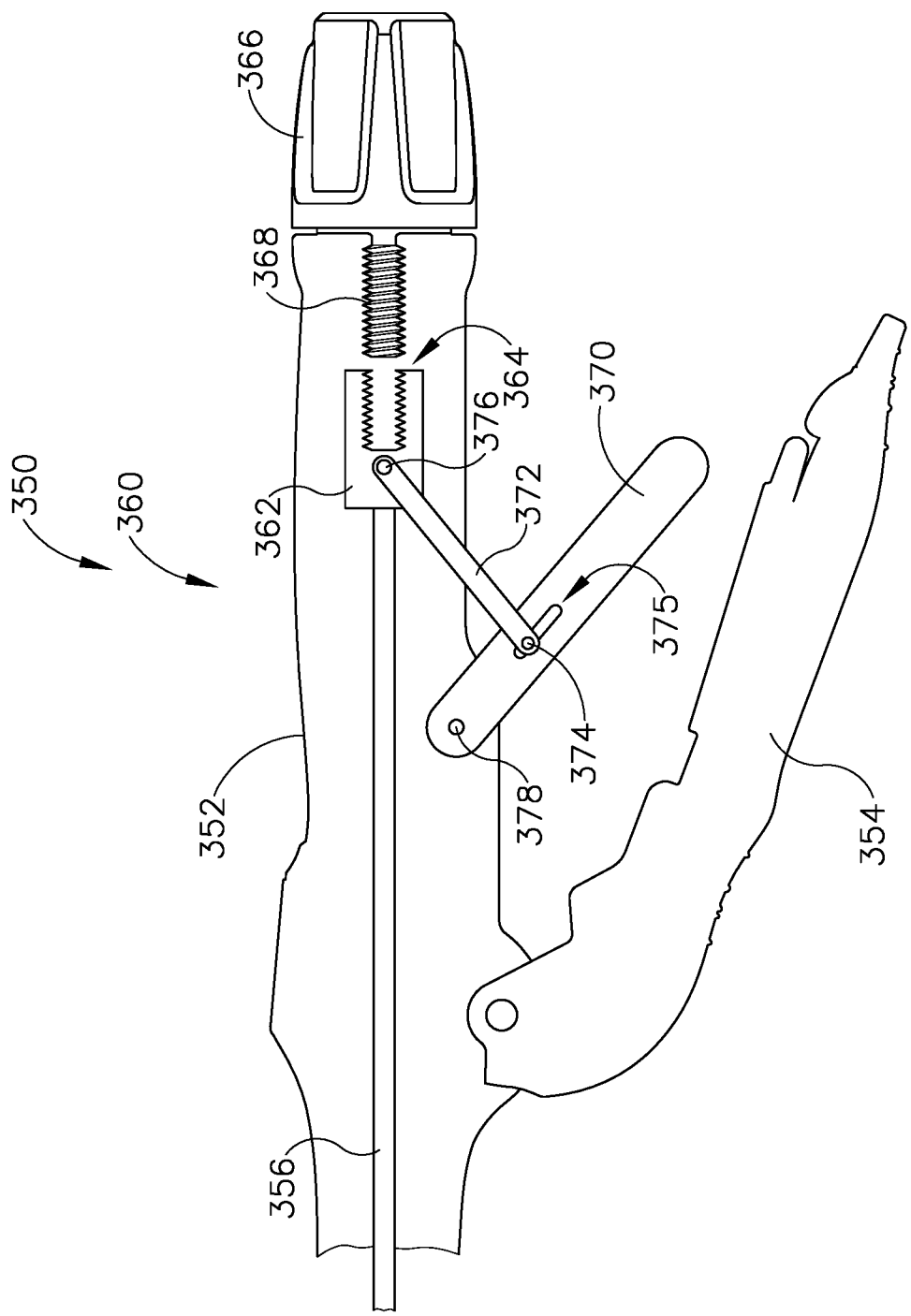
FIG. 14A depicts a cross-sectional side view of an alternative actuator handle assembly that may be readily incorporated into the circular stapling surgical instrument of FIG. 1 or 13A, where a trocar actuation assembly is in a first configuration associated with an anvil in an open position.

FIGS. 14A-15 show an alternative actuator handle assembly (350) that may be readily incorporated into instruments (10, 300) described above. While not explicitly described below, actuator handle assembly (350) may have various features and functionality described above for actuator handle assemblies (70, 302) described above. Actuator handle assembly (350) includes a body (352) and a trigger (354), which are substantially similar to body (72) and trigger (74) described above, respectively. Additionally, actuator handle assembly (350) includes a dual stage trocar actuation assembly (360).

An elongated coupling member in the form of a trocar (356) extends proximally within body (352). Trocar (356) may be substantially similar to trocar (230) described above, with differences elaborated below. While not explicitly shown, trocar (356) may include features similar to trocar actuator (231), connecting band portion (235), and trocar (230) described above. Trigger (354) is pivotably coupled to body (352) and is configured to actuate a driver actuator, similar to drive actuator (64, 314) described above, in order to fire a staple head assembly to simultaneously staple and sever tissue suitably captured between an anvil and staple head assembly in accordance with the teachings herein.

Trocar actuation assembly (360) includes a proximal frame (362), an adjustment knob (366), a threaded rod (368), a pivot handle (370), and a coupling link (372). As will be described in greater detail below, trocar actuator assembly (360) is configured to actuate a trocar (356), while coupled with an anvil, from an open position toward a first closed position utilizing a pivot handle (370). Additionally, trocar actuator assembly (360) is configured to actuate trocar (356), while coupled with anvil (322), between the first closed position and a second closed position utilizing an adjustment knob (366).

It should be understood that in the open position, a distal end of trocar (356) may extend distally past staple head assembly (320) such that trocar (356) may suitably couple with an anvil in accordance with the teachings herein. The first closed position may correspond to a gap distance d between anvil (322) and staple head assembly (320) such that if driver actuator (314) is fired is accordance with the teachings herein, staples (66) will form a suitable large staple height compression. Alternatively, the first closed position may correspond to a gap distance d between anvil (322) and staple head assembly (320) such that that anvil (322) is slightly distal compared to the position required for staples (66) to form a suitable large staple height compression. In such instances, the operator may be required to proximally actuate trocar (356) and anvil (322) from the first closed position utilizing adjustment knob (366) and threaded rod (368) to achieve a suitable gap distance d corresponding with a large staple height compression. The second closed position may correspond to a gap distance d between anvil (322) and staple head assembly (320) such that if driver actuator (314) is fired in accordance with the teachings herein, staples (66) will form a suitable small staple height compression.

Proximal frame (362) is attached to a proximal end of trocar (356) such that movement of proximal frame (362) results in movement of trocar (356). Proximal frame (362) is slidably disposed within body (352) such that proximal frame (362) may translate relative to body (352). However, proximal frame (362) is rotationally fixed within body (352) such that proximal frame (362) may not rotate about its own longitudinal axis. Proximal frame (362) may be rotationally fixed and slidably coupled with body (352) via a pin and slot relationship, or any other suitable coupling that would be apparent to one of ordinary skill in the art in view of the teachings herein. As shown in FIG. 15, proximal frame (362) defines a threaded channel (364) dimensioned to selectively receive and mesh with threaded rod (368). Proximal frame (362) is pivotably coupled with coupling link (372) via a pivot coupling (376).

Pivot handle (370) is pivotably coupled with body (352) via pivot coupling (378). Pivot handle (370) defines a slot (375). Pivot handle (370) is rotationally and slidably coupled with coupling link (372) via slot (375) and pivot coupling (374). Therefore, coupling link (372) acts as an intermediary between pivot handle (370) and proximal frame (362).

Pivot handle (370) is configured to rotate relative to body (352) such that coupling link (372) drives proximal frame (362), and therefore trocar (356), between the open position and the first closed position in response to rotation of pivoting handle (370) relative to body (352). Pivot handle (370) may also act as a lockout feature until pivot handle (370) is rotated to the position associated with the first closed position. Therefore, pivot handle (370) may mechanically prevent trigger (354) from pivoting toward body (352) until pivoted to the position shown in FIG. 14B.

Figure 14B:
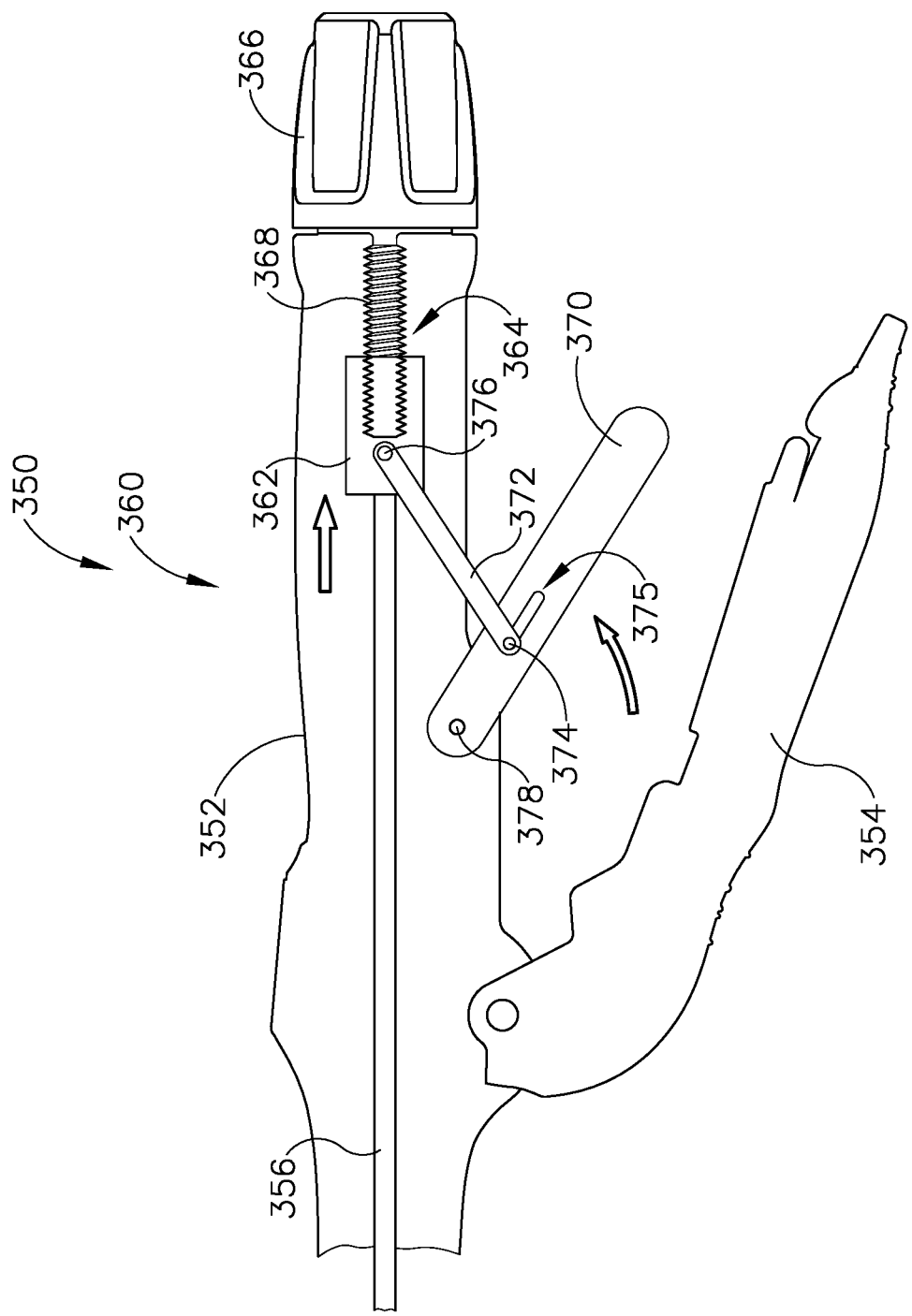
FIG. 14B depicts a cross-sectional side view of the actuator handle assembly of FIG. 14A, where the trocar actuation assembly is in a second configuration associated with the anvil in a first closed position.

When the operatory wishes to actuate trocar (356) from the open position (as shown in FIG. 14A) toward the first closed position (as shown in FIG. 14B), the operator may rotate pivot handle (370) toward body (352). As pivot handle (370) rotates toward body (352), coupling link (372) may rotate relative to body pivot handle (370) and proximal frame (362). In response to pivot handle (370) rotating coupling link (372), proximal frame (362) is driven proximally such that trocar (356) is actuated to the first closed position. The length of slot (375) is dimensioned such that as pivot handle (370) travels in an arched motion, coupling link (372) is permitting to translate and rotate such that proximal frame (362) travels in a substantially linear motion through the entire range or motion of trocar (356) (i.e. from the open position all the way to the second closed position). If the operator desires to actuate trocar (356) from the first closed position back into the open position, the operator may simply rotate pivot handle (370) in the opposite angular direction described above in order to drive proximal frame (362) and trocar (356) distally in accordance with the description herein.

Adjustment knob (366) is rotationally disposed on the proximal end of body (352). Therefore, adjustment knob (366) may rotate relative to body (352), similar to the relationship between adjustment knob (98) and body (72) described above. Threaded rod (368) extends distally from adjustment knob (366) into the interior of body (352). Threaded rod (368) is attached to adjustment knob (366) such that rotation of adjustment knob (366) causes rotation of threaded rod (368).

As mentioned above, threaded rod (368) is dimensioned to suitably mesh with threaded channel (364) of proximal frame (362). As shown in FIG. 14B, when proximal frame (362) is actuated by pivot handle (370) and coupling link (372) to the position where trocar (356) is in the first closed position, a distal end of threaded rod (368) is directly adjacent to, and aligned with, a proximal end of threaded channel (364). At this moment, threaded rod (368) would prevent further proximal translation of proximal frame (362) via further pivoting of handle (370). Instead, as shown between FIGS. 14B and 14C, if the operator desires to actuate proximal frame (362) further proximally such that trocar (356) actuates between the first closed position and the second closed position, the operator may rotate adjustment knob (366) in a first angular direction until a distal end of threaded rod (368) catches into engagement with thread channel (364) such that threaded rod (338) and threaded channel (364) begin to mesh.

Figure 14C:
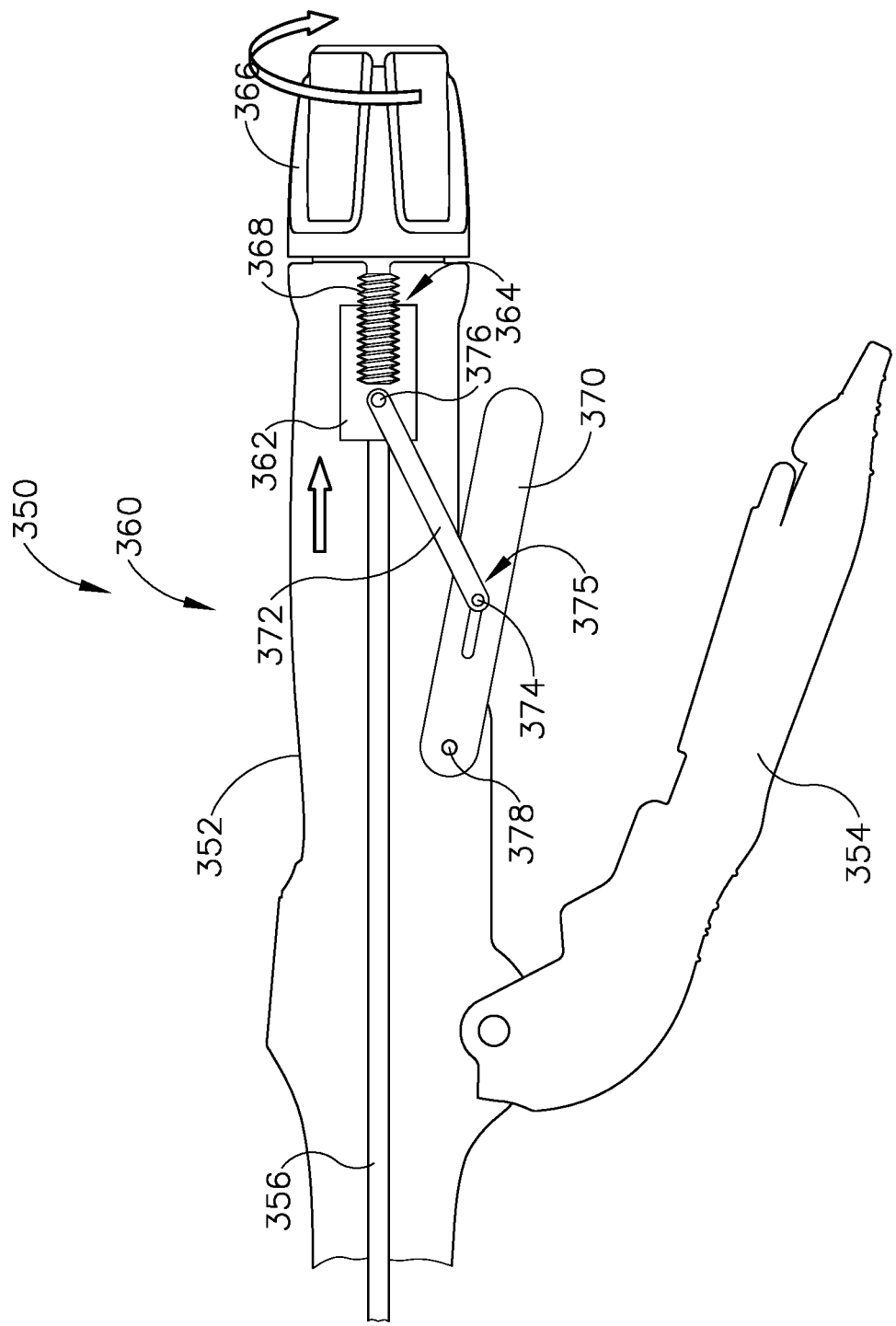
FIG. 14C depicts a cross-sectional side view of the actuator handle assembly of FIG. 14A, where the trocar actuation assembly is in a third configuration associated with the anvil in a second closed position.

Because proximal frame (362) is slidably housed and rotationally constrained within body (352), when threaded rod (368) meshes with threaded channel (364), rotation of threaded rod (368) drives translation of proximal frame (362) and trocar (356). Therefore, as shown in FIG. 14C, the operator may rotate adjustment knob (366) in the first angular direction to urge proximal frame (362) and trocar (356) proximally toward the second closed position. Conversely, the operator may rotate adjustment knob (366) in the second angular direction to urge proximal frame (362) and trocar (356) distally toward the first closed position. If the operator accidentally rotates adjustment knob (366) in the second angular direction such that proximal frame (362) and trocar (356) reach the first closed position, threaded rod (368) and threaded channel (364) will no longer mesh. Therefore, further rotation of adjustment knob (366) in the second angular direction while trocar (356) is in the first closed position will no longer actuate proximal frame (362) or trocar (356) in the distal direction.

It should be understood that in instances where the first closed position corresponds to a gap distance d between anvil and staple head assembly such that anvil is slightly distal compared to the position required for staples (66) to form a suitable large staple height compression, threaded rod (368) and threaded channel (364) mesh when anvil and staple head assembly define a suitable gap distance d for a large staple height compression.

In the current example threaded rod (368) and threaded channel (364) are used to convert rotational movement of adjustment knob (366) into translational movement of proximal frame (362). However, this is merely optional, as any suitably mechanism to convert rotational movement into translational movement, or vice versa, may be used as would be apparent to one having ordinary skill in the art in view of the teachings herein. For example, a threadless rod and rolling ring bearing assembly may be used.

In some instances, it may be desirable to have a dual closure trocar actuation assembly having distinguishable driving motions for larger movement of trocar (230) and a smaller, more finely tuned, movement of trocar (230); while also having features configured to selectively latch trocar (230) at certain desirable locations relative to the rest of instrument (10) during a suitable operation.

FIGS. 16A-17D show an alternative exemplary circular surgical stapling instrument (400). While not explicitly described below, instrument (400) may have various features and functionality described above for instrument (10). Therefore, instrument (400) is substantially similar to instrument (10) described above, with differences elaborated below. Instrument (400) includes an actuator handle assembly (402), a shaft assembly (410), a staple head assembly (420), and an anvil (422); which are substantially similar to actuator handle assembly (70), shaft assembly (60), stapling head assembly (200), and anvil (40) described above, respectively, with differences elaborated below.

Actuator handle assembly (402) includes a body (404), and a trigger (406), which are substantially similar to body (72), and a trigger (74) described above, respectively, with differences elaborated below. Additionally, actuator handle assembly (402) includes a dual stage trocar actuation assembly (430). As will be described in greater detail below, trocar actuation assembly (430) includes a first detent (446) and a second detent (448) configured to selectively fix trocar (416) relative to the rest of instrument (400) at a sub-flush position and the open position, respectively. Trocar actuator assembly (430) is also configured to actuate a trocar (416), while coupled with anvil (422), from an open position toward a first closed position utilizing a pivot handle (440). Additionally, trocar actuator assembly (430) is configured to actuate trocar (416), while coupled with anvil (422), between the first closed position and a second closed position utilizing an adjustment knob (436).

Shaft assembly (410) includes an outer tubular member (412), a driver actuator (414), and a trocar (416), which are substantially similar to outer tubular member (62), driver actuator (64), and trocar (230) described above, respectively. While not explicitly shown, trocar (416) may include features similar to trocar actuator (231) and connecting band portion (235) described above. Driver actuator (414) extends between staple head assembly (420) and trigger (406) such that trigger (406) may pivot toward body (404) in order to fire staple head assembly (420) to simultaneously staple and sever tissue suitably captured between anvil (422) and staple head assembly (420) in accordance with the teachings herein.

Trocar actuation assembly (430) includes a proximal frame (432), adjustment knob (436), a threaded rod (438), pivot handle (440), first detent (446), and second detent (448). First detent (446) is configured to selectively fix trocar (416) at a sub-flush position, while second detent (448) is configured to selectively fix trocar (416) at the open position. As mentioned above, and as will be described in greater detail below, pivot handle (440) is configured to actuate trocar (416) between an open position and a first closed position, while adjustment knob (436) and threaded rod (438) are configured to actuate trocar (416) from the first closed position further toward the second closed position.

It should be understood that in the sub-flush position, the distal end of trocar (416) is housed within staple head assembly (420). Trocar (416) may be initially set at the sub-flush position during shipment of instrument (400) and prior to suitable use of instrument (400). Trocar (416) may be placed in the sub-flush position so that the distal end of trocar (416) is not inadvertently exposed or damaged prior to suitable use.

It should be understood that in the open position, a distal end of trocar (416) may extend distally past staple head assembly (420) such that trocar (416) may suitably couple with anvil (422) in accordance with the teachings herein. The first closed position may correspond to a gap distance d between anvil (422) and staple head assembly (420) such that if driver actuator (414) is fired is accordance with the teachings herein, staples (66) will form a suitable large staple height compression. Alternatively, the first closed position may correspond to a gap distance d between anvil (422) and staple head assembly (420) such that anvil (422) is slightly distal compared to the position required for staples (66) to form a suitable large staple height compression. In such instances, the operator may be required to proximally actuate trocar (416) and anvil (422) from the first closed position utilizing adjustment knob (436) and threaded rod (438) to achieve a suitable gap distance d corresponding with a large staple height compression. The second closed position may correspond to a gap distance d between anvil (422) and staple head assembly (420) such that if driver actuator (414) is fired in accordance with the teachings herein, staples (66) will form a suitable small staple height compression.

Proximal frame (432) is attached to a proximal end of trocar (416) such that movement of proximal frame (432) results in movement of trocar (416). Proximal frame (432) is slidably disposed within body (304) such that proximal frame (432) may translate relative to body (404). However, proximal frame (432) is rotationally fixed within body (404) such that proximal frame (432) may not rotate about its own longitudinal axis. Proximal frame (432) may be rotationally fixed and slidably coupled with body (404) via a pin and slot relationship, or any other suitable coupling that would be apparent to one of ordinary skill in the art in view of the teachings herein. Proximal frame (432) includes a transverse projection (444) slidably housed within a slot (445) defined by pivot handle (440). Additionally, proximal frame (432) defines a threaded channel (434) and a channel (431). Threaded channel (434) is dimensioned to selectively receive and mesh with threaded rod (438). Channel (431) is dimensioned to selectively receive first detent (446) and second detent (448) in order secure the position of trocar (416) relative to the rest of instrument (400).

A bias element (435), such as a helical spring, is disposed between a distal surface of proximal frame (432) and a shoulder (405) of body (404). In the current example, bias element (435) extends around a portion of trocar (416) extending between shoulder (405) and proximal frame (432). However, bias element (435) may be disposed between distal surface of proximal frame (432) and any suitable component to bias trocar (416) toward a suitable position as would be apparent to one having ordinary skill in the art in view of the teachings herein. In one embodiment, bias element (435) biases proximal frame (432), and therefore trocar (416), toward the first closed position (shown in FIGS. 16C and 17C). However, bias element (435) may bias proximal frame (432), and therefore trocar (416), toward any suitably position as would be apparent to one of ordinary skill in view of the teachings herein.

Figure 16A:
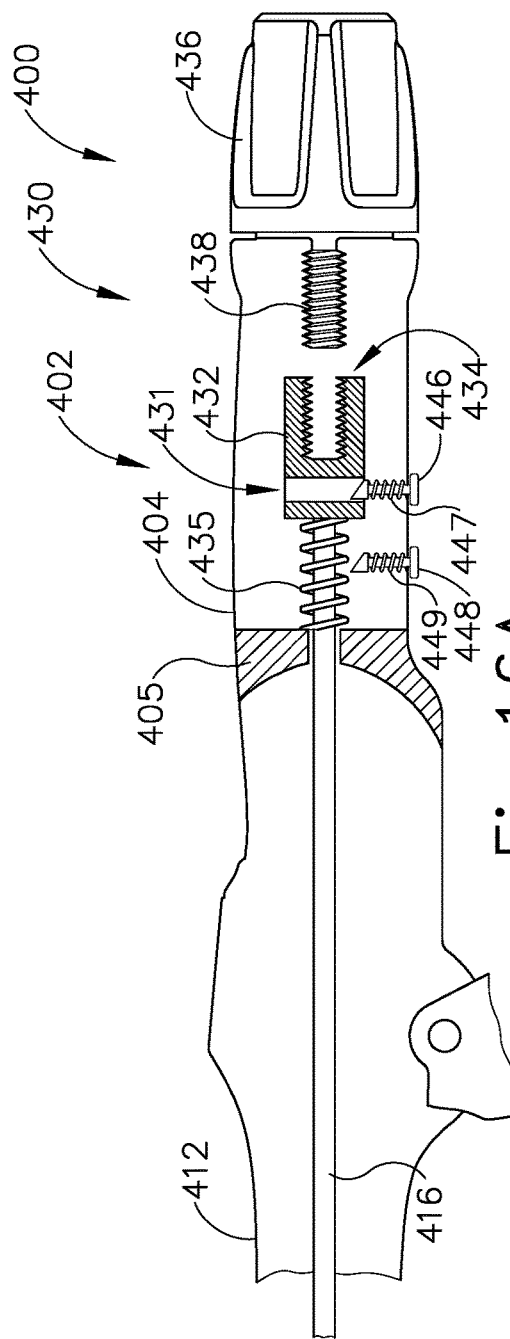
FIG. 16A depicts a cross-sectional top view of a portion of an alternative circular stapling surgical instrument, where a trocar actuation assembly is in a first configuration associated with a trocar in a pre-deployed position.

First detent (446) and second detent (448) are both slidably coupled with a portion of body (404). Detents (446, 448) are longitudinally fixed relative to body (404), but may actuate transversely relative to body (404) in order to selectively couple with proximal frame (432) by entering channel (431). Because detents (446, 448) are longitudinally fixed relative to body (404), when within channel (431) of proximal frame (432), detents (446, 448) are configured to longitudinally fix proximal frame (432), and therefore trocar (416), relative to body (404). Detents (446, 448) are biased into an inward position (as shown in FIGS. 16A, 16D, and 16D) via bias elements such as springs (447, 449), respectively. Detents (446, 448) may be configured to actuate transversally out of channel (431) when the operator overcomes the bias force of springs (447, 449) to actuate detents (446, 448) out of channel (431). Once detents (446, 448) are actuated out of channel (431), the operator may longitudinally actuate proximal frame (432) relative to body (404) in accordance with the description herein.

The operator may overcome the bias force of springs (447, 449) in order to decouple detents (446, 448) from channel (431) of proximal frame (432) through any suitably means as would be apparent to one having ordinary skill in the art in view of the teachings herein. For example, the operator may pull the portion of detents (446, 448) located on the exterior of body (404) by hand such that detents (446, 448) exit channel (431). At which point, the operator may rotate handle (440) to actuate proximal frame (432) in accordance with the description herein such that channel (431) is no longer longitudinally aligned with respective detent (446, 448). Alternatively, channel (431) and detents (446, 448) may have a camming relationship such that when the operator sufficiently rotates pivot handle (440), proximal frame (432) is actuated such that the interior surface of channel (431) cams against the portion of detent (446, 448) within channel (431), thereby overcoming the bias force of springs (447, 449) and driving detents (446, 448) out of engagement with channel (431).

In the current example, detents (446, 448) and channel (431) align at the sub-flush and open position, respectively, such that handle (440) controls the movement of proximal frame (432) when detents (446, 448) are within channel (431). It should be understood that this is merely optional. Detents (446, 448), or extra detents, may be placed along body (404) to align with channel (431) while adjustment knob (436) controls movement of proximal frame (432) in accordance with the description herein.

Pivot handle (440) is pivotably coupled with body (404) via pivot pin (442). Pivot handle (440) is configured to actuate trocar (416), and anvil (422) when suitably coupled to trocar (416), between the sub-flush position, the open position, and the first closed position. A portion of pivot handle (440) extends away from body (404), while another portion of pivot handle (440) extends within body (404). The first portion of pivot handle (440) is dimensioned to be grasped by the operator. The second portion of pivot handle (440) extending within handle defines slot (445) that slidably houses transverse projection (444) of proximal frame (432). Pivot handle (440) may also act as a lockout feature until pivot handle (440) is rotated to the position associated with the first closed position. Therefore, pivot handle (440) may mechanically prevent trigger (406) from pivoting toward body (404) until pivoted to the position shown in FIGS. 17C-17D.

Figure 17A:
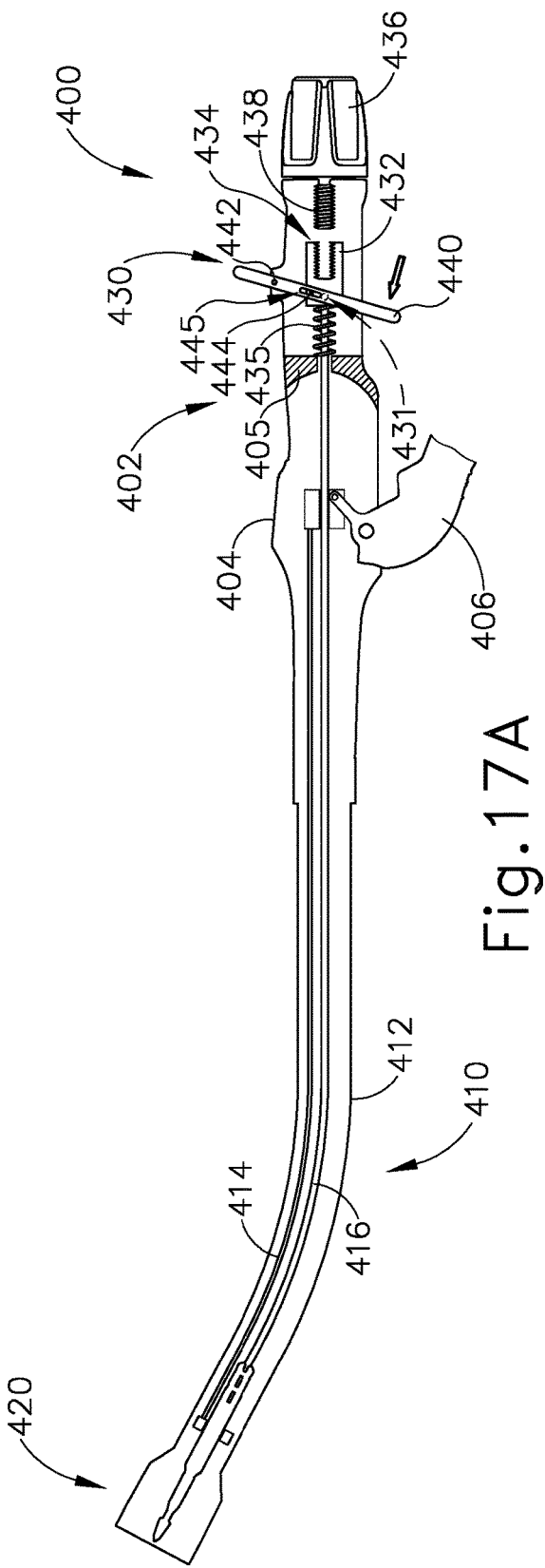
FIG. 17A depicts a cross-sectional side view of the circular stapling surgical instrument of FIG. 16A, where the trocar actuation assembly is in the first configuration associated with the trocar in the pre-deployed position.
Figure 16B:
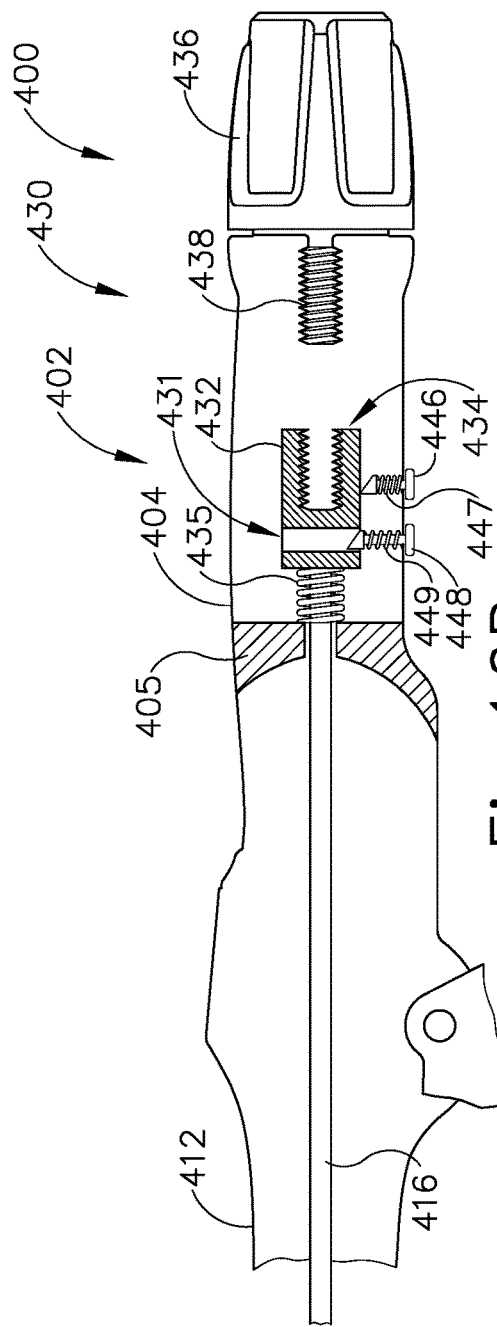
FIG. 16B depicts a cross-sectional top view of a portion of the circular stapling surgical instrument of FIG. 16A, where the trocar actuation assembly is in a second configuration associated with the trocar and an anvil in an open position.
Figure 17B:
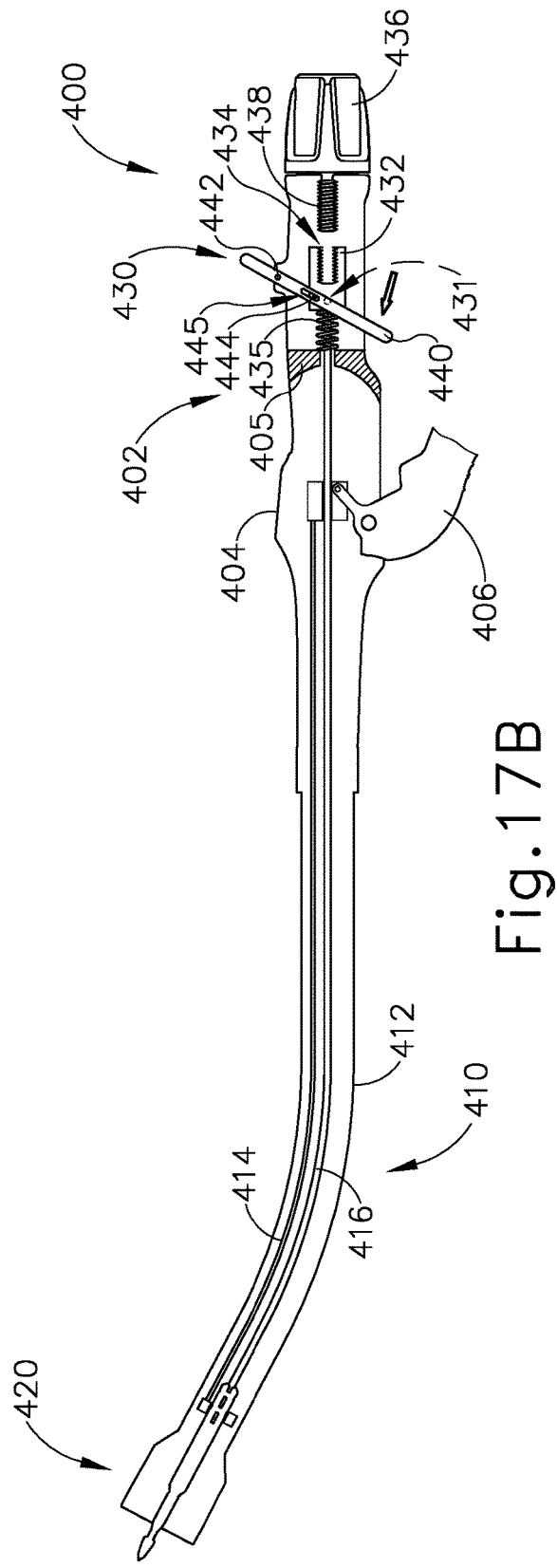
FIG. 17B depicts a cross-sectional side view of a portion of the circular stapling surgical instrument of FIG. 16A, where the trocar actuation assembly is in the second configuration associated with the trocar and the anvil in the open position.

When the operator wants to actuate trocar (416) from the sub-flush position (as shown in FIGS. 16A and 17A) toward the open position (as shown in FIGS. 16B and 17B), the operator may decouple first detent (446) from channel (431) in accordance with the description herein and grasp the first portion of pivot handle (440) to rotate pivot handle (440) in a first angular direction. Because transverse projection (444) is slidably housed within slot (445) of pivot handle (440), the second portion of pivot handle (440) drives proximal frame (432) and trocar (416) distally toward the opened position. The length of slot (445) is dimensioned such that as pivot handle (440) travels in an arched motion, proximal frame (432) is permitted to travel in a substantially linear motion through the entire range or motion of trocar (416) (i.e. from the open position all the way to the second closed position). It should be understood that once trocar (416) is in the open position, second detent (448) is within channel (431), thereby selectively fixing trocar (416) in the open position. In the open position, trocar (416) may selectively couple with anvil (422) in accordance with the description herein.

When the operator wants to actuate trocar (416) from the open position (as shown in FIGS. 16B and 17B) to the first closed position (as shown in FIGS. 16C and 17C) the operator may decouple second detent (448) from channel (431) in accordance with the description herein. The operator may then grasp the first portion of pivot handle (440) and rotate pivot handle (440) in the second angular direction such that proximal frame (432) actuates proximally. Bias element (435) may help further actuate proximal frame (432) and trocar (416) in the proximal direction toward the first closed position. The operator may need to further actuate proximal frame (432) such that channel (431) longitudinally travels past first detent (446) in accordance with the description herein. Bias element (435) may help ensure threaded channel (434) is directly adjacent to a distal end of threaded rod (438) when trocar (416) is in the first closed position.

If the operator desires to actuate trocar (416) from the first closed position back into either the sub-flush position or the open position, the operator may simply pivot the first portion of handle (440) in the first angular direction in order to drive proximal frame (432) and trocar (416) distally in accordance with the description herein.

Adjustment knob (436) is rotationally disposed on the proximal end of body (404). Therefore, adjustment knob (436) may rotate relative to body (404), similar to the relationship between adjustment knob (98) and body (72) described above. Threaded rod (438) extends distally from adjustment knob (436) into the interior of body (404). Threaded rod (438) is attached to adjustment knob (436) such that rotation of adjustment knob (436) causes rotation of threaded rod (438).

As mentioned above, threaded rod (438) is dimensioned to suitably mesh with threaded channel (434) of proximal frame (432). As shown in FIGS. 16C and 17C, when proximal frame (432) is actuated by pivot handle (440) and/or bias element (435) to the position where trocar (416) is in the first closed position, a distal end of threaded rod (438) is directly adjacent to, and aligned with, a proximal end of threaded channel (434). At this moment, threaded rod (438) would prevent further proximal translation of proximal frame (432) via further pivoting of handle (440) or force from bias element (435). Instead, as shown between FIGS. 16C-16D and 17C-17D, if the operator desires to actuate proximal frame (432) further proximally such that trocar (416) actuates between the first closed position and the second closed position, the operator may rotate adjustment knob (436) in a first angular direction until a distal end of threaded rod (438) catches into engagement with threaded channel (434) such that threaded rod (438) and threaded channel (434) begin to mesh.

Because proximal frame (432) is slidably housed and rotationally constrained within body (404), when threaded rod (438) meshes with threaded channel (434), rotation of threaded rod (438) drives translation of proximal frame (432), and therefore drives translation of trocar (416). Therefore, as shown in FIGS. 16D and 17D, the operator may rotate adjustment knob (436) in the first angular direction to urge proximal frame (432) and trocar (416) proximally toward the second closed position. Conversely, the operator may rotate adjustment knob (436) in the second angular direction to urge proximal frame (432) and trocar (416) distally toward the first closed position. If the operator accidentally rotates adjustment knob (436) in the second angular direction such that proximal frame (432) and trocar (416) reach the first closed position, threaded rod (438) and threaded channel (434) will no longer mesh. Bias element (435) may keep proximal frame (432) and trocar (416) in the first closed position. Therefore, further rotation of adjustment knob (436) in the second angular direction while trocar (416) is in the first closed position will no longer actuate proximal frame or trocar (416) in the distal direction.

It should be understood that in instances where the first closed position corresponds to a gap distance d between anvil (422) and staple head assembly (420) such that that anvil (422) is slightly distal compared to the position required for staples (66) to form a suitable large staple height compression, threaded rod (438) and threaded channel (434) mesh when anvil (422) and staple head assembly (420) define a suitable gap distance d for a large staple height compression.

In the current example threaded rod (438) and threaded channel (434) are used to convert rotational movement of adjustment knob (436) into translational movement of proximal frame (432). However, this is merely optional, as any suitable mechanism to convert rotational movement into translational movement, or vice versa, may be used as would be apparent to one having ordinary skill in the art in view of the teachings herein. For example, a threadless rod and rolling ring bearing assembly may be used.

Figure 18A:
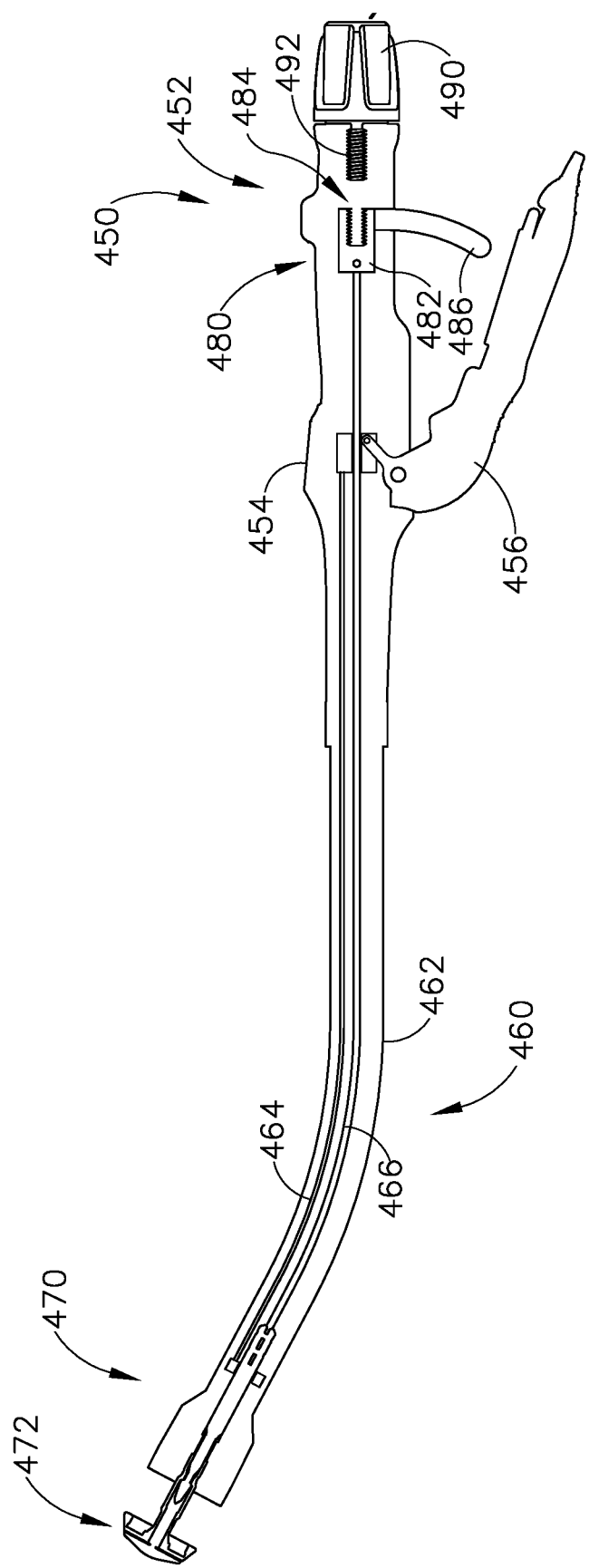
FIG. 18A depicts a cross-sectional side view of an alternative circular stapling surgical instrument, where a trocar actuation assembly is in a first configuration associated with an anvil in an open position.
Figure 18B:
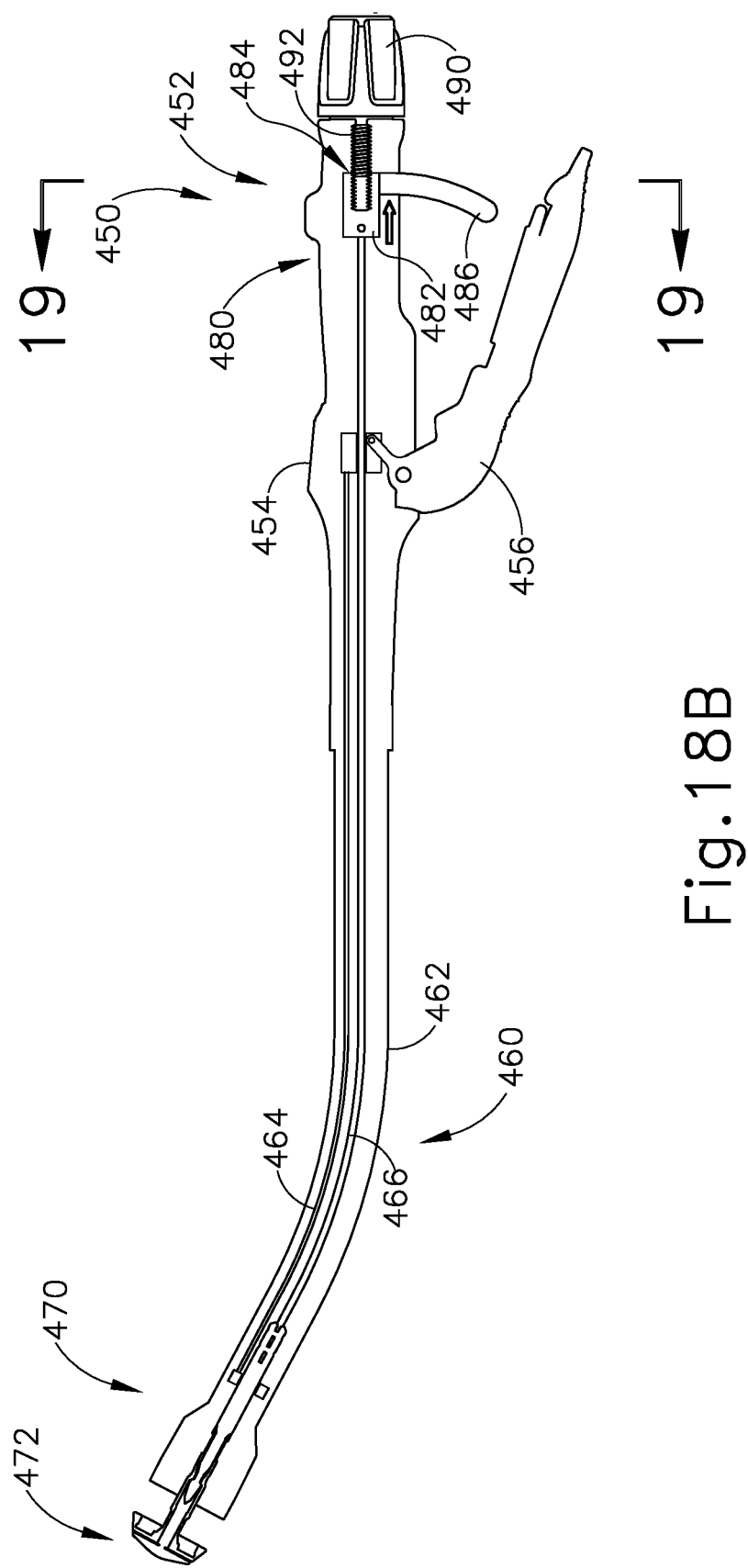
FIG. 18B depicts a cross-sectional side view of the circular stapling surgical instrument of FIG. 18A, where the trocar actuation assembly is in a second configuration associated with the anvil in a first closed position.
Figure 18C:
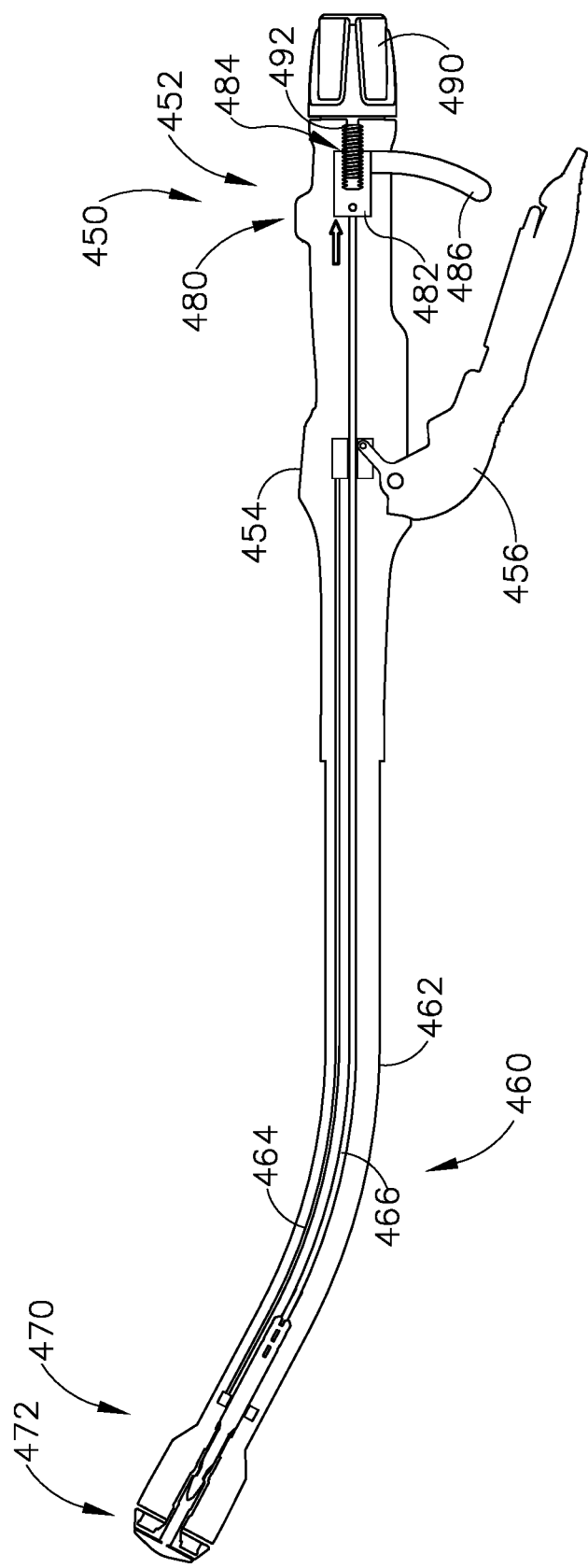
FIG. 18C depicts a cross-sectional side view of the circular stapling surgical instrument of FIG. 18A, where the trocar actuation assembly is in a third configuration associated with the anvil in a second closed position.
Figure 19:
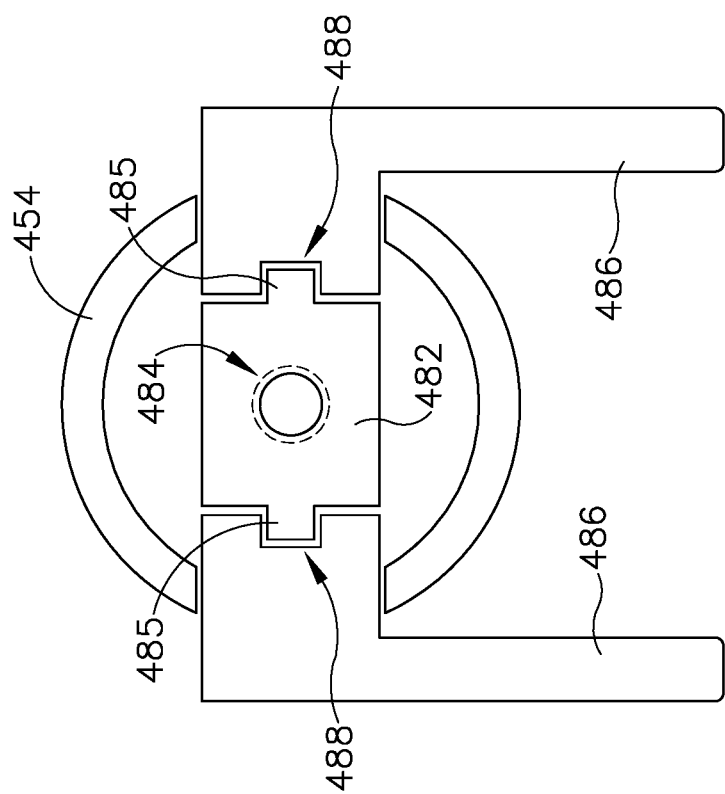
FIG. 19 depicts a cross-sectional view of the circular stapling surgical instrument of FIG. 18A, taken along line 19-19 of FIG. 18B.

FIGS. 18A-19 show an alternative exemplary circular surgical stapling instrument (450). While not explicitly described below, instrument (450) may have various features and functionality described above for instrument (10). Therefore, instrument (450) is substantially similar to instrument (10) described above, with differences elaborated below. Instrument (450) includes an actuator handle assembly (452), a shaft assembly (460), a staple head assembly (470), and an anvil (472); which are substantially similar to actuator handle assembly (70), shaft assembly (60), staple head assembly (200), and anvil (40) described above, respectively, with differences elaborated below.

Actuator handle assembly (452) includes a body (454), and a trigger (456), which are substantially similar to body (72), and trigger (74) described above, respectively, with differences elaborated below. Additionally, actuator handle assembly (452) includes a dual stage trocar actuation assembly (480). As will be described in greater detail below, trocar actuator assembly (480) is configured to actuate a trocar (466), while coupled with anvil (472), from an open position toward a first closed position utilizing a sliding handle (486). Additionally, trocar actuator assembly (480) is configured to actuate trocar (466), while coupled with anvil (472), between the first closed position and a second closed position utilizing an adjustment knob (490).

Shaft assembly (460) includes an outer tubular member (462), a driver actuator (464), and a trocar (466), which are substantially similar to outer tubular member (62), driver actuator (64), and trocar (230) described above, respectively. While not explicitly shown, trocar (466) may include features similar to trocar actuator (231) and connecting band portion (235) described above. Driver actuator (464) extends between staple head assembly (470) and trigger (456) such that trigger (456) may pivot toward body (454) in order to fire staple head assembly (470) to simultaneously staple and sever tissue suitably captured between anvil (472) and staple head assembly (470) in accordance with the teachings herein.

Trocar actuation assembly (480) includes a proximal frame (482), adjustment knob (490), a threaded rod (492), and sliding handle (486). As mentioned above, and as will be described in greater detail below, sliding handle (486) is configured to actuate trocar (466) between an open position and a first closed position, while adjustment knob (490) and threaded rod (492) are configured to actuate trocar (466) from the first closed position further toward the second closed position.

It should be understood that in the open position, a distal end of trocar (466) may extend distally past staple had assembly (470) such that trocar (466) may suitably couple with anvil (472) in accordance with the teachings herein. The first closed position may correspond to a gap distance d between anvil (472) and staple head assembly (470) such that if driver actuator (464) is fired is accordance with the teachings herein, staples (66) will form a suitable large staple height compression. Alternatively, the first closed position may correspond to a gap distance d between anvil (472) and staple head assembly (470) such that anvil (472) is slightly distal compared to the position required for staples (66) to form a suitable large staple height compression. In such instances, the operator may be required to proximally actuate trocar (466) and anvil (472) from the first closed position utilizing adjustment knob (490) and threaded rod (492) to achieve a suitable gap distance d corresponding with a large staple height compression. The second closed position may correspond to a gap distance d between anvil (472) and staple head assembly (470) such that if driver actuator (464) is fired in accordance with the teachings herein, staples (66) will form a suitable small staple height compression.

Proximal frame (482) is attached to a proximal end of trocar (466) such that movement of proximal frame (482) results in movement of trocar (466). Proximal frame (482) is slidably disposed within body (454) such that proximal frame (482) may translate relative to body (454). However, proximal frame (482) is rotationally fixed within body (454) such that proximal frame (482) may not rotate about its own longitudinal axis. Additionally, proximal frame (332) defines a threaded channel (334) dimensioned to selectively receive and mesh with threaded rod (338). Proximal frame (482) is coupled to sliding handles (486) via coupling features (485, 488). Sliding handles (486) extend from an exterior of body (454) into the interior of body (454) to rationally fix proximal frame (482) about its own longitudinal axis. Therefore, body (454) defines a slot to receive portions of sliding handles (486).

Sliding handles (486) are slidably attached to body (454) such that the operator may grasp sliding handles (486) and translate handles (486) relative to body (454). In particular, the operator may translate sliding handles (486) proximally such that proximal frame (482) and trocar (466) actuate between the open position and the first closed position (as shown between FIGS. 18A-18B). If the operator desires to actuate trocar (466) from the first closed position back into the open position, the operator may simply translate handles (486) distally in order to drive proximal frame (482) and trocar (466) distally in accordance with the description herein.

Adjustment knob (490) is rotationally disposed on the proximal end of body (454). Therefore, adjustment knob (490) may rotate relative to body (454), similar to the relationship between adjustment knob (98) and body (72) described above. Threaded rod (492) extends distally from adjustment knob (490) into the interior of body (454). Threaded rod (492) is attached to adjustment knob (490) such that rotation of adjustment knob (490) causes rotation of threaded rod (492).

As mentioned above, threaded rod (492) is dimensioned to suitably mesh with threaded channel (484) of proximal frame (482). As shown in FIG. 18B, when proximal frame (482) is actuated by sliding handle (486) to the position where trocar (466) is in the first closed position, a distal end of threaded rod (492) is directly adjacent to, and aligned with, a proximal end of threaded channel (484). At this moment, threaded rod (492) would prevent further proximal translation of proximal frame (482) via further translation of handle (486). Instead, as shown between FIGS. 18B and 18C, if the operator desires to actuate proximal frame (482) further proximally such that trocar (466) actuates between the first closed position and the second closed position, the operator may rotate adjustment knob (490) in a first angular direction until a distal end of threaded rod (492) catches into engagement with threaded channel (484) such that threaded rod (492) and threaded channel (484) begin to mesh.

Because proximal frame (482) is slidably housed and rotationally constrained within body (454), when threaded rod (492) meshes with threaded channel (484), rotation of threaded rod (492) drives translation of proximal frame (482), and therefore drives translation of trocar (466). Therefore, as shown in FIG. 18C, the operator may rotate adjustment knob (490) in the first angular direction to urge proximal frame (482) and trocar (466) proximally toward the second closed position. Conversely, the operator may rotate adjustment knob (490) in the second angular direction to urge proximal frame (482) and trocar (466) distally toward the first closed position. If the operator accidentally rotates adjustment knob (490) in the second angular direction such that proximal frame (482) and trocar (466) reach the first closed position, threaded rod (492) and threaded channel (484) will no longer mesh. Therefore, further rotation of adjustment knob (490) in the second angular direction while trocar (466) is in the first closed position will no longer actuate proximal frame (482) or trocar (466) in the distal direction.

It should be understood that in instances where the first closed position corresponds to a gap distance d between anvil (472) and staple head assembly (470) such that that anvil (472) is slightly distal compared to the position required for staples (66) to form a suitable large staple height compression, threaded rod (492) and threaded channel (484) mesh when anvil (472) and staple head assembly (470) define a suitable gap distance d for a large staple height compression.

In the current example threaded rod (492) and threaded channel (484) are used to convert rotational movement of adjustment knob (490) into translational movement of proximal frame (482). However, this is merely optional, as any suitably mechanism to convert rotational movement into translational movement, or vice versa, may be used as would be apparent to one having ordinary skill in the art in view of the teachings herein. For example, a threadless rod and rolling ring bearing assembly may be used.

As mentioned above, threaded rod (338, 368, 438, 492) and threaded channel (334, 364, 434, 484) of proximal frame (332, 362, 432, 482) are configured to align directly adjacent with each other in the first closed position such that rotation of threaded rod (338, 368, 438, 492) in a first angular direction causes threaded rod (338, 368, 438, 492) and threaded channel (334, 364, 434, 484) to suitably mesh or engage. In some instances, rotation a threaded rod (338, 368, 438, 492) may take multiple rotations to suitably engage or mesh with threaded channel (334, 364, 434, 484). This may be caused by a failure for threads to initially "catch" or engage each other during initial rotations of threaded rod (338, 368, 438, 492). This may result in the operator rotating threaded rod (338, 368, 438, 492) under the assumption that rotation is driving translation of proximal frame (332, 362, 432, 482), when in fact proximal frame (332, 362, 432, 482) is not translating. Therefore, it may be desirable to have an alternative threaded rod and or threaded channel configured to more accurately initially "catch" or engage each other during initial rotation of the threaded rod when the proximal frame is in the first closed position.

B. Alternative Threaded Engagement Devices

Figure 20:
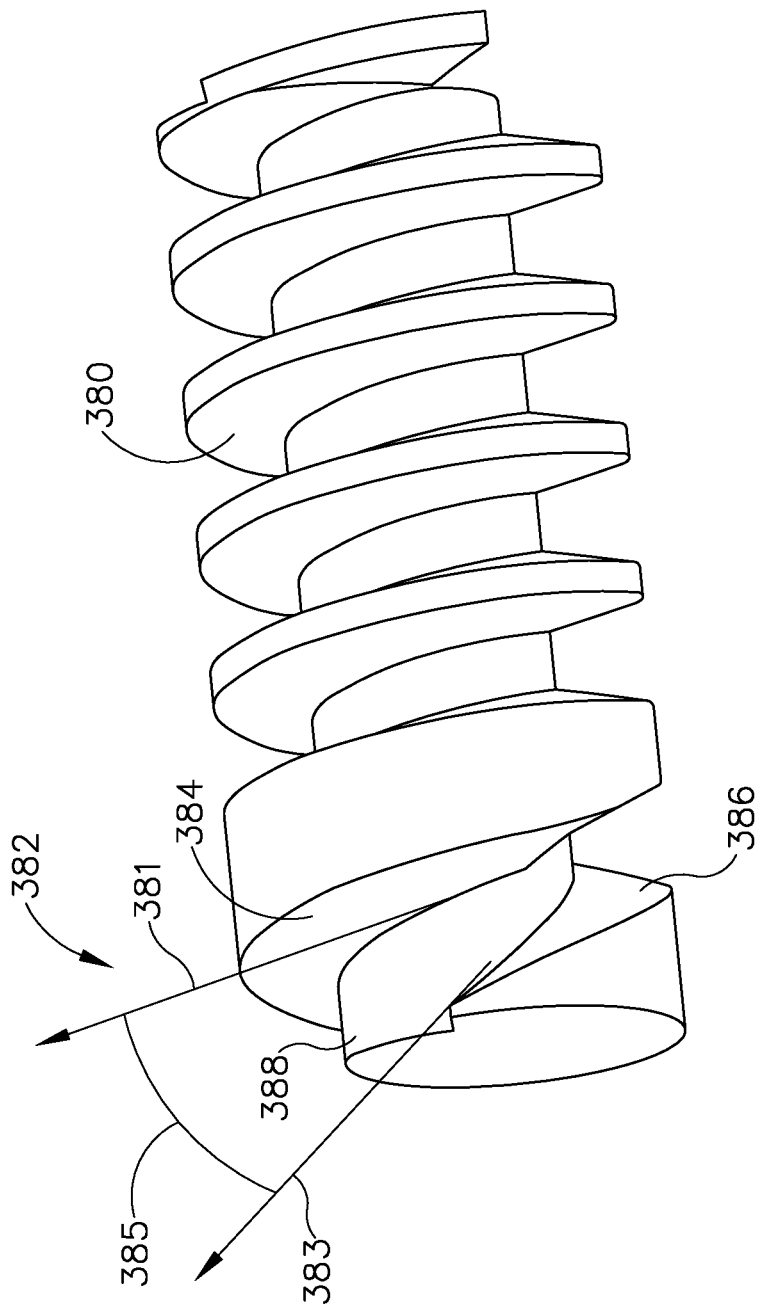
FIG. 20 depicts a perspective view of an alternative threaded rod that may be readily incorporated into the trocar actuation assemblies of FIGS. 13A, 14A, 16A, and 18A.

FIG. 20 shows an alternative threaded rod (380) that may be used in replacement of threaded rod (338, 368, 438, 492) described above. Threaded rod (380) includes a distal funnel style lead-in (382) configured to more reliably initially engage or "catch" threaded channel (334, 364, 434, 484) during initial rotation of threaded rod (380) in the first closed position. Distal funnel style lead-in (382) includes an oblique distal facing surface (384), an oblique proximal facing surface (386), and a landing surface (388) extending between the two oblique surfaces (384, 386). Distal facing surface (384) extends along a first axis (381) while proximal facing surface (386) extends along a second axis (383). First axis (381) and second axis (383) define an opened angle (385) such that landing surface (388) and oblique surfaces (384, 386) define a funnel style lead-in. The funnel style lead-in defined by angle (385) may provide for a larger initial engagement area to allow threaded rod (380) to more easily catch or engage threaded channel (334, 364, 434, 484) of proximal frame (332, 362, 432, 482) as compared to a more traditional style lead in.

FIGS. 21-22 show another alternative threaded rod (390) having a multi-start thread assembly (392). Multi-start thread assembly (392) of the current example includes a first thread (394), a second thread (396), and a third thread (398). Each thread (394, 396, 398) runs parallel from the other. In other words, if a threaded channel engages first thread (394), the threaded channel will travel along the path of first thread (394) without traveling along the path of second thread (396) or third thread (398).

As best seen in FIG. 22, each thread (394, 396, 398) terminates distally such that each thread (394, 396, 398) has a chance to catch or engage threaded channel (334, 364, 434, 484). Therefore, while one revolution of threaded rods (338, 368, 438, 492) include one chance of catching or engaging threaded channel (334, 364, 434, 484), one revolution of multi-start thread assembly (392) includes three chances of engaging threaded channel (334, 364, 434, 484). In the current example, three threads (394, 396, 398) are used, any suitable number of parallel threads may be used as would be apparent to one having ordinary skill in the art in view of the teachings herein.

Figure 23:
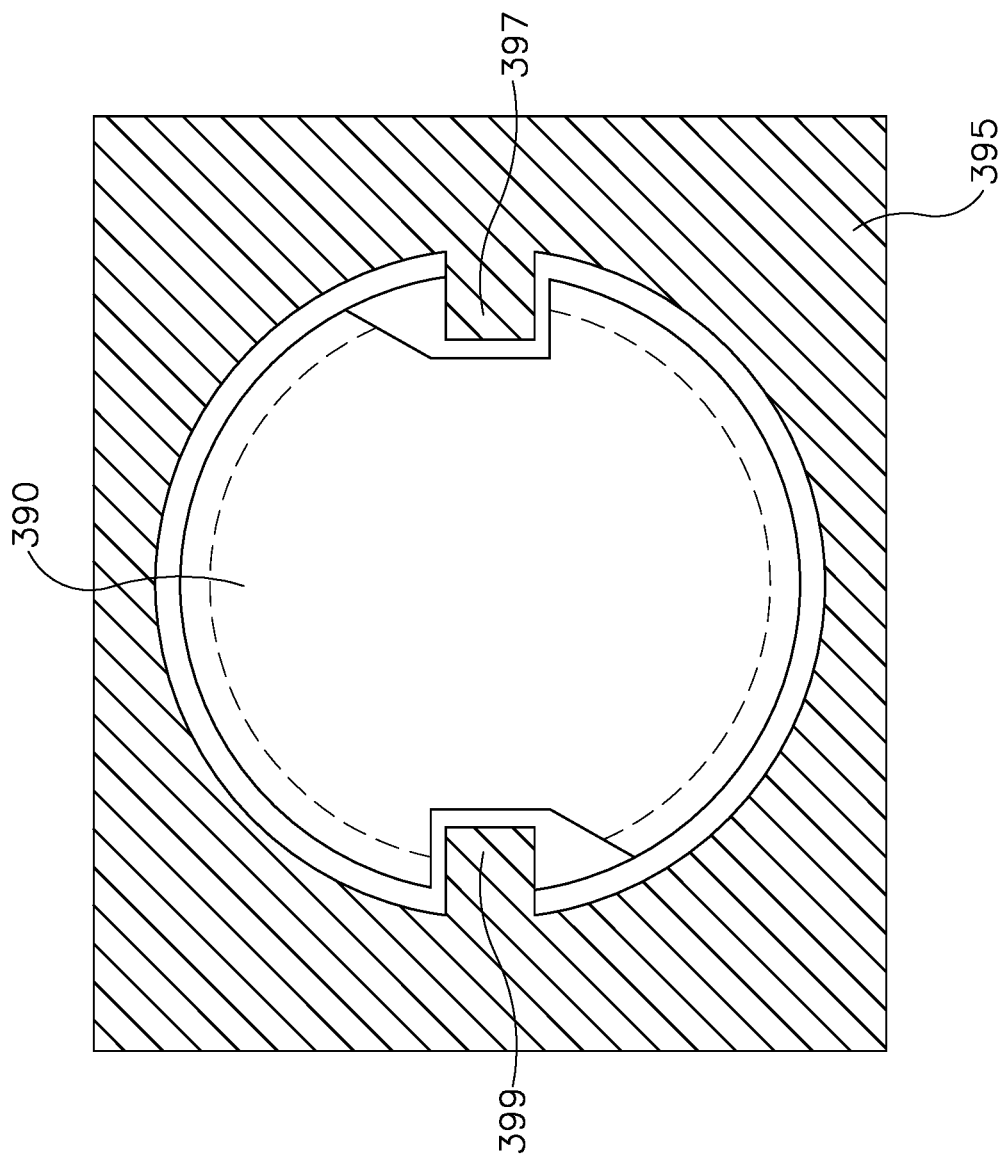
FIG. 23 depicts a cross-sectional front view of the threaded rod of FIG. 21 meshed with an alternative proximal frame that may be readily incorporated into the trocar actuation assemblies of FIGS. 13A, 14A, 16A, and 18A.

FIG. 23 shows an alternative proximal frame (395) having engagement posts (397, 399) engage threaded channels instead of a traditional threaded channel. While two engagement posts (397, 399) are shown in the current example, any suitable number of engagement posts may be used as would be apparent to one of ordinary skill in the art in view of the teachings herein.

C. Exemplary Dual Stage Trocar Actuation Assemblies Having Multi-Directional Input Actuation Mechanism FIGS. 24A-25 show an alternative exemplary actuator handle assembly (500) that may be readily incorporated into instrument (10) described above. While not explicitly described below, actuator handle assembly (500) may have various features and functionality described above for instrument (10). Therefore, actuator handle assembly (500) is substantially similar to actuator handle assembly (70) described above, with differences elaborated below.

Actuator handle assembly (500) includes a body (502), a trigger (504), and a lockout feature (506); which are substantially similar to body (72), a trigger (74), and lockout feature (82) described above, respectively, with differences elaborated below. A trocar (508) extends proximally within body (502). Trocar (508) may be substantially similar to trocar (230) described above, with differences elaborated below. While not explicitly shown, trocar (508) may include features similar to trocar actuator (231), connecting band portion (235), and trocar (230) described above. Trigger (504) is pivotably coupled to body (502) and is configured to actuate a driver actuator, similar to drive actuator (64, 314) described above, in order to fire a staple head assembly to simultaneously staple and sever tissue suitably captured between an anvil and staple head assembly in accordance with the teachings herein.

Additionally, actuator handle assembly (500) includes a multi-stage trocar actuation assembly (510). Trocar actuation assembly (510) includes a proximal frame (512), a multi-directional adjustment knob (520), a threaded shaft (524), an oblong washer (530), and locking bodies (540). As will be described in greater detail below, multi-directional adjustment knob (520) is configured to actuate in a first direction in order to drive trocar (508) between a sub-flush position and an open position. Additionally, multi-directional adjustment knob (520) is configured to actuate in a second direction in order to drive trocar (508) between the sub-flush position and a first closed position. Finally, multi-directional adjustment knob (520) is configured to actuate in a third direction in order to drive trocar (508) between the first closed position and a second closed position.

Similar to instrument (400) described above, it should be understood that in the sub-flush position, the distal end of trocar (508) is housed within a staple head assembly. Trocar (508) may be initially set at the sub-flush position during shipment of handle assembly (500) along with the rest of instrument, and prior suitable use thereof. Trocar (508) may be placed in the sub-flush position so that the distal end of trocar (508) is not inadvertently exposed or damaged prior to suitable use. In the open position, a distal end of trocar (508) may extend distally past staple head assembly such that trocar (508) may suitably couple with anvil in accordance with the teachings herein. The first closed position may correspond to a gap distance d between anvil and staple head assembly such that if driver actuator is fired is accordance with the teachings herein, staples (66) will form a suitable large staple height compression. Alternatively, the first closed position may correspond to a gap distance d between anvil and staple head assembly such that that anvil is slightly distal compared to the position required for staples (66) to form a suitable large staple height compression. In such instances, the operator may be required to proximally actuate trocar (508) and anvil from the first closed position by actuating multi-directional adjustment knob (520) in the third direction to achieve a suitable gap distance d corresponding with a large staple height compression. The second closed position may correspond to a gap distance d between anvil and staple head assembly such that if driver actuator is fired in accordance with the teachings herein, staples (66) will form a suitable small staple height compression.

Proximal frame (512) is attached to a proximal end of trocar (508) such that movement of proximal frame (512) results in movement of trocar (508). Proximal frame (512) is slidably disposed within body (502) such that proximal frame (512) may translate relative to body (502). However, proximal frame (512) is rotationally fixed within body (502) such that proximal frame (512) may not rotate about its own longitudinal axis. Proximal frame (512) may be rotational fixed and slidably coupled with body (502) via a pin and slot relationship, or any other suitable coupling that would be apparent to one of ordinary skill in the art in view of the teachings herein. Proximal frame (512) defines a threaded channel (514), proximal recess (516), and distal recess (518).

Proximal frame (512) is coupled with threaded shaft (524) via engagement between threaded channel (514) and a threaded portion (526) of shaft (524). Threaded shaft (524) extends from distal threaded portion (526), through a proximal end of body (502), through oblong washer (530), and terminates into a proximal end (525). Threaded shaft (524) couples with multi-directional adjustment knob (520) at proximal end (525) via pivotable coupling (528). Multi-directional adjustment knob (520) includes a handle (522). Adjustment knob (520) is configured to rotate threaded shaft (524) about the longitudinal axis of threaded shaft (524), as well as translate threaded shaft (524) relative to body (502). As will be described in greater detail below, rotation of threaded shaft (524) is configured to translate proximal frame (512) relative to both threaded shaft (524) and body (502), while translation of threaded shaft (524) is operable to translate proximal frame (512) and trocar (508) along with threaded shaft (524) relative to body (502).

Oblong washer (530) is biased proximally against multi-directional adjustment knob (520) by a biasing element (534), such as a spring. Biasing element (534) is housed within a proximal recess (505) defined by a proximally presented floor (507) and proximally presented annular shoulder (503) of body (502). Oblong washer (530) defines a through hole (532) that receives shaft (524). Oblong washer (530) is configured to rotate relative to shaft (524) and proximally presented annular shoulder (503) between an obstructed position (as shown in FIG. 25A) and an unobstructed position (as shown in FIG. 25B). When in the obstructed position, oblong washer (530) is positioned between annular shoulder (503) and multi-directional adjustment knob (520) such that oblong washer (530) prevents distal translation of adjustment knob (520) and shaft (524). When in the unobstructed position, oblong washer (530) is positioned within the perimeter of annular shoulder (503) such that oblong washer (530) does not prevent distal translation of adjustment knob (520) and shaft (524). As will be described in greater detail below, the operator may rotate oblong washer (530) into the unobstructed position in order to push multi-directional adjustment knob (520) distally, to thereby push shaft (524) and proximal frame (512) distally such that trocar (508) moves from the sub-flush position to the open position.

However, while oblong washer (530) is in the obstructed position, adjustment knob (520) and shaft (524) may still rotate about the longitudinal axis of shaft (524) in order to translate proximal frame (512) via the engagement between threaded channel (514) of proximal frame (512) and threaded portion (526) of shaft (524). Additionally, while oblong washer (530) is in the obstructed position, adjustment knob (520) may still rotate about pivotable coupling (528) in order to cam against oblong washer (530) to translate shaft (524), proximal frame (512), and trocar (508) proximally. As will be described in greater detail below, adjustment knob (520) may rotate shaft (524) about the longitudinal axis of shaft (524) to actuate trocar (508) between the sub-flush position and the first closed position, while adjustment knob (520) may then rotate about pivotable coupling (528) to cam against oblong washer (530) to further actuate trocar (508) between the first closed position and the second closed position.

Locking bodies (540) are slidably coupled with a portion of body (502). Locking bodies (540) are longitudinally fixed relative to body (502) but may actuate transversely relative to body (502) in order to selectively couple with recesses (516, 518) of proximal frame (512). Because locking bodies (540) are longitudinally fixed relative to body (502), when locking bodies (540) are within recesses (516, 518), locking bodies (540) help maintain the longitudinal location of proximal frame (512), as well as trocar (508), relative to body (502). In particular, when locking bodies (540) are within distal recess (518), proximal frame (512) and trocar (508) are located in the sub-flush position. When locking bodies (540) are within proximal recess (516), proximal frame (512) and trocar (508) are located in the open position. Locking bodies (540) are biased against proximal frame (512) via bias elements such as springs (542). Locking bodies (540) may be configured to actuate transversally out of recesses (516, 518) when the operator provides sufficient longitudinal force on proximal frame (512) to overcome the bias force of springs (542), thereby actuating locking bodies (540) out of recesses (516, 518).

Figure 24C:
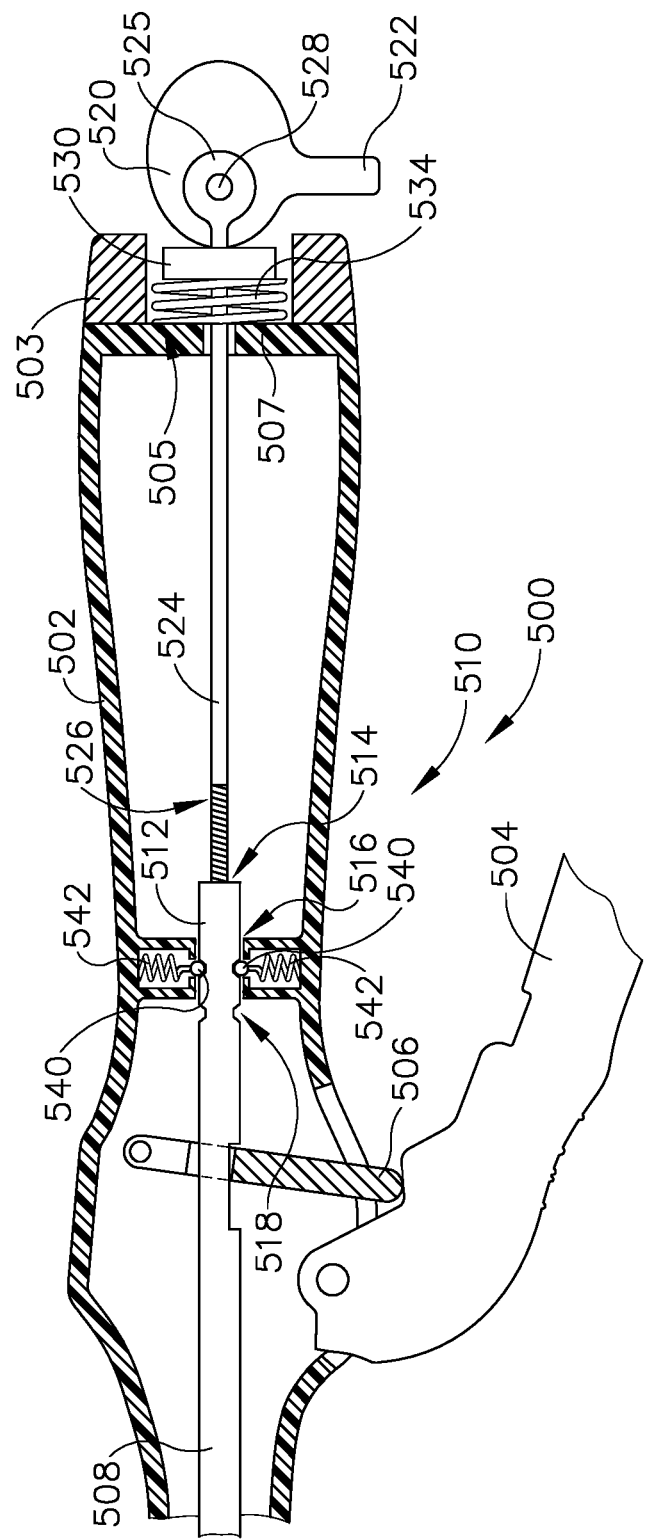
FIG. 24C depicts a cross-sectional side view of the actuator handle assembly of FIG. 24A, where the trocar actuation assembly is in a second configuration associated with the trocar in an open position, where the oblong washer is in an unobstructed position.

When the operator wants to actuate trocar (508) from sub-flush position (as shown in FIGS. 24A-24B) toward the open position (as shown in FIG. 24C), the operator may rotate oblong washer (530) from the obstructed position (as shown in FIG. 25A) to the unobstructed position (as shown in FIG. 25B). With oblong washer (530) in the unobstructed position, the operator may push multi-directional adjustment knob (520) distally such that oblong washer (530) actuates distally within recess (505) and compresses biasing element (534). In response, shaft (524) actuates distally within body (502). Because shaft (524) is coupled with proximal frame (512) via meshing of threaded channel (514) and threaded portion (526), proximal frame (512) and trocar (508) also actuate distally with shaft (524). Locking body (540) disengage with distal recess (518) and engage with proximal recess (516). At this moment, as shown in FIG. 24C, the operator may release multi-directional adjustment knob (520). It should be understood that force provided by springs (542) biasing locking bodies (540) into proximal recess (516) is stronger than the proximal biasing force of biasing element (534) on oblong washer (530). Therefore, locking bodies (540) and proximal recess (516) help trocar (508) remain in the open position so the operator may suitably couple distal end of trocar (508) with an anvil in accordance with the description above.

Figure 24D:
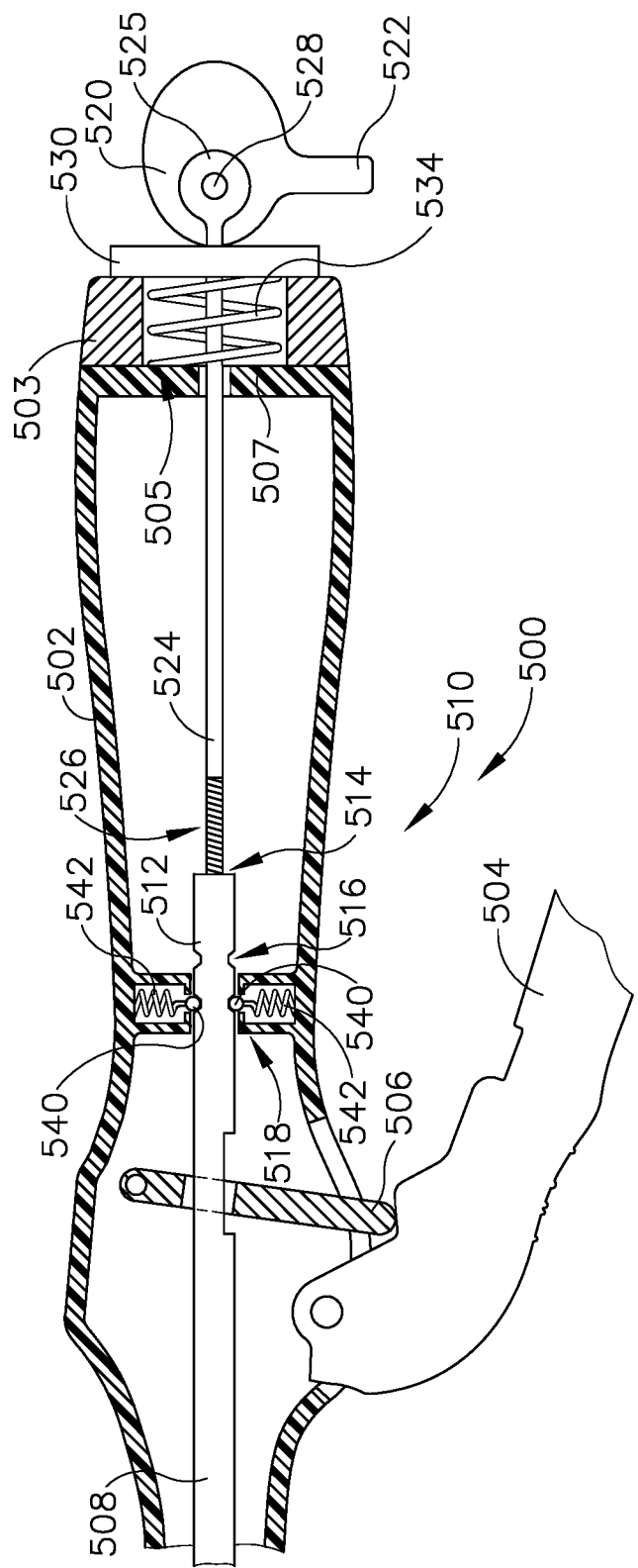
FIG. 24D depicts a cross-sectional side view of the actuator handle assembly of FIG. 24A, where the trocar actuation assembly is returned to in the first configuration associated with the trocar in the pre-deployed position, where the oblong washer is in the obstructed position.

As shown between FIGS. 24C and 24D, one trocar (508) has been suitable coupled with the anvil, the operator may pull multi-directional adjustment knob (520) proximally such that locking bodies (540) are driven out of engagement with proximal recesses (516) and into engagement with distal recess (518), thereby driving trocar (508) back to the sub-flush position. As this moment, the operator may rotate oblong washer (530) back in the obstructed position.

Figure 24E:
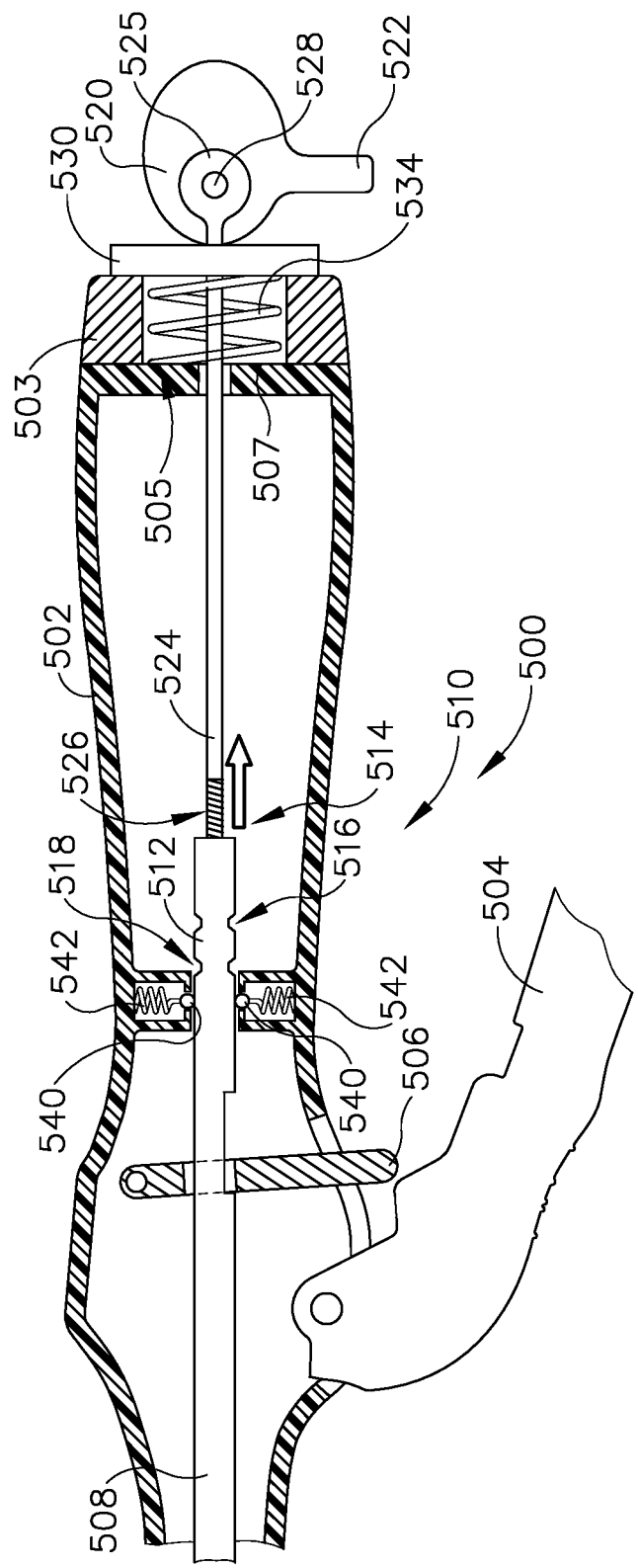
FIG. 24E depicts a cross-sectional side view of the actuator handle assembly of FIG. 24A, where the trocar actuation assembly is in a third configuration associated with the trocar in a first closed position, where the oblong washer is in the obstructed position.

Next, as shown between FIGS. 24D and 24E, the operator may rotate adjustment knob (520) and shaft (524) about the longitudinal axis of shaft (524). Because proximal frame (512) is slidably housed and rotationally constrained within body (502), when threaded shaft (524) meshes with threaded channel (514), rotation of threaded shaft (524) drives translation of proximal frame (512), and therefore drives translation of trocar (508). Therefore, the operator may rotate adjustment knob (520) in the first angular direction to urge proximal frame (512) and trocar (508) proximally toward the first closed position. Conversely, the operator may rotate adjustment knob (490) in the second angular direction to urge proximal frame (512) and trocar (508) distally toward the sub-flush position.

Figure 24F:
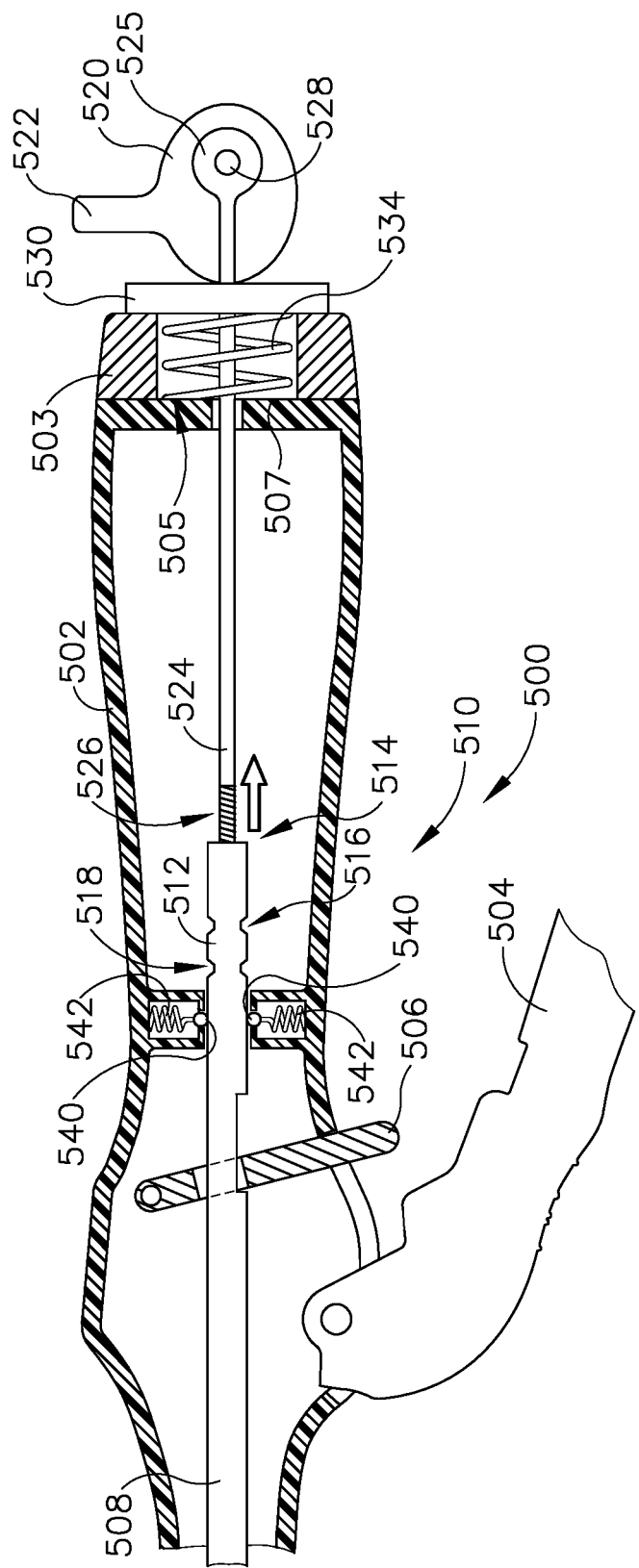
FIG. 24F depicts a cross-sectional side view of the actuator handle assembly of FIG. 24A, where the trocar actuation assembly is in a fourth configuration associated with the trocar in a second closed position, where the oblong washer is in the obstructed position.

Next, as shown between FIGS. 24E and 24F, the operator may rotate adjustment knob (520) about pivotable coupling (528) in order to cam adjustment knob (520) against oblong washer (530). As the exterior of adjustment knob (520) cams against oblong washer, shaft (524) is driven proximally. Because shaft (524) meshes with proximal frame (512), proximal translation of shaft (524) also drives proximal frame (512) and trocar (508) proximally to the second closed position. If the operator wishes to actuate trocar (508) from the second closed position to the first closed position, the operator may rotate adjustment knob (520) about pivotable coupling (528) in the opposite direction, thereby distally driving shaft (524), proximal frame (512) and trocar (508) in accordance with the description herein While in the current example, adjustment knob (520) rotates about the longitudinal axis of shaft (524) to drive trocar (508) from the sub-flush position to the first closed position, and adjustment knob (520) rotates about pivotable coupling (528) to drive trocar (508) from the first closed position to the second closed position, these two functionalities may be easily reversed. Therefore, rotation of adjustment knob (520) about pivotable coupling (528) may be used to actuate trocar from the sub-flush position to the first closed position, while rotation of adjustment knob (520) about the longitudinal axis of shaft (524) may be used to actuate trocar between the first closed position and the second closed position.

FIGS. 26A-26D show another alternative actuator handle assembly (550) that may be readily incorporated into instrument (10) described above. While not explicitly described below, actuator handle assembly (550) may have various features and functionality described above for instrument (10). Therefore, actuator handle assembly (550) is substantially similar to actuator handle assembly (70) described above, with differences elaborated below.

Actuator handle assembly (550) includes a body (552), a trigger (554), and a lockout feature (556); which may be substantially similar to body (72), trigger (74), and lockout feature (82) described above, respectively, with differences elaborated below. A trocar (558) extends proximally within body (522). Trocar (558) may be substantially similar to trocar (230) described above, with differences elaborated below. While not explicitly shown, trocar (558) may include features similar to trocar actuator (231), connecting band portion (235), and trocar (230) described above. Trigger (554) is pivotably coupled to body (552) and is configured to actuate a driver actuator, similar to drive actuator (64, 314) described above, in order to fire a staple head assembly to simultaneously staple and sever tissue suitably captured between an anvil and staple head assembly in accordance with the teachings herein.

Figure 26A:
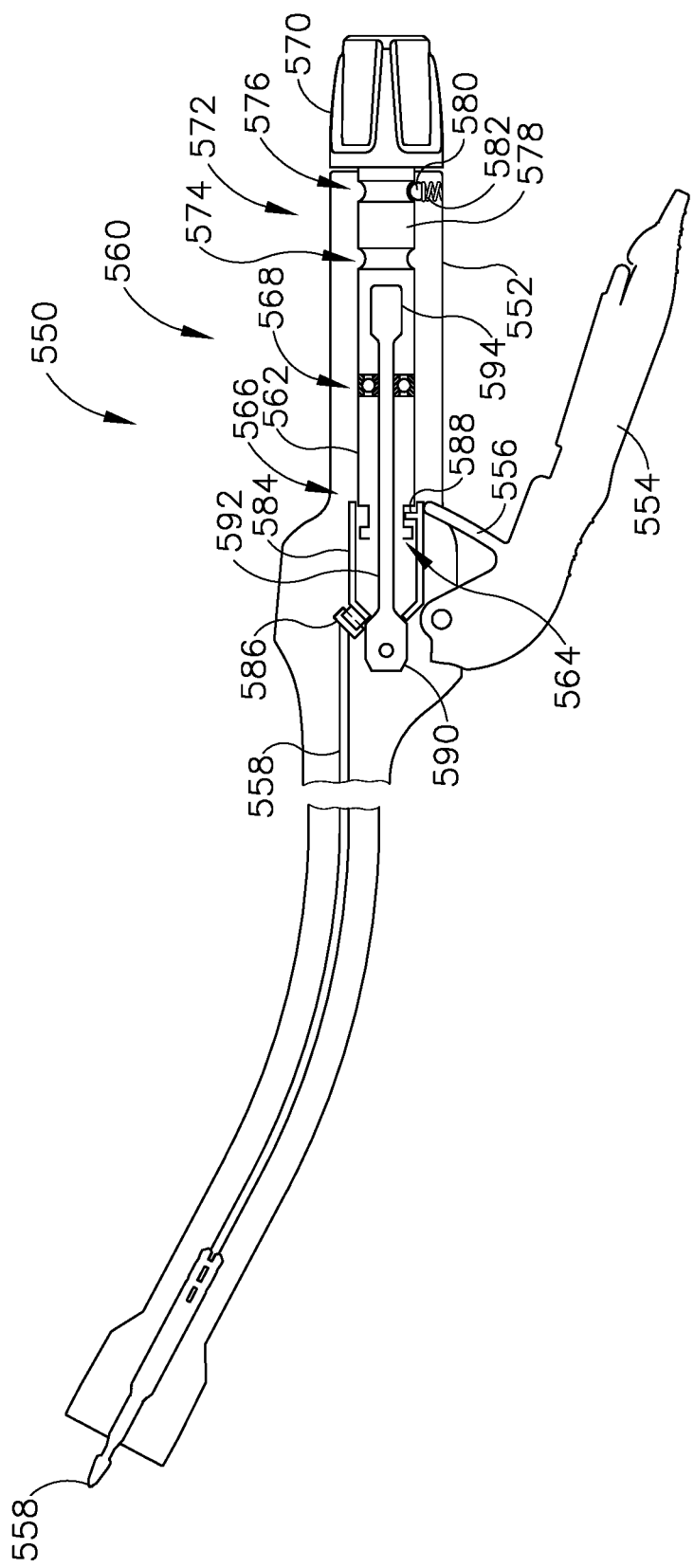
FIG. 26A depicts a cross-sectional side view of an alternative actuator handle assembly, where a trocar actuation assembly is in a first configuration associated with an anvil in an open position.
Figure 26B:
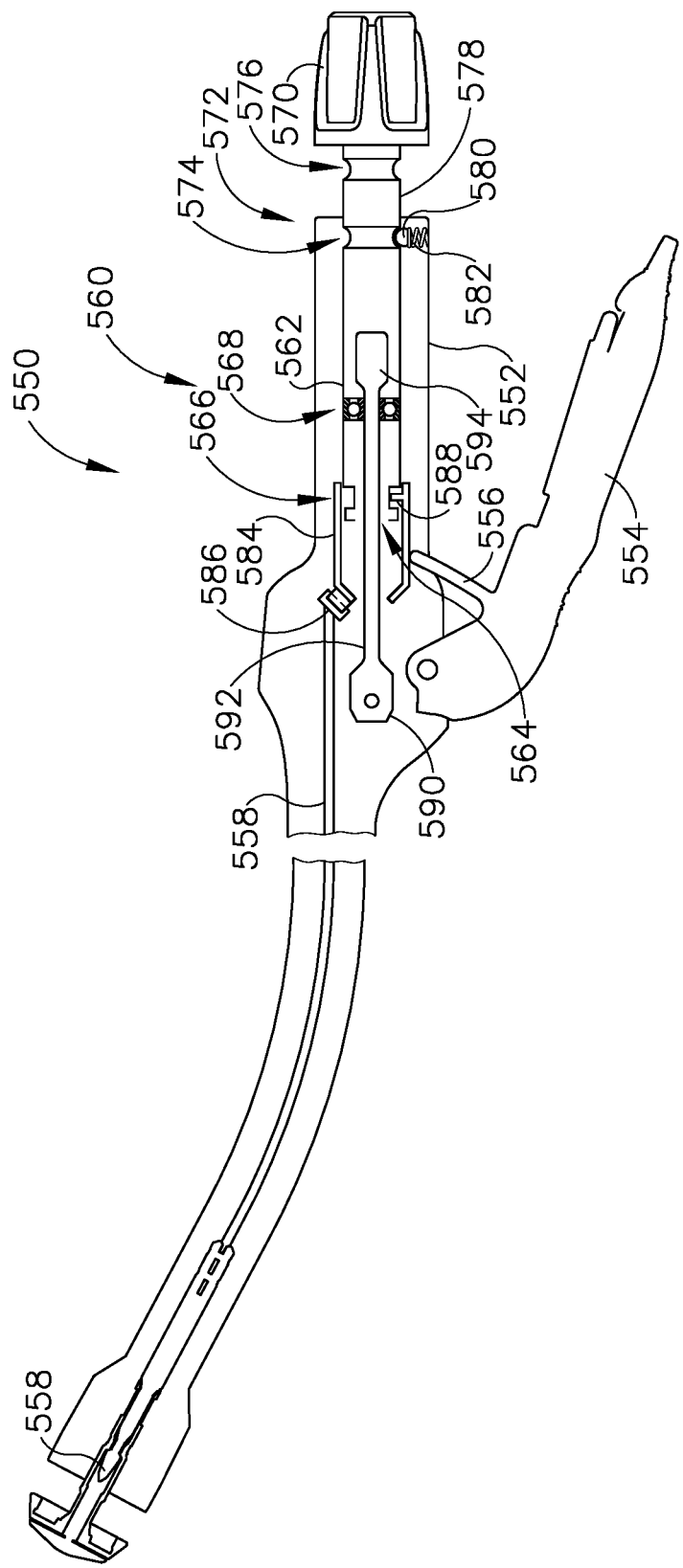
FIG. 26B depicts a cross-sectional side view of the actuator handle assembly of FIG. 26A, where the trocar actuation assembly is in a second configuration associated with the anvil in a first closed position.

Additionally, actuator handle assembly (550) includes a multi-stage trocar actuation assembly (560). Trocar actuation assembly (560) includes a hollow distal shaft (562), a rolling ring bearing assembly (568), an adjustment knob (570), a proximal shaft portion (572), a locking body (580), a coupling body (584), and a fixed shaft (590). As will be described in greater detail below, adjustment knob (570) may be pulled from a distal position (as shown in FIG. 26A) to a proximal position (as shown in FIG. 26B), in order to actuate trocar (558) from the open position to the first closed position. As will also be described in greater detail below, adjustment knob (570) may rotate about its own longitudinal axis in order to actuate trocar (558) between the first closed position and the second closed position.

Adjustment knob (570), proximal shaft portion (572), hollow distal shaft (562), and rolling ring bearing assembly (568) are connected to each other and configured to rotate about their longitudinal axis relative to body (552) and translate relative to body (552). Hollow distal shaft (562) defines an open distal end (564) a distal annular recess (566). Open distal end (564) is dimensioned to receive a proximal portion of fixed shaft (590). Rolling ring bearing assembly (568) is located on the interior of hollow distal shaft (562). As will be described in greater detail below, rolling ring bearing assembly (568) is configured to engage a large diameter, drive shaft section (594) of fixed shaft (590) such that rotation of rolling ring bearing assembly (568) around drive shaft section (594) causes adjustment knob (570), proximal shaft portion (572), hollow distal shaft (562), and rolling ring bearing assembly (568) to translate distally and proximally relative to drive shaft section (594).

Coupling body (584) couples trocar (558) with hollow distal shaft (562). In particular, coupling body (584) includes a trocar coupling end (586) and a shaft coupling end (588). Trocar coupling end (586) is fixedly attached to trocar (558), while shaft coupling end (588) is rotatably attached to hollow distal shaft (562) via distal annular recess (566). Therefore, hollow distal shaft (562) may translate with coupling body (584) and trocar (558), while also rotating relative to coupling body (584) and trocar (558). Coupling body (584) has a through hole such that fixed shaft (590) may extend through coupling body (584). Additionally, coupling body (584) is dimensioned to interfere with lockout feature (556) when trocar (558) is positioned such that gap distance d is not within the desired operating range.

Proximal shaft portion (572) includes a distal annular recess (574), a proximal annular recess (576), and an intermediate portion (578) extending between recesses (574, 576). Locking body (580) is biased toward proximal shaft portion (572) via bias spring (582). Locking body (580) is longitudinally fixed relative to body (552) but may actuate transversely relative to body (552) in order to selectively couple with recesses (574, 576) of proximal shaft portion (572). Because locking body (580) is longitudinally fixed relative to body (552), when locking body (580) is within recesses (574, 576), locking body (580) helps maintain the longitudinal location of proximal shaft portion (572), as well as coupling body (584) and trocar (558), relative to body (552). In particular, when locking body (580) is within proximal annular recess (576), trocar (558) is located in the open position. When locking body (580) is within distal annular recess (574), trocar (558) is located in the open position. Locking body (580) may be configured to actuate transversally out of recesses (574, 576) when the operator provides sufficient longitudinal force on proximal shaft portion (572) to overcome the bias force of springs (582), thereby actuating locking body (580) out of recesses (574, 576).

Fixed shaft (590) is attached to body (552). Fixed shaft (590) includes a small diameter section (592) and large diameter, drive shaft section (594). Small diameter section (592) is dimensioned such that small diameter section (592) is directly adjacent to rolling ring bearing assembly (568), small diameter section (592) does not engage rolling ring bearing assembly (568). Drive shaft section (594) is dimensioned such that when drive shaft section (594) is within the confines of rolling ring bearing assembly (568), rotation of rolling ring bearing assembly (568) around drive shaft section (594) causes rolling ring bearing assembly (568) to longitudinally actuate adjustment knob (570), proximal shaft portion (572), hollow distal shaft (562), and rolling ring bearing assembly (568). Longitudinal actuation of adjustment knob (570), proximal shaft portion (572), hollow distal shaft (562), and rolling ring bearing assembly (568) causes longitudinal actuation of coupling body (584) as well as trocar (558). In other words, rolling ring bearing assembly (568) and drive shaft section (594) act as a threadless rod and rolling ring bearing assembly.

FIG. 26A shows trocar actuation assembly (560) in the position associated with trocar (558) in the open position. In the open position, locking body (580) is engaged with proximal annular recess (576) in order to help keep trocar (558) in the open position. At this point, lockout feature (556) is blocked by coupling body (584), preventing firing of trigger (554). Additionally, in the open position, small diameter section (592) of fixed shaft (590) is within the confines of rolling ring bearing assembly (568). Therefore, if the operator rotates adjustment knob (570) at the position shown in FIG. 26A, trocar (558) will not actuate due to rotation of rolling ring bearing assembly (568).

After the operator has suitably coupled the distal end of trocar (558) with an anvil in accordance with the description above, the operator may pull on adjustment knob (570) in order to translate adjustment knob (570), proximal shaft portion (572), hollow distal shaft (562), and rolling ring bearing assembly (568) to the position shown in FIG. 26B. Pulling adjustment knob (570) with sufficient force will cause translation of proximal shaft portion (572) to disengage locking body (580) from proximal annular recess (576). Locking body (580) will ride on intermediate portion (578) of proximal shaft portion (572) until locking body (580) enters distal annular recess (574) in order to help keep trocar (558) in the first closed position. At this point, lockout feature (556) is still blocked by coupling body (584), preventing firing of trigger (554). Additionally, in the first closed position, a distal portion of drive shaft section (594) starts to enter the confines of rolling ring bearing assembly (568). Therefore, if the operator rotates adjustment knob (570) in one angular direction, rolling ring bearing assembly (568) will grip drive shaft section (594) and begin to proximally actuate trocar (558). However, if the operator rotates adjustment knob (570 in the opposite angular direction, rolling ring bearing assembly (568) will not grip drive shaft section (594) such that trocar (558) remains stationary.

Figure 26C:
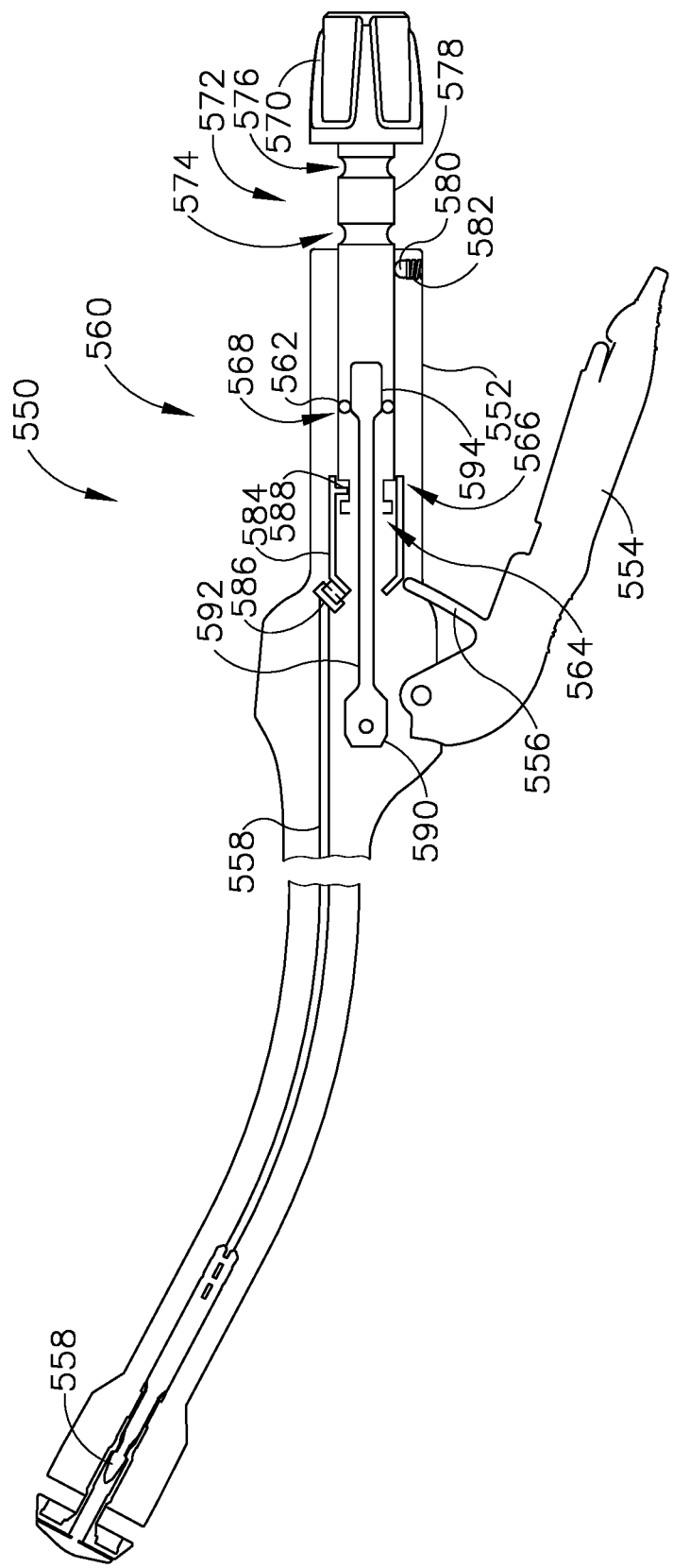
FIG. 26C depicts a cross-sectional side view of the actuator handle assembly of FIG. 26A, where the trocar actuation assembly is in a third configuration associated with the anvil in a second closed position.
Figure 26D:
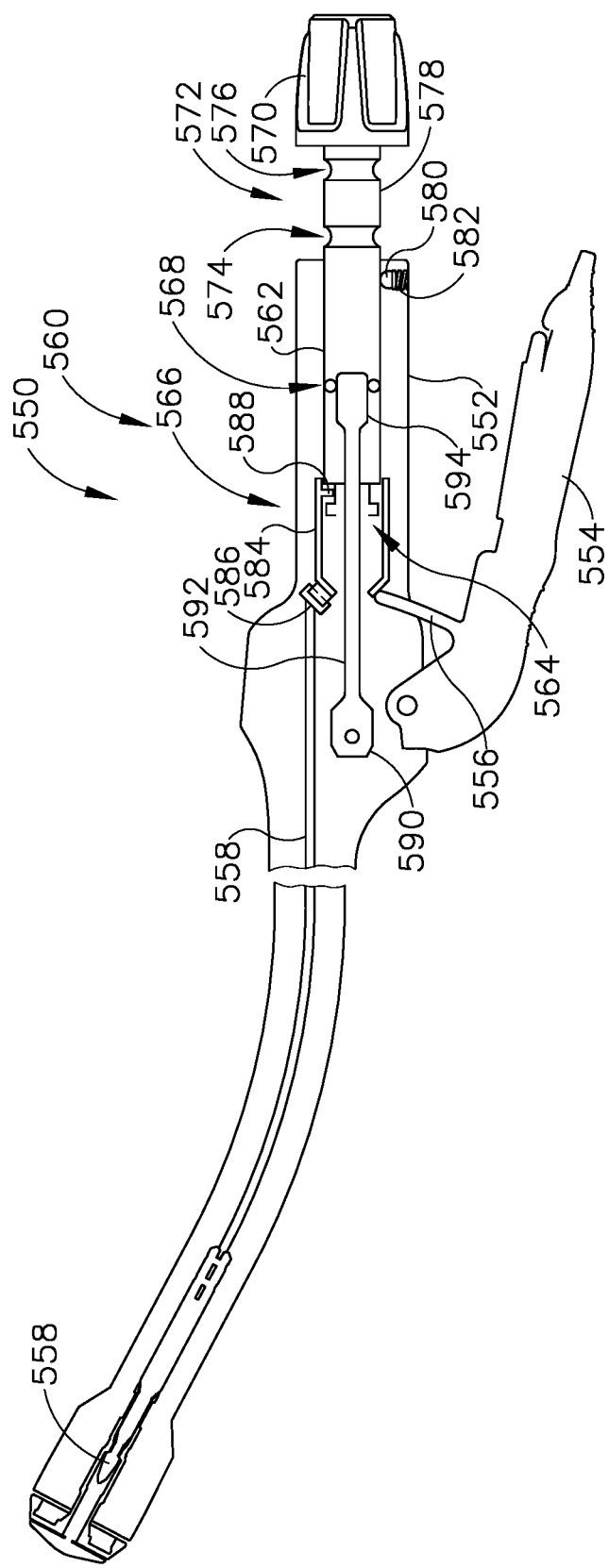
FIG. 26D depicts a cross-sectional side view of the actuator handle assembly of FIG. 26A, where the trocar actuation assembly is in a third configuration associated with the anvil in a second closed position and a trigger is pivoted to a fired position.

FIG. 26C shows trocar actuation assembly (560) after adjustment knob (570) has been sufficiently rotated to drive trocar (558) in the second closed position. At this movement, coupling body (584) no longer obstructs lockout feature (556) such that the operator may fire trigger (554) is desired. It should be understood that lockout feature (556) may be unobstructed prior to reaching the second closed position. Lockout feature (556) may be unobstructed at any time when gap distance d is within the desired operating range. Next, as shown in FIG. 26D, the operator may fire trigger (554) to simultaneously staple and sever tissue in accordance with the description herein.

Figure 28:
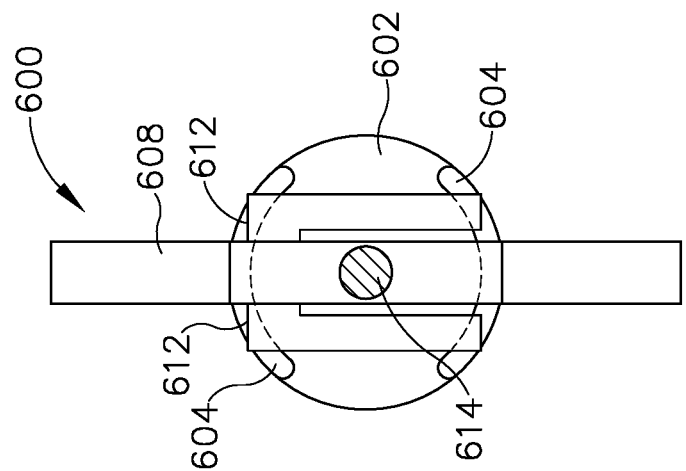
FIG. 28 depicts a cross-sectional view of the adjustment knob assembly of FIG. 27, taken along line 28-28 of FIG. 27.
Figure 27:
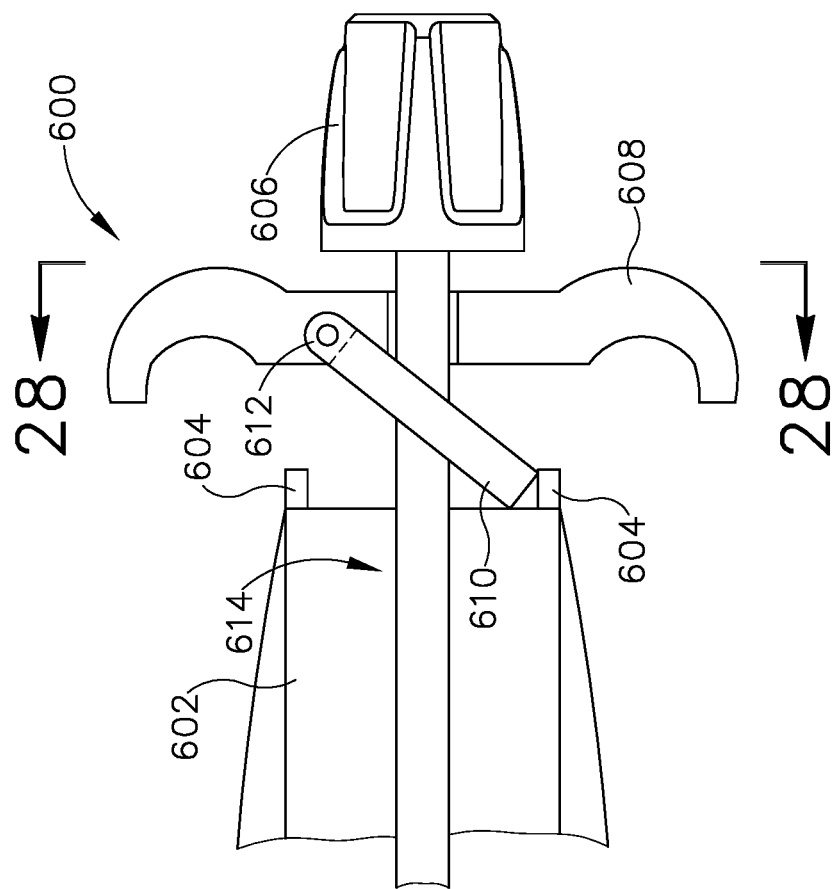
FIG. 27 depicts an alternative adjustment knob assembly that may be readily incorporated into the actuator handle assembly of FIG. 26A.
Figure 29:
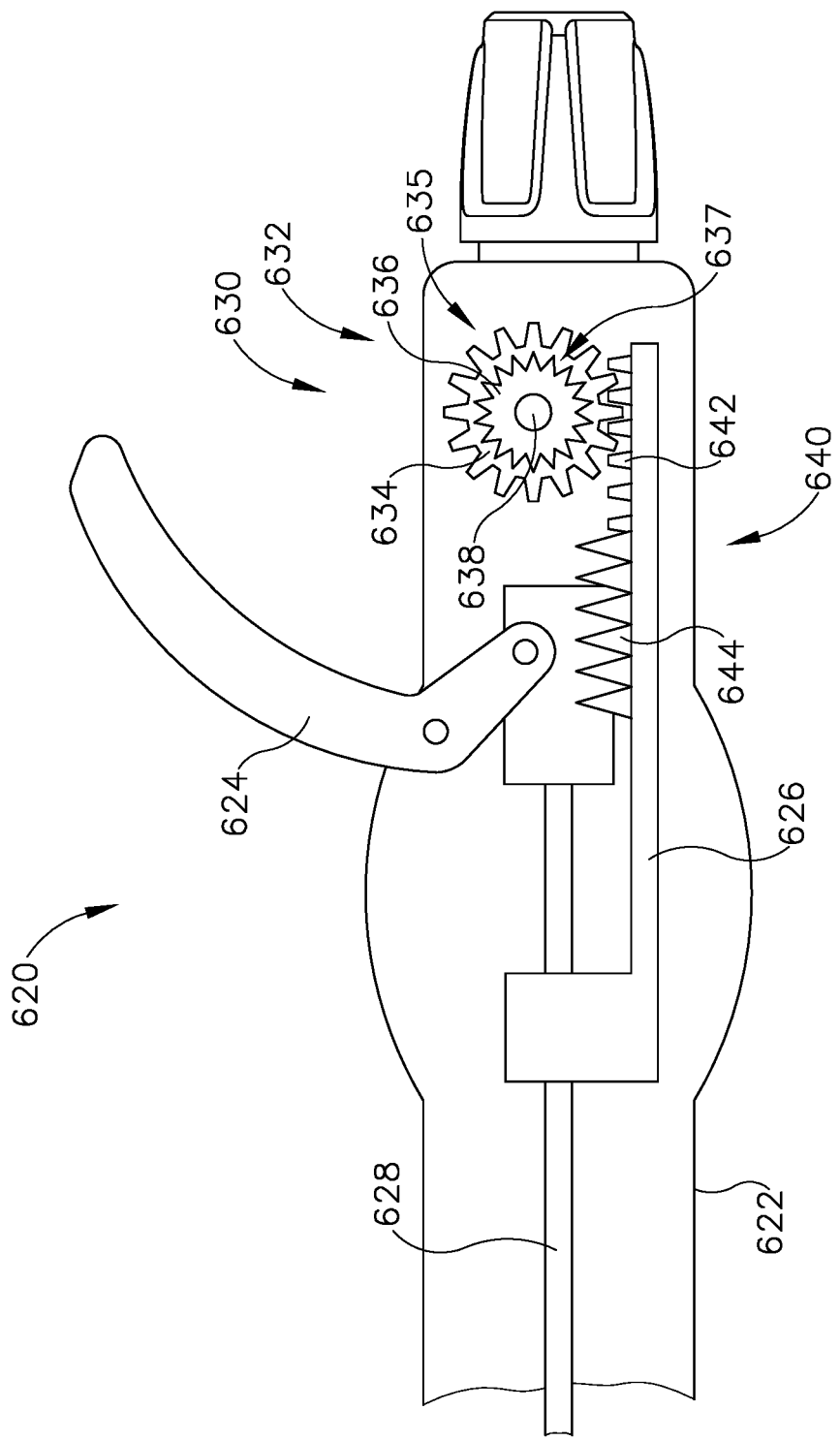
FIG. 29 depicts a cross-sectional side view of an alternative actuator handle assembly.
Figure 30:
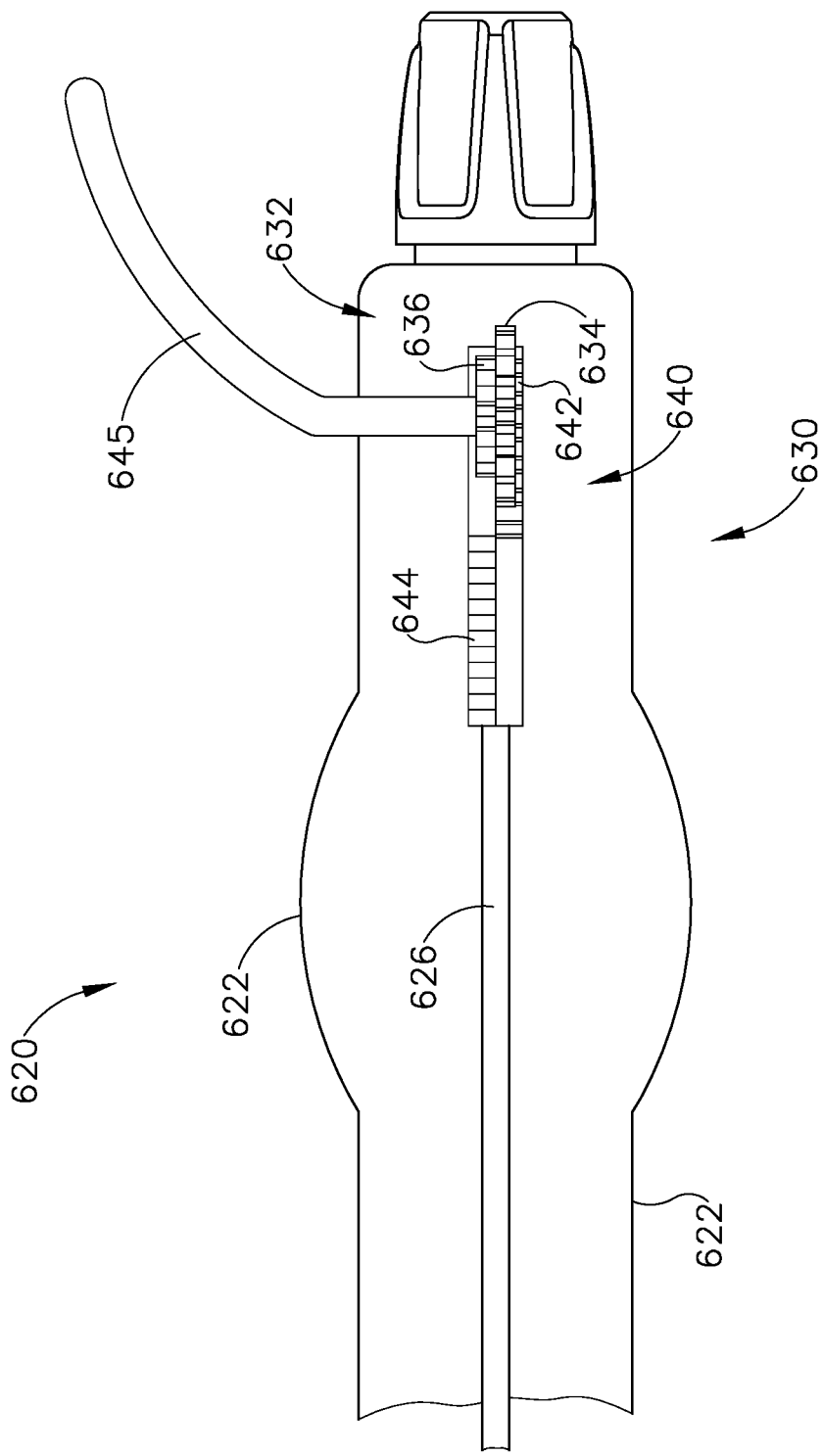
FIG. 30 depicts a cross-sectional top view of the actuator handle assembly of FIG. 29.
Figure 31B:
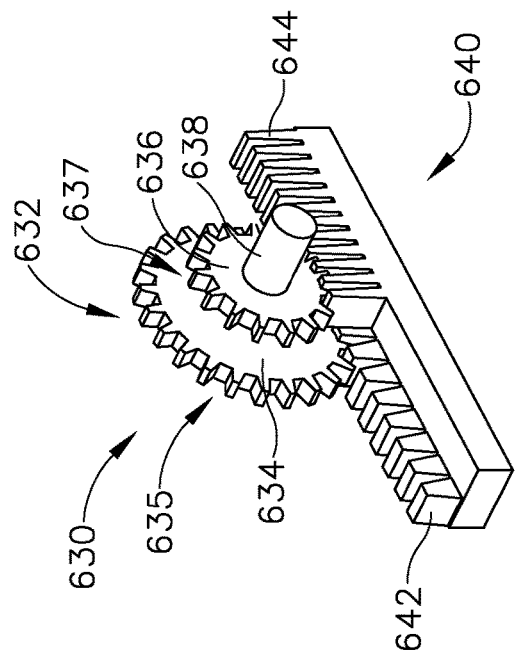
FIG. 31B depicts a perspective view of the trocar actuation assembly in a second configuration associated with the trocar in a first closed position.
Figure 32:
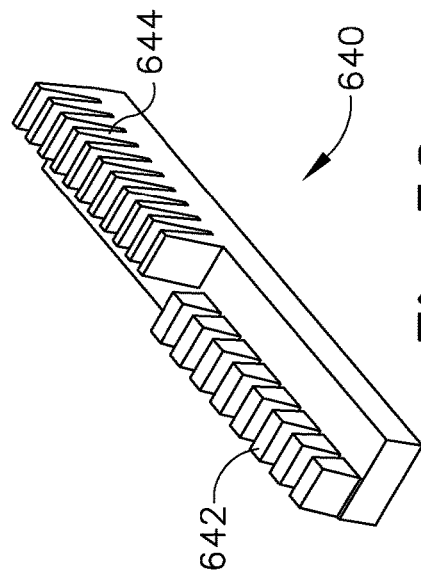
FIG. 32 depicts a perspective view of a rack assembly of the trocar actuation assembly of FIG. 31A.
Figure 31A:
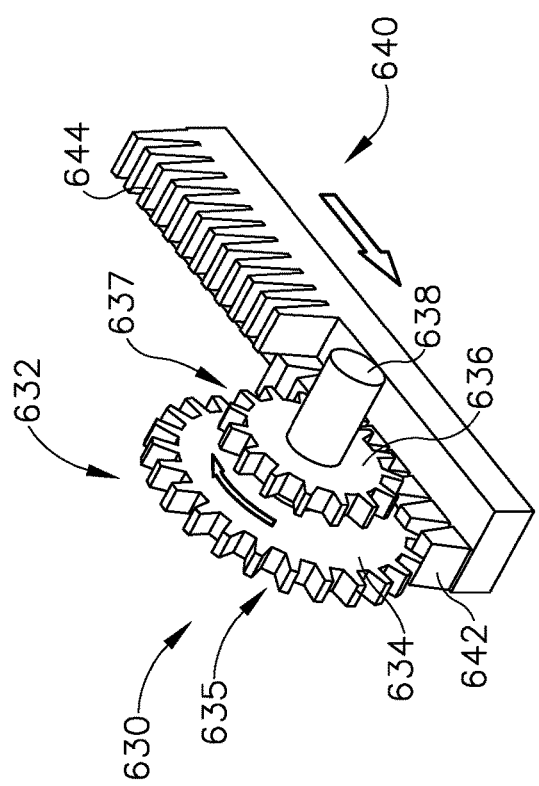
FIG. 31A depicts a perspective view of a trocar actuation assembly in a first configuration associated with a trocar in an open position.
Figure 31C:
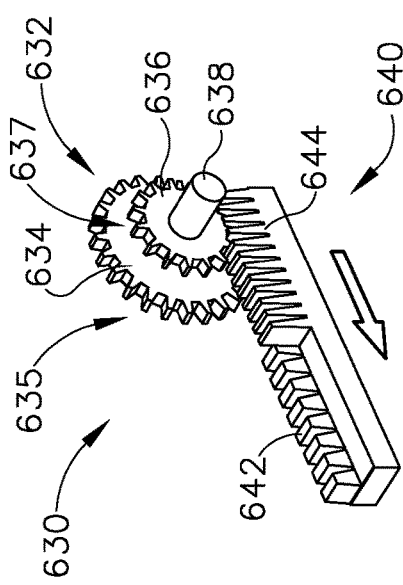
FIG. 31C depicts a perspective view of the trocar actuation assembly in a second configuration associated with the trocar in a second closed position.

FIGS. 27-28 show an alternative adjustment knob assembly (600) that may be readily incorporated into trocar actuation assembly (560) described above. In particular, instead of having a locking body (580) biased into annular recesses (574, 576), adjustment knob assembly (600) has a kickstand (610) to help keep adjustment knob (606) in the first closes position. Adjustment knob assembly (600) includes a proximal body (602), a pair of proximal shoulders (604), an adjustment knob (606), a translation bar (608), a kickstand (610) pivotably coupled with translation bar (608) via a pivot pin (612), and a proximal shaft portion (614) extending from adjustment knob (606). Adjustment knob (606) and proximal shaft portion (614) may be substantially similar to adjustment knob (570) and proximal shaft portion (572) described above respectively.

In exemplary use, the operator may pull on translation bar (608) in order to actuate knob (606) and shaft (614) to a position associated with a trocar in the first closed position. The operator may then pivot kickstand (610) onto shoulder (604) in order to help keep trocar in the first position.

D. Exemplary Dual Stage Trocar Actuation Assemblies Having Compound Rack and Pinion Mechanisms FIGS. 29-32 show an exemplary alternative actuator handle assembly (620) that may be readily incorporated into instrument (10) described above. While not explicitly described below, actuator handle assembly (620) may have various features and functionality described above for instrument (10). Therefore, actuator handle assembly (620) is substantially similar to actuator handle assembly (70) described above, with differences elaborated below.

Actuator handle assembly (620) includes a body (622), and a trigger (624); which are substantially similar to body (72), and a trigger (74) described above, respectively, with differences elaborated below. Therefore, trigger (624) is operable to actuate a driver actuator (628) in order to simultaneously staple and sever tissue in accordance with the description above. Actuator handle assembly (620) also includes a trocar actuation assembly (630). As will be described in greater detail below, trocar actuation assembly (630) is configured to actuate a trocar (626) between an open position, a first closed position, and a second closed position. Trocar (626) may be substantially similar to trocar (230) described above. While not explicitly shown, trocar (626) may include features similar to trocar actuator (231), connecting band portion (235), and trocar (230) described above.

Trocar actuation assembly (630) includes a pinion assembly (632), a rack assembly (640), and a side crank (645). Pinion assembly (632) includes a large pinion (634) having course teeth (635), a small pinion (636) have fine teeth (637), and a pin (638). Large pinion (634) and small pinion (636) are rotatably coupled with body (622) via pin (638) and are configured to rotate unitarily with each other. In other words, large pinion (634) and small pinion (636) are fixed relative to each other. Side crank (645) is configured to rotate pinion assembly (632). Rack assembly (640) is attached to trocar (626) such that translation of rack assembly (640) causes translation of trocar (626). Rack assembly (640) includes a coarse rack (642) and a fine rack (644). Coarse rack (642) is configured to mesh with coarse teeth (635) of large pinion (634), while fine rack (644) is configured to mesh with fine teeth (637) of small pinion (636). Coarse rack (642) meshes with large pinion (634) when trocar (626) travels between the open position and the first closed position, while fine rack (644) is disengaged with small pinion (636) when trocar (626) travels between the open position and the first closed position. Conversely, fine rack (644) meshes with small pinion (636) when trocar (626) travels between the first closed position and the second closed position, while coarse rack (642) is disengaged with large pinion (634) when trocar (626) travels between the first closed position and the second closed position. Therefore, angular displacement of side crank (645) causes greater displacement of trocar (626) when trocar (626) travels between the open position and the first closed position; while the same angular displacement of side crank (645) causes a smaller displacement of trocar (626) when trocar (626) travels between the first closed position and the second closed position. While a side crank (645) is used to rotate pinion assembly (632), any other suitably input mechanism may be used as would be apparent to one having ordinary skill in the art in view of the teachings herein. For instance, a rotary motor may be used.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a handle assembly comprising a body; (b) a shaft assembly comprising an outer tubular member extending distally from the body; (c) an end effector comprising: (i) a staple deck fixed relative to the outer tubular member, (ii) a staple driver, wherein the staple driver is operable to actuate relative to the staple deck between an unfired position and a fired position, and (iii) a trocar configured to actuate relative to the staple deck and the staple driver; (d) an anvil configured to selectively couple with the trocar, wherein the trocar is operable to actuate the anvil relative to the staple deck when the anvil is selectively coupled with the trocar; (e) a first trocar closure assembly configured to actuate in a first motion relative to the body in order to drive the trocar between a distal position and a first closed position; and (f) a second trocar closure assembly configured to actuate in a second motion relative to the body in order to drive the trocar between the first closed position and a second closed position, wherein the second closed position is proximal relative to both the first closed position and the distal position, wherein the staple driver is configured to remain inoperable at least until the first trocar closure assembly actuates the trocar to the first closed position.

Example 2

The apparatus of Example 1, wherein the second trocar actuation assembly is configured to remain disengaged within the trocar until the trocar reaches the first closed position.

Example 3

The apparatus of any one or more of Examples 1 through 2, wherein the second trocar actuation assembly is configured to actuate the trocar between a plurality of positions located between the first closed position and the second closed position.

Example 4

The apparatus of any one or more of Examples 1 through 3, wherein the first trocar closure assembly is configured to actuate the trocar at a first rate of movement, wherein the second trocar closure assembly is configured to actuate the trocar at a second rate of movement, wherein the first rate of movement is greater than the second rate of movement.

Example 5

The apparatus of any one or more of Examples 1 through 4, wherein the trocar comprises a proximal frame slidably housed within the body.

Example 6

The apparatus of Example 5, wherein the proximal frame is slidably housed within the body through a pin and slot relationship.

Example 7

The apparatus of Example 5, wherein the first trocar closure assembly comprises a handle pivotably coupled with the body.

Example 8

The apparatus of Example 7, wherein the handle is also coupled with the proximal frame.

Example 9

The apparatus of Example 8, wherein the handle defines a slot, wherein the proximal frame comprises a projection, wherein the projection is slidably housed within the slot.

Example 10

The apparatus of Example 7, wherein the first closure assembly further comprises a coupling link, wherein the coupling link is coupled to both the handle and the proximal frame.

Example 11

The apparatus of Example 10, wherein the handle defines a slot, wherein the coupling link comprises a pin, wherein the pin is slidably housed within the slot.

Example 12

The apparatus of Example 5, wherein the second trocar closure assembly comprises an adjustment knob rotatably disposed on the body.

Example 13

The apparatus of Example 12, wherein the second trocar closure assembly comprises a threaded shaft extending from the adjustment knob into the body.

Example 14

The apparatus of Example 13, wherein the proximal frame defines a coupling channel, wherein the threaded shaft is configured to engage the coupling channel when the trocar is between the first closed position and the second closed position.

Example 15

The apparatus of Example 5, wherein the trocar is biased toward the first closed position.

Example 16

An apparatus, comprising: (a) a handle assembly comprising a body; (b) a shaft assembly comprising an outer tubular member extending distally from the body; (c) an end effector comprising: (i) a staple deck fixed relative to the outer tubular member, (ii) a staple driver, wherein the staple driver is operable to actuate relative to the staple deck between an unfired position and a fired position, and (iii) a trocar configured to actuate relative to the staple deck and the staple driver; (d) an anvil configured to selectively couple with the trocar, wherein the trocar is operable to actuate the anvil relative to the staple deck when the anvil is selectively coupled with the trocar; (e) a first trocar closure assembly comprising a first actuating body, wherein the first actuating body is configured to actuate the trocar between a distal position and a first closed position; and (f) a second trocar closure assembly comprising a second actuating body, wherein the second actuating body is configured to actuate the trocar between the first closed position and a second closed position, wherein the second actuating body is configured to disengage the trocar while the trocar is between the distal position and the first closed position.

Example 17

The apparatus of Example 16, wherein the first actuating body is configured to translate relative to the body.

Example 18

The apparatus of Example 17, wherein the second actuating body is fixed with the trocar.

Example 19

The apparatus of any one or more of Examples 16 through 18, wherein the first actuating body is configured to pivot relative to the body.

Example 20

An apparatus, comprising: (a) a handle assembly comprising a body; (b) a shaft assembly comprising an outer tubular member extending distally from the body; (c) an end effector comprising: (i) a staple deck fixed relative to the outer tubular member, (ii) a staple driver, wherein the staple driver is operable to actuate relative to the staple deck between an unfired position and a fired position, and (iii) a trocar configured to actuate relative to the staple deck and the staple driver; (d) an anvil configured to selectively couple with the trocar, wherein the trocar is operable to actuate the anvil relative to the staple deck when the anvil is selectively coupled with the trocar; and (e) a trocar closure system comprising an adjustment body, wherein the trocar closure system is configured to actuate the trocar between a distal position, a first closed position, and a second closed position, wherein the adjustment body is configured to actuate in a first motion to drive the trocar between the distal position and the first closed position, wherein the adjustment body is configured to actuate in a second motion to drive the trocar between the first closed position and the second closed position.

IV. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 16/159,848, entitled "Latch to Prevent Back-Driving of Circular Surgical Stapler," filed on Oct. 15, 2018, issued as U.S. Pat. No. 11,051,819 on Jul. 6, 2021; and U.S. application Ser. No. 16/159,854, entitled "Dual Lever to Reduce Force to Fire in Circular Surgical Stapler," filed on Oct. 15, 2018, issued as U.S. Pat. No. 11,134,952 on Oct. 5, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
   (a) a handle body;
   (b) a shaft assembly extending distally from the handle body;
   (c) a stapling assembly comprising:
      (i) a staple deck fixed relative to the shaft assembly,
      (ii) a staple driver, wherein the staple driver is operable to actuate relative to the staple deck between an unfired position and a fired position to drive a plurality of staples into tissue, and
      (iii) an elongated coupling member configured to actuate relative to the staple deck and the staple driver;
   (d) an anvil configured to selectively couple with the elongated coupling member, wherein the elongated coupling member is operable to actuate the anvil relative to the staple deck when the anvil is selectively coupled with the elongated coupling member; and
   (e) a closure system comprising an adjustment body and an elongated closure member extending distally from the adjustment body, wherein the elongated closure member is housed within the handle body, wherein the adjustment body is located proximally relative to the handle body, wherein the closure system is configured to actuate the anvil, while coupled to the elongated coupling member, between a distal position, a first closed position, and a second closed position, wherein the adjustment body is configured to rotate about a first axis to drive the anvil between the distal position and the first closed position, wherein the adjustment body is configured to rotate about a second axis to drive the anvil between the first closed position and the second closed position, wherein the first axis and the second axis extend in different directions and the first axis extends proximal to the handle body.

2. The apparatus of claim 1, wherein the staple driver is configured to actuate a plurality of staples against the anvil while actuating from the unfired position toward the fired position.

3. The apparatus of claim 2, wherein the anvil and the staple deck are configured to define a first gap distance associated with a first staple height compression while the elongated coupling member is coupled with the anvil in the first closed position.

4. The apparatus of claim 3, wherein the anvil and the staple deck are configured to define a second gap distance associated with a second staple height compression while the elongated coupling member is coupled with the anvil in the second closed position.

5. The apparatus of claim 2, wherein the distal position comprises a sub-flush position, wherein the adjustable body is configured to translate relative to the handle body in order to actuate the elongated coupling member distally from the sub-flush position toward an open position.

6. The apparatus of claim 5, wherein the closure assembly further comprises an oblong washer configured to actuate between an obstructed position and an unobstructed position, wherein the oblong washer is configured to inhibit the adjustable body from actuating the elongated coupling member into the open position in the obstructed position.

7. The apparatus of claim 6, wherein the oblong washer is configured to rotate between the obstructed position and the unobstructed position.

8. The apparatus of claim 2, wherein the adjustment body comprises a lever.

9. The apparatus of claim 2, wherein the closure assembly further comprises at least one locking body configured to engage a recess defined by the elongated coupling member in the distal position to thereby inhibit movement of the elongated coupling member out of the distal position.

10. The apparatus of claim 1, wherein the elongated closure system further comprises a threaded shaft extending along a longitudinal axis, wherein the adjustment body is pivotally coupled to the threaded shaft via a pivot pin.

11. The apparatus of claim 10, wherein the threaded shaft comprises a threaded section, wherein the elongated coupling member comprises a complementary threaded section meshing the threaded section of the threaded shaft.

12. The apparatus of claim 11, wherein the elongated coupling member is rotatably constrained relative to the handle body.

13. The apparatus of claim 12, wherein the adjustment body is configured to, while rotating about the second axis, rotate the threaded shaft about the longitudinal axis such that the threaded shaft drives the elongated coupling member between the first closed position and the second closed position via engagement between the threaded section and the complementary threaded section.

14. The apparatus of claim 13, wherein the adjustment body is configured to, while rotating about the first axis, drive translation of the threaded shaft along the longitudinal axis.

15. The apparatus of claim 14, wherein the adjustment body is configured to rotate about the longitudinal axis while rotating about the second axis.

16. The apparatus of claim 15, wherein the first axis is defined by the pivot pin.

17. An apparatus, comprising:
   (a) a handle body;
   (b) a shaft assembly extending distally from the handle body;
   (c) a stapling assembly comprising:
      (i) a staple deck fixed relative to the shaft assembly,
      (ii) a staple driver, wherein the staple driver is operable to actuate relative to the staple deck between an unfired position and a fired position to drive a plurality of staples into tissue, and
      (iii) an elongated coupling member configured to actuate relative to the staple deck and the staple driver;
   (d) an anvil configured to selectively couple with the elongated coupling member, wherein the elongated coupling member is operable to actuate the anvil relative to the staple deck when the anvil is selectively coupled with the elongated coupling member; and
   (e) a closure system comprising an adjustment body and an elongated closure member extending distally from the adjustment body, wherein the elongated closure member is housed within the handle body, wherein the adjustment body is located proximally relative to the handle body, wherein the closure system is configured to actuate the anvil, while coupled to the elongated coupling member, between a distal position, a first closed position, and a second closed position, wherein the adjustment body is configured to rotate about a first axis to drive the anvil between the distal position and the first closed position, wherein the entire first axis is located proximally relative to the handle body, wherein the adjustment body is configured to rotate about a second axis to drive the anvil between the first closed position and the second closed position, wherein the second axis extends through the handle body.

18. An apparatus, comprising:
(a) a handle body;
(b) a shaft assembly extending distally from the handle body;
(c) a stapling assembly comprising:
   (i) a staple deck fixed relative to the shaft assembly,
   (ii) a staple driver, wherein the staple driver is operable to actuate relative to the staple deck between an unfired position and a fired position to drive a plurality of staples into tissue, and
   (iii) an elongated coupling member configured to actuate relative to the staple deck and the staple driver;
(d) an anvil configured to selectively couple with the elongated coupling member, wherein the elongated coupling member is operable to actuate the anvil relative to the staple deck when the anvil is selectively coupled with the elongated coupling member; and
(e) a closure system comprising an adjustment body, wherein the closure system is configured to actuate the anvil, while coupled to the elongated coupling member, between a distal position, a first closed position, and a second closed position, wherein the adjustment body is configured to actuate in a first motion to drive the anvil between the distal position and the first closed position, wherein the adjustment body is configured to actuate in a second motion to drive the anvil between the first closed position and the second closed position,
wherein the distal position comprises a sub-flush position, wherein the adjustable body is configured to translate relative to the handle body in order to actuate the elongated coupling member distally from the sub-flush position toward an open position,
wherein the closure assembly further comprises an oblong washer configured to actuate between an obstructed position and an unobstructed position, wherein the oblong washer is configured to inhibit the adjustable body from actuating the elongated coupling member into the open position in the obstructed position.

* * * * *